US012811007B2

(12) United States Patent
Hettig et al.

(10) Patent No.: US 12,811,007 B2
(45) Date of Patent: Nov. 24, 2026

(54) CAREGIVER AND FAMILY COMMUNICATIONS

(71) Applicant: Hill-Rom Services, Inc., Batesville, IN (US)

(72) Inventors: Mark F. Hettig, Denver, CO (US); Jennifer Ann Gunn, Durham, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 275 days.

(21) Appl. No.: 17/655,211

(22) Filed: Mar. 17, 2022

(65) Prior Publication Data

US 2022/0301707 A1 Sep. 22, 2022

Related U.S. Application Data

(60) Provisional application No. 63/163,468, filed on Mar. 19, 2021.

(51) Int. Cl.
*G16H 40/67* (2018.01)

(52) U.S. Cl.
CPC .................................. *G16H 40/67* (2018.01)

(58) Field of Classification Search
None
See application file for complete search history.

(56) References Cited

U.S. PATENT DOCUMENTS 8,095,381 B2 1/2012 Simons et al.
8,818,823 B2 8/2014 Ackerson et al.
8,930,481 B2 1/2015 Zhang et al.
8,990,336 B2 3/2015 Brown
9,058,635 B1 * 6/2015 Rybkin .................. G16H 10/60
10,235,501 B2 3/2019 Allinson et al.
2005/0209886 A1 * 9/2005 Corkern ................. G06Q 10/10 235/377
2007/0280431 A1 * 12/2007 Alpsten .................. G16H 80/00 379/38

(Continued)

FOREIGN PATENT DOCUMENTS

CN 104902124 A * 9/2015 ........... A61B 6/5294
CN 109378085 A 2/2019

(Continued)

OTHER PUBLICATIONS

Gordon et. al., "Digital mobile technology facilitates HIPAA-sensitive perioperative messaging, improves physician-patient communication, and streamlines patient care", Patient Saf Surg. May 23, 2015;9:21. (Year: 2015).*

(Continued)

*Primary Examiner* — Anne-Marie K Alderson
(74) *Attorney, Agent, or Firm* — Merchant & Gould P.C.

(57) ABSTRACT

A device for managing caregiver and family communications is described. The device displays a screen including predefined options for selecting at least one of a pre-generated message, a patient condition summary, and a patient plan. The predefined options are based on where a patient is admitted in a clinical care environment. The device generates an update of the patient based on a selection of the at least one of the message, the patient condition summary, and the patient plan. The device sends the update to a second device operated by a family member of the patient.

13 Claims, 50 Drawing Sheets

(56) References Cited

U.S. PATENT DOCUMENTS

2008/0306759 A1* 12/2008 Ilkin .................... G16H 40/63 715/765
2009/0281393 A1 11/2009 Smith
2009/0319298 A1* 12/2009 Weiss .................... G16H 80/00 707/999.107
2010/0094657 A1* 4/2010 Stern .................... G16H 40/63 715/845
2010/0128104 A1* 5/2010 Fabregat ................ H04L 67/12 348/E7.083
2010/0223073 A1* 9/2010 Nearman ............... G16H 40/67 380/255
2011/0046976 A1 2/2011 Peruzzi
2011/0245630 A1* 10/2011 St. Pierre ............... G06Q 10/00 600/301
2012/0011218 A1* 1/2012 Isaacs ................ G06F 16/9554 709/217
2012/0150565 A1* 6/2012 Gordon .................. G16H 80/00 705/3
2012/0185268 A1* 7/2012 Wiesner ............ H04B 7/15542 705/2
2012/0277543 A1* 11/2012 Homchowdhury .... A61B 5/002 600/300
2012/0303386 A1 11/2012 Graphim
2012/0316861 A1* 12/2012 Custer .................... G06F 40/58 704/2
2013/0297692 A1* 11/2013 Raji ...................... H04L 65/403 709/204
2014/0088991 A1 3/2014 Bakes et al.
2014/0121473 A1* 5/2014 Banet ................... A61B 5/0295 600/301
2014/0129255 A1* 5/2014 Woodson ............... G16H 10/60 705/3
2014/0278544 A1* 9/2014 Khurana ................ G16H 10/60 705/3
2014/0278548 A1 9/2014 Munro et al.
2014/0316812 A1 10/2014 Hathor et al.
2015/0012299 A1 1/2015 Kohli
2015/0025904 A1* 1/2015 Rao ...................... G06Q 10/107 705/2
2015/0112709 A1* 4/2015 Bowman ................ G16H 50/70 705/2
2015/0120321 A1* 4/2015 David .................... G16H 10/60 705/2
2015/0207948 A1* 7/2015 Yamaguchi ........ H04N 1/00374 358/452
2015/0213202 A1* 7/2015 Amarasingham ....... G16Z 99/00 705/2
2015/0234994 A1* 8/2015 Verkerk ................. G06Q 10/10 705/2
2015/0339460 A1 11/2015 Marsico
2016/0180026 A1 6/2016 Kim et al.
2016/0284202 A1* 9/2016 Traughber ............. G16H 80/00
2017/0124276 A1 5/2017 King
2017/0147791 A1* 5/2017 Dalton ................... G16H 70/60
2017/0308648 A1* 10/2017 Clarke ................... G16H 10/60
2018/0013707 A1* 1/2018 Murphy .................. H04L 51/18
2018/0144154 A1* 5/2018 Shacham ............ H04L 63/0428
2018/0343257 A1* 11/2018 Frankel ................... H04L 63/20
2018/0358117 A1 12/2018 Neagle
2019/0043621 A1* 2/2019 Celmins ............... H04N 23/695
2019/0133445 A1 5/2019 Eteminan et al.
2019/0304576 A1* 10/2019 Mendoza ............... G16H 40/20
2019/0325996 A1 10/2019 Kaakpema
2020/0019726 A1* 1/2020 Perecman ............... G06F 21/40
2020/0075147 A1 3/2020 Mahmoud
2020/0090820 A1 3/2020 Nath
2020/0118680 A1* 4/2020 Rao ........................ G16H 10/60
2020/0160950 A1* 5/2020 Phillips .................. G16H 10/60
2021/0027899 A1* 1/2021 Blanshard .............. G16H 40/67
2021/0133855 A1* 5/2021 Ramirez .............. G06Q 10/087
2022/0139570 A1 5/2022 Hettig et al.

FOREIGN PATENT DOCUMENTS

CN 110060768 A 7/2019
CN 111696643 A 9/2020
JP 6771306 B2 10/2020
KR 200459026 Y1 * 7/2011
WO WO-2011058293 A1 * 5/2011 ........... G08B 21/245

OTHER PUBLICATIONS

Lehigh Valley Health (LVH) Nework's EASE App webpage; accessed via Wayback.org; Jul. 23, 2019. (Year: 2019).*

Atrium Health Wake Forest Baptist, News Releases: New App Helps Reduce Waiting Room Stress for Patients' Families; Feb. 13, 2019 (Year: 2019).*

"Hucu.ai Launches Patient/Family Messaging, Easing COVID-19 Communication", Hucu.ai, Jun. 9, 2020, pp. 1-3.

"Better Communication. Delivered." link: https://www.careloop.co/who-we-help/post-acute-long-term-care/, Careloop, Jan. 21, 2021, Retrieved on Jan. 28, 2021, pp. 1-11.

"Inpatient Care Mobile App Development", Sciencesoft USA Corporation, link: https://www.scnsoft.com/case-studies/inpatient-care-mobile-app, Jan. 21, 2021, pp. 1-6.

Family App, INVU Care, https://www.invucare.com/family-app/, pp. 1-5 (2020).

Extended European Search Report for Application No. 22162729.2 dated Jul. 27, 2022 (9 pages).

* cited by examiner

CAREGIVER AND FAMILY COMMUNICATIONS

BACKGROUND

It can be stressful and confusing for family members of patients who are admitted to a healthcare facility such as a hospital for an extended period of time or who are undergoing a medical procedure such as surgery. This can be especially true for parents of newborn babies who are admitted in a neonatal intensive care unit (NICU) for an extended period of time.

Family members are typically eager to receive updates on the progress of their loved one. However, it can be challenging to communicate the patient's status with family members in an effective and efficient manner.

SUMMARY

The present disclosure generally relates to caregiver and family communications. In one configuration, a device includes an application for managing updates from caregivers that are received on a second device operated by a family member of the patient. Various aspects are described in this disclosure, which include, but are not limited to, the following aspects.

One aspect relates to a device for managing caregiver and family communications. The device comprises: at least one processor; and a memory storing instructions which, when executed by the at least one processor, cause the at least one processor to: display a screen including predefined options for selecting at least one of a pre-generated message, a patient condition summary, and a patient plan, the predefined options are based on where a patient is admitted in a clinical care environment; generate an update of the patient based on a selection of the at least one of the message, the patient condition summary, and the patient plan; and send the update to a second device operated by a family member of the patient.

Another aspect relates to a device for managing caregiver and family communications. The device comprises: at least one processor; and a memory storing instructions which, when executed by the at least one processor, cause the at least one processor to: receive an invitation to link the device to a patient; receive an update on the patient from a second device operated by a caregiver responsible for providing healthcare to the patient; and display the update, wherein the update includes at least one of a pre-generated message, a patient condition summary, and a patient plan each selected from predefined options based on where the patient is admitted in a clinical care environment.

Another aspect relates to a method of managing caregiver and family communications, the method comprising: displaying a screen including predefined options for selecting at least one of a pre-generated message, a patient condition summary, and a patient plan, the predefined options being based on where a patient is admitted in a clinical care environment; generating an update of the patient based on a selection of the at least one of the message, the patient condition summary, and the patient plan; and sending the update to a second device operated by a family member of the patient.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
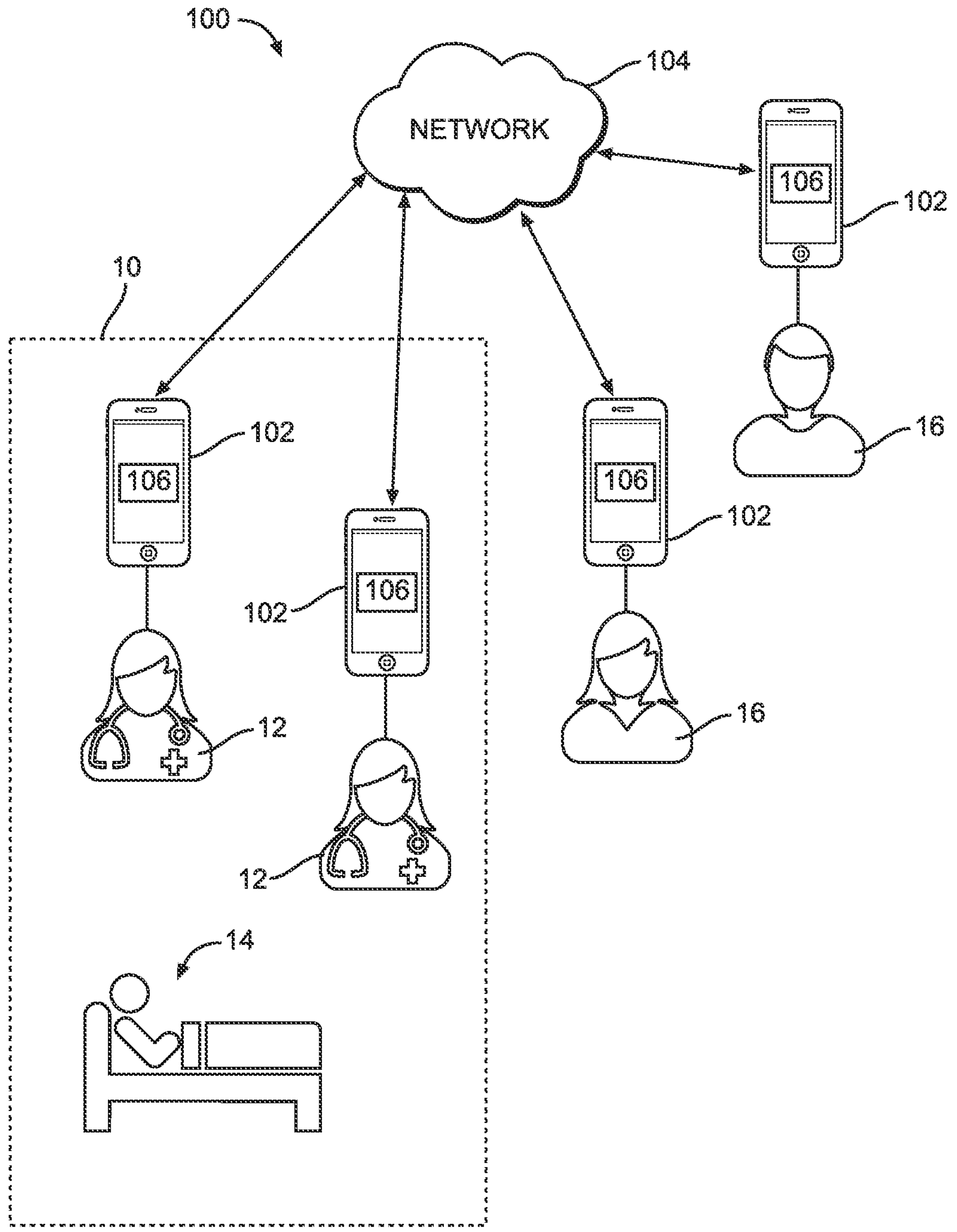
FIG. 1 is a schematic diagram of an example of a system that includes mobile devices that each operate a family communications application for managing communications between one or more caregivers and one or more family members of a patient.

FIG. 1 is a schematic diagram of a system 100 that includes mobile devices 102 that each operate a family communications application 106 for managing updates from one or more caregivers 12 providing care to a patient 14 in a clinical care environment 10 to one or more family members 16 of the patient. The updates from the caregivers 12 to the family members 16 are communicated via a communications network 104.

The system 100 allows the family members 16 to receive regular updates on the condition and status of the patient 14 throughout the patient's stay in a clinical care environment 10 such as a hospital. Additionally, the system 100 can be used by the caregivers 12 to inform the family members 16 to schedule in-person meetings or phone calls such that the family members 16 will not need to wait inside the clinical care environment 10, thereby allowing the family members 16 to wait in a more comfortable setting such as in their home.

The system 100 can improve the communications between the caregivers 12 and the family members 16 such that the family members 16 are informed and updated regarding their loved one's care. Also, the system 100 can reduce the number of calls received by the caregivers 12 from the family members 16, allowing the caregivers 12 to focus their attention on patient care, which can result in an increase in patient satisfaction scores. Additionally, the system 100 can prevent the spread of disease by eliminating the need for the family members 16 to wait in a crowded area such as the lobby or waiting room of a hospital.

As shown in FIG. 1, the caregivers 12 and patient 14 are located within the clinical care environment 10, and the family members 16 are located outside of the clinical care environment 10. FIG. 1 is provided by way of illustration only and it is contemplated that in some scenarios the family members 16 may be located within the clinical care environment 10, but in a different area from where the patient 14 is located. Generally, the family members 16 are located remotely from the location of the patient 14. Also, the family members 16 may be physically separated from one another such that they are not located together in the same area.

In some instances, the clinical care environment 10 is an inpatient acute care hospital setting where a patient is expected to be admitted for an extended period of time. Examples of such settings may include, without limitation, a med surg unit, an intensive care unit (ICU), a neonatal intensive care unit (NICU), medical intensive care unit (MICU), coronary care unit (CCU), and the like. In such settings, the family members 16 can typically expect updates from the caregivers 12 about 1-3 times per day, depending on the particular unit.

In some other instances, the clinical care environment 10 is an outpatient care setting or an operating room where a procedure is being performed on the patient 14. In such examples, the family members 16 typically expect updates every 30 minutes to 1 hour.

The caregivers 12 can include nurses, doctors, and other caregivers who are responsible for the care of the patient 14. The caregivers 12 send patient updates to the family members 16 using the family communications application 106 on their mobile devices 102.

The family members 16 are related to the patient 14 such as a parent, spouse, brother, sister, and the like. In some examples, the family members 16 include friends or acquaintances of the patient 14. The family members 16 receive patient updates from the caregivers 12 using the family communications application 106 installed on their mobile devices 102.

The communications network 104 can include any type of wired or wireless connections or any combinations thereof. Examples of wireless connections include broadband cellular network connections such as 4G or 5G. In some instances, wireless connections can also be accomplished using Bluetooth, Wi-Fi, and the like.

Figure 2:
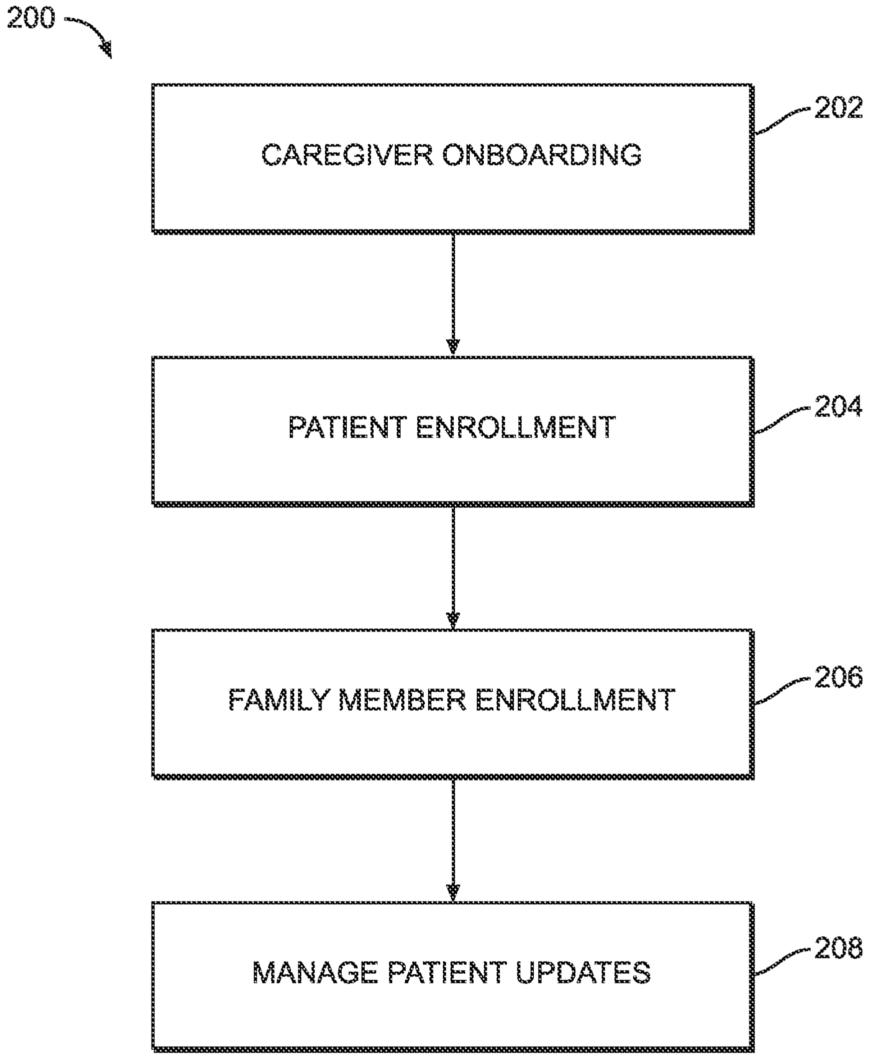
FIG. 2 illustrates an example of a method of managing communications between the caregivers and family of the patient using the family communications application of FIG. 1.

FIG. 2 illustrates an example of a method 200 of managing communications between the caregivers and family members of the patient using the family communications application 106. In FIG. 2, the method 200 is performed from the perspective of a caregiver 12 who uses the family communications application 106 on their mobile device 102. The method 200 includes an operation 202 of providing caregiver onboarding, an operation 204 of providing patient enrollment, an operation 206 of providing family member enrollment, and an operation 208 of managing patient updates. Each of these operations will be described in more detail below.

Figure 3:
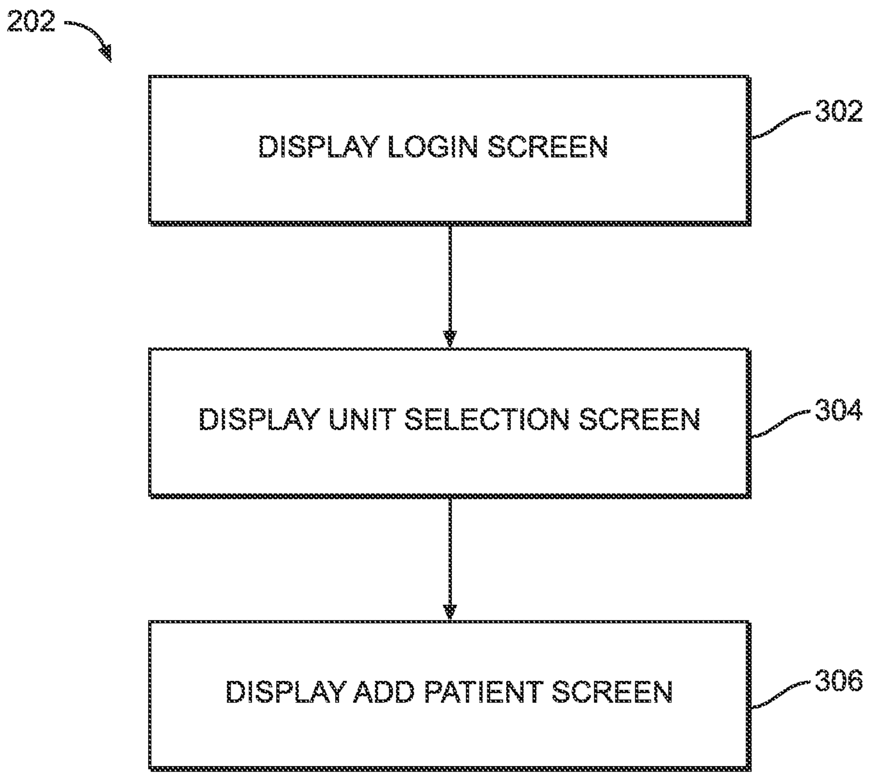
FIG. 3 illustrates an example of an operation of providing caregiver onboarding in the method of FIG. 2.

FIG. 3 illustrates in more detail the operation 202 of providing caregiver onboarding. The operation 202 includes a step 302 of displaying a login screen for the caregiver 12 to log into the family communications application 106, followed by a step 304 of displaying a unit selection screen for the caregiver 12 to select a unit within the clinical care environment, followed by a step 306 of displaying an add patient screen. In some examples, step 304 is optional such that the unit selection screen is not displayed after the caregiver logs into the family communications application 106. These steps will now be described in more detail with reference to FIGS. 4-6.

Figure 4:
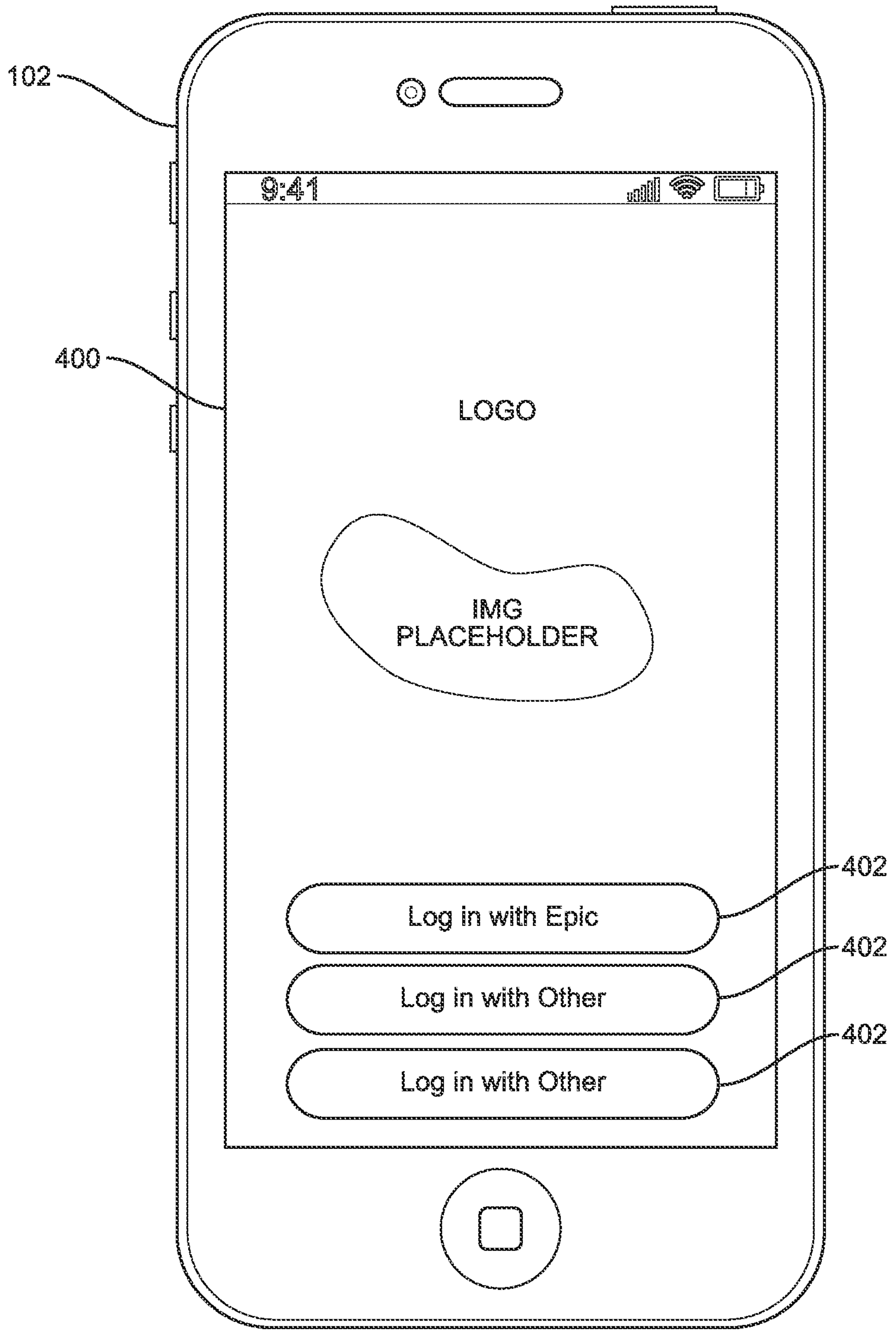
FIG. 4 illustrates an example of a login screen that is generated on a mobile device of a caregiver by the family communications application of FIG. 1.

FIG. 4 illustrates an example of a login screen 400 that is generated on a mobile device 102 by the family communications application 106 during step 302. The login screen 400 is displayed when the caregiver 12 opens the family communications application 106 on their mobile device 102. The login screen 400 can provide one or more options 402 for the caregiver 12 to login. At least some of the options 402 allow the caregiver 12 to login into the family communications application 106 using single sign-on (SSO) such as by using an ID and password from related software applications that are accessible on the mobile device 102.

Figure 5:
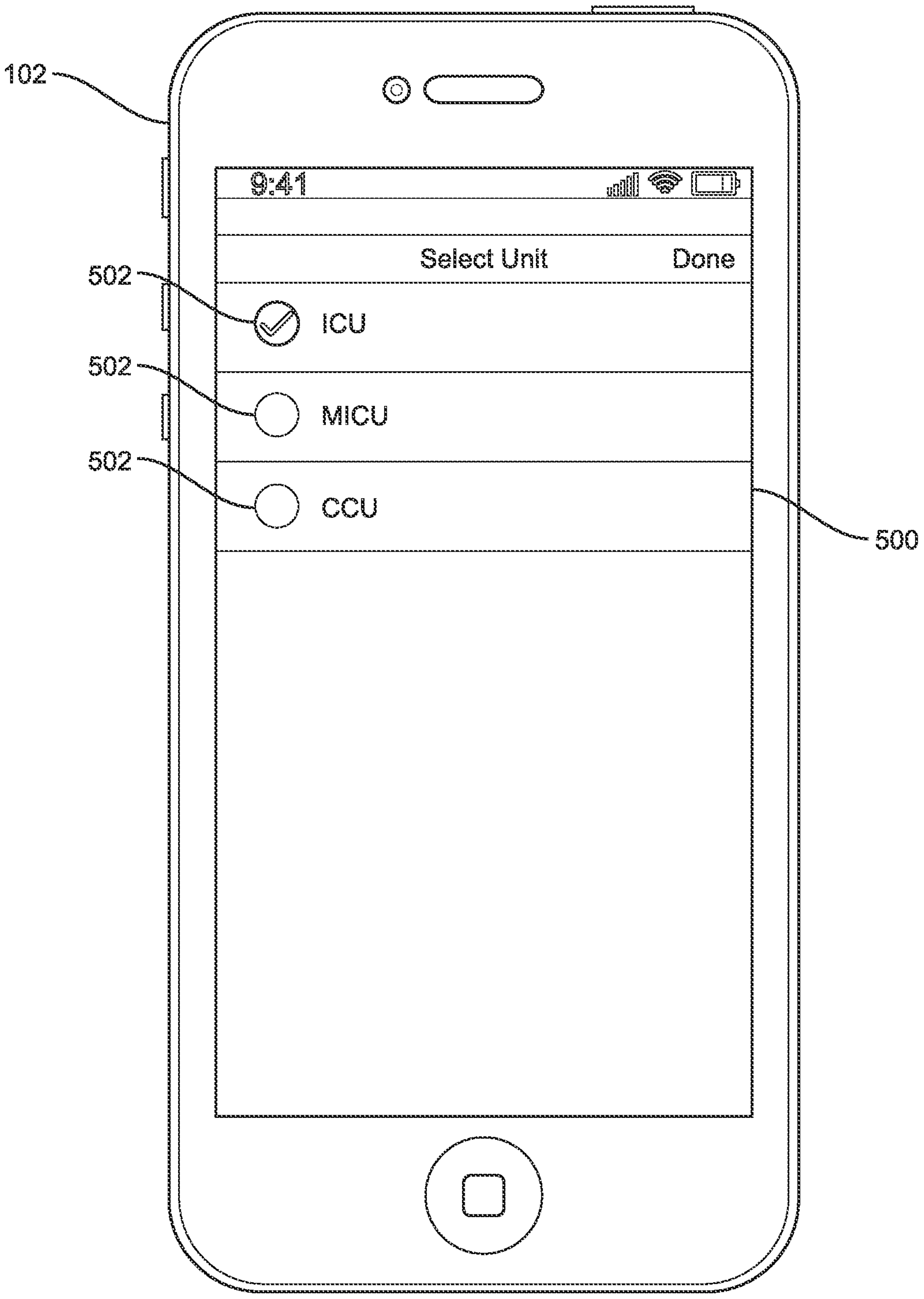
FIG. 5 illustrates an example of a unit selection screen generated on the mobile device of the caregiver by the family communications application of FIG. 1.

FIG. 5 illustrates an example of a unit selection screen 500 that is provided on the mobile device 102 by the family communications application 106 during step 304. The unit selection screen 500 is generated upon a successful login by the caregiver 12. As described above, in some examples, step 304 is optional such that the unit selection screen 500 is not displayed. When the unit selection screen 500 is displayed, it provides one or more units 502 within the clinical care environment 10 for the caregiver 12 to select. The one or more units 502 are preconfigured and are identified for display based on the login credentials of the caregiver 12. For example, the caregiver 12 may be assigned to a plurality of units within the clinical care environment 10, and the family communications application 106 identifies and displays these units based on the caregiver's login credentials. In the example of FIG. 5, the unit selection screen 500 displays an ICU unit, a MICU unit, and a CCU unit for selection by the caregiver 12. Additional types of units may be displayed based on the credentials of the caregiver 12.

The caregiver 12 selects at least one unit from the one or more units 502 according to their shift assignment, and then selects the done icon 504 to confirm the selection of the unit. In the example illustrated in FIG. 5, the ICU unit is shown as selected on the unit selection screen 500 generated on the mobile device 102. Once selected, the family communications application 106 is configured based on the unit selected by the caregiver such that the types of messages and frequency of messaging between the caregiver 12 and the family members 16 is configured based on the unit selected by the caregiver 12, as will be described in more detail below. In alternative examples, the family communications application 106 is configured based on the unit of the patient 14 identified from the patient enrollment in operation 204 such that the types of messages and frequency of messaging between the caregiver 12 and the family members 16 is configured based on the unit of the patient 14, as will be described in more detail below.

Figure 6:
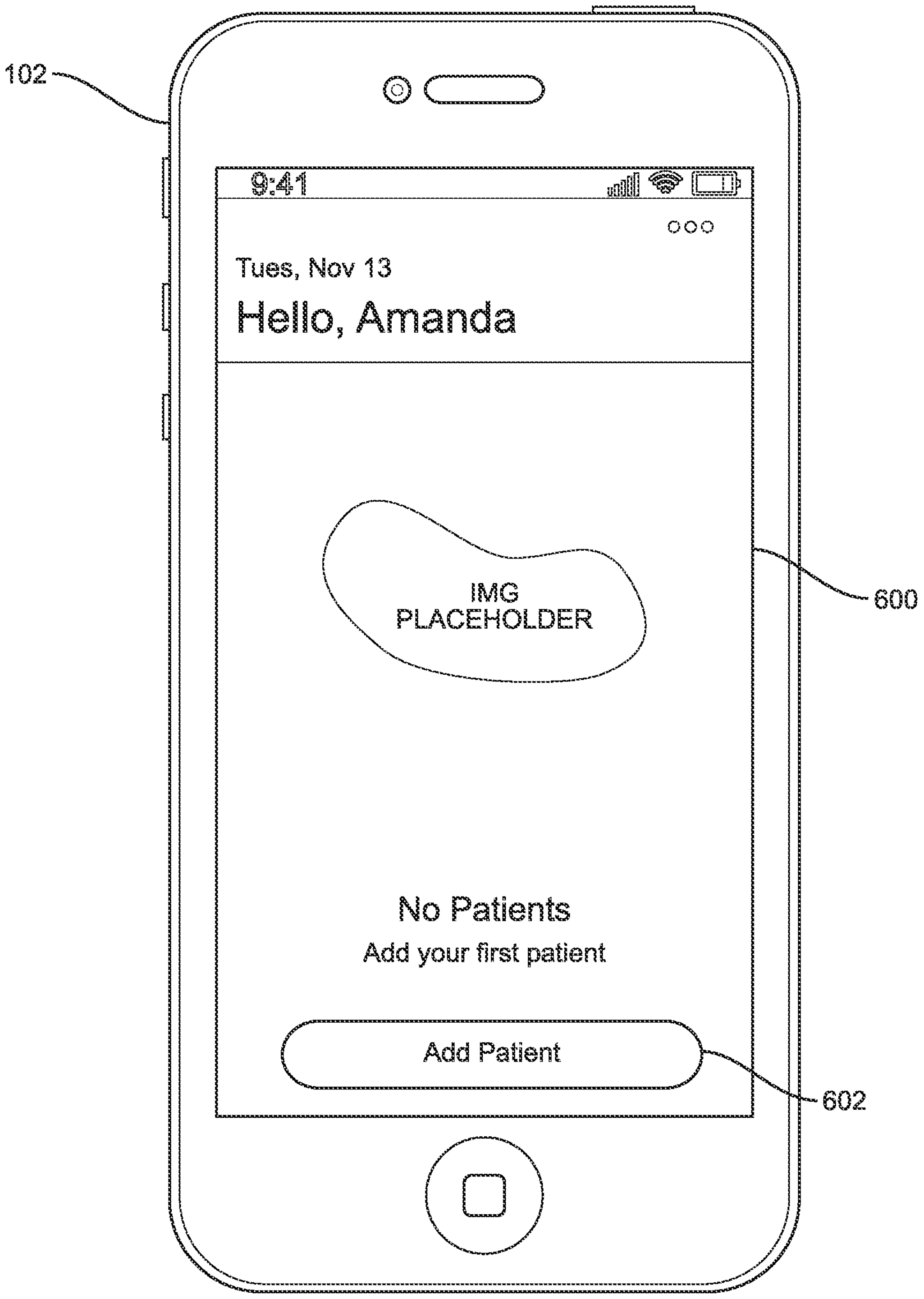
FIG. 6 illustrates an example of an add patient screen generated on the mobile device of the caregiver by the family communications application of FIG. 1.

FIG. 6 illustrates an example of an add patient screen 600 that is generated on the mobile device 102 by the family communications application 106 during step 306. The add patient screen 600 can be generated upon selection of a unit from the one or more units 502 by the caregiver 12. The add patient screen 600 does not display any patients when the caregiver 12 logs into the family communications application 106 for the first time. In some examples, the add patient screen 600 does not display any patients each day the caregiver logs in for the first time, regardless of whether it is the caregiver's first time using the family communications application 106. The add patient screen 600 displays an add patient icon 602 for the caregiver to select. Once the add patient icon is selected, the caregiver 12 is prompted to an enroll a patient.

Figure 7:
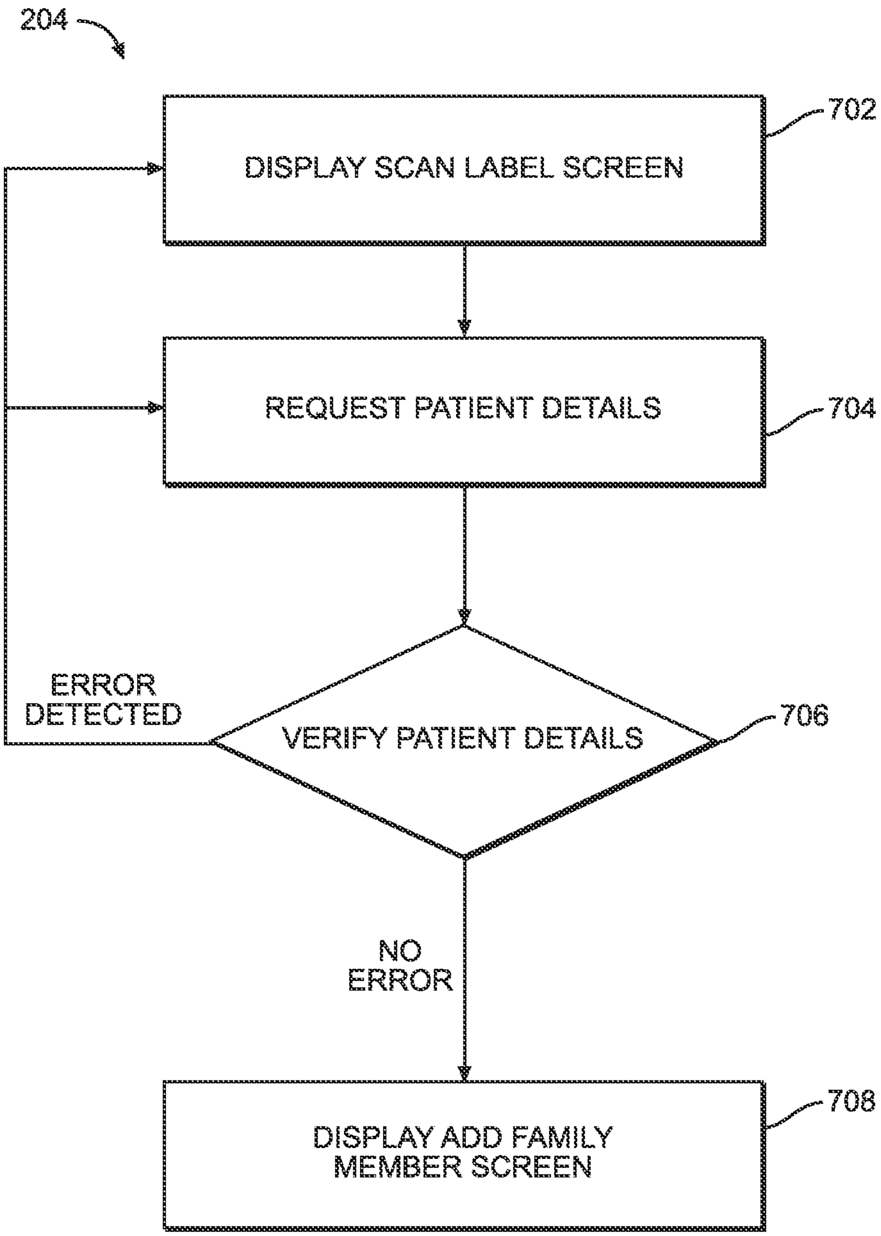
FIG. 7 illustrates an example of an operation of providing patient enrollment in the method of FIG. 2.

FIG. 7 illustrates in more detail the operation 204 of providing patient enrollment in the method 200 of FIG. 2. As shown in FIG. 7, the operation 204 includes a step 702 of displaying a scan label screen, a step 704 of requesting patient details, a step 706 of verifying the patient details, and a step 708 of displaying an add family member screen. Each of these steps will be described in more detail with reference to FIGS. 8 and 9.

Figure 8:
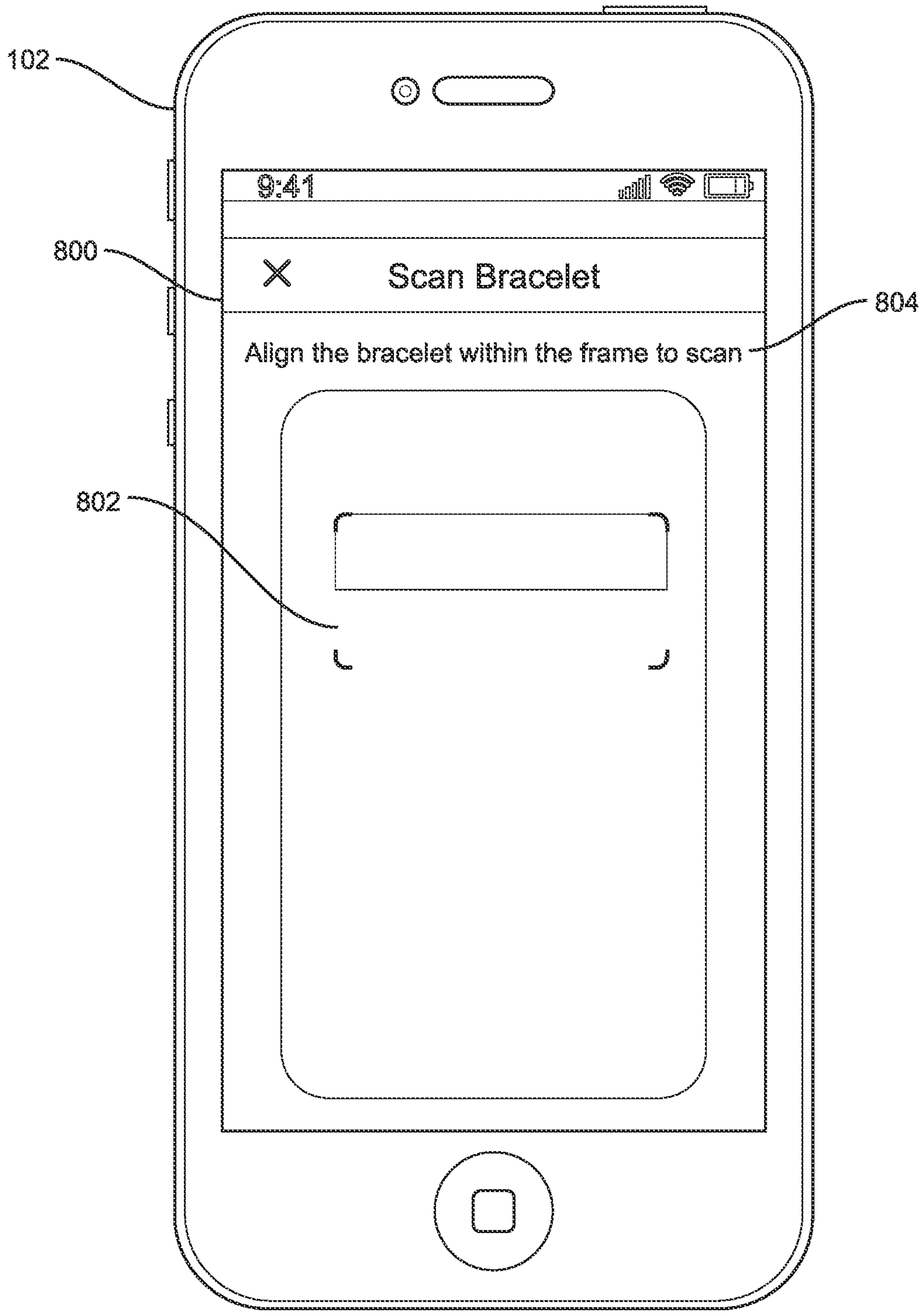
FIG. 8 illustrates an example of a scan label screen generated on the mobile device of the caregiver by the family communications application of FIG. 1.

FIG. 8 illustrates an example of a scan label screen 800 that is generated on the mobile device 102 by the family communications application 106 during step 702. The scan label screen 800 is displayed when the caregiver 12 selects the add patient icon 602 from the add patient screen 600 shown in FIG. 6. The scan label screen 800 displays a frame 802 that surrounds an image feed from a camera of the mobile device 102. The scan label screen 800 can include instructions 804 for the caregiver 12 to align the frame 802 with a label that includes machine-readable data that identifies the patient 14. For example, the machine-readable data can be a barcode, a QR code, or similar data representation that is recognizable by the camera of the mobile device 102. The label can be on a bracelet worn by the patient 14 or on a piece of equipment associated with the patient 14 such as the patient's bed or monitoring equipment connected to the patient. The family communications application 106 uses the camera of the mobile device 102 to automatically detect and scan the label when aligned inside the frame 802.

Figure 9:
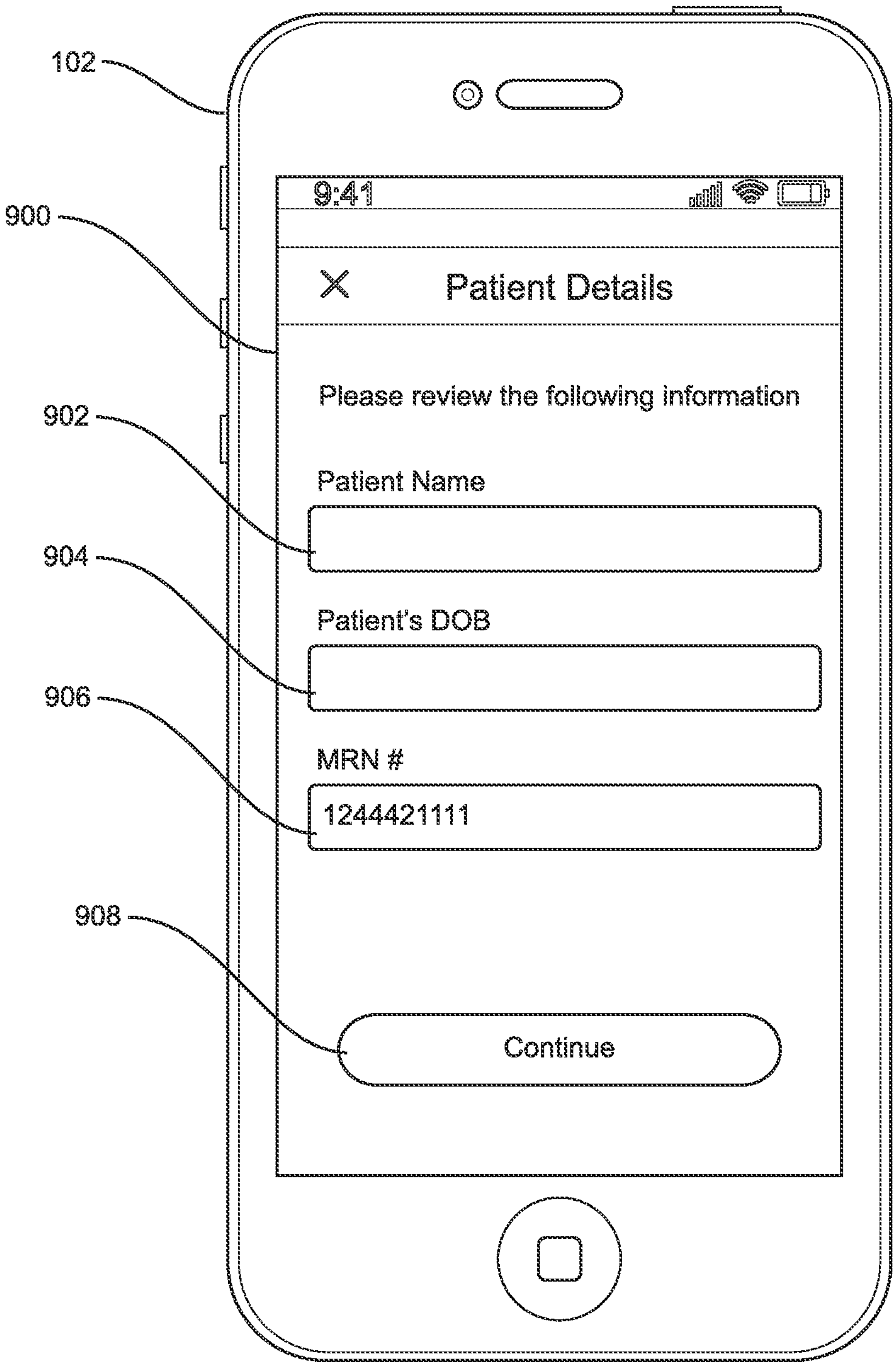
FIG. 9 illustrates an example of an add patient details screen generated on the mobile device of the caregiver by the family communications application of FIG. 1.

FIG. 9 illustrates an example of an add patient details screen 900 generated on the mobile device 102 of the caregiver 12 by the family communications application 106. The add patient details screen 900 is automatically generated upon a successful scan of the label that includes machine-readable data that identifies the patient 14. The add patient details screen 900 includes a patient medical record number field 906 that is automatically populated based on the successful scan of the label. The add patient details screen 900 can include additional fields that request the caregiver 12 to add patient details such as a patient name field 902 and a patient date of birth field 904. In certain aspects, requiring the caregiver 12 to enter additional patient details such as the patient's name and date of birth ensures that the correct patient is being added, and thereby removes the opportunity for a patient to be incorrectly added by mistake. The add patient details screen 900 provides a continue icon 908 that is selectable by the caregiver 12 once the additional patient details have been entered into the appropriate fields on the screen.

Next, the family communications application 106 performs step 706 to verify the patient details such as the patient's name, date of birth, and medical record number in response to selection of the continue icon 908. If an error is detected, the family communications application 106 may request the caregiver 12 to re-enter the patient details (i.e., repeat the step 704) or re-scan the label that identifies the patient (i.e., repeat the step 702). If no errors are detected, the family communications application 106 proceeds to step 708 of displaying an add family screen 1100, an example of which is shown in FIG. 11.

Figure 10:
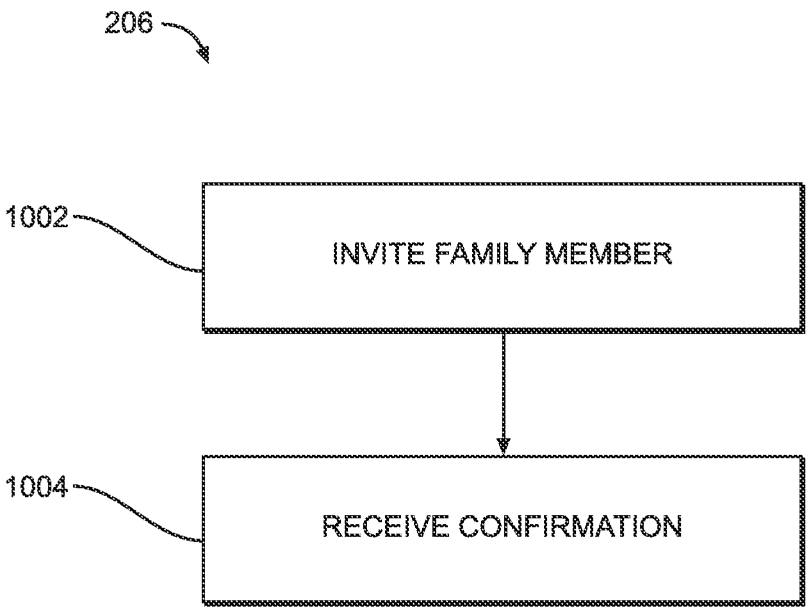
FIG. 10 illustrates an example of an operation of providing family member enrollment in the method of FIG. 2.

FIG. 10 illustrates in more detail the operation 206 of providing family member enrollment in the method 200 of FIG. 2. As shown in FIG. 10, the operation 206 includes a step 1002 of inviting the family member 16 to download the family communications application 106, and a step 1004 of receiving confirmation that the invitation was sent to the family member 16.

Figure 11:
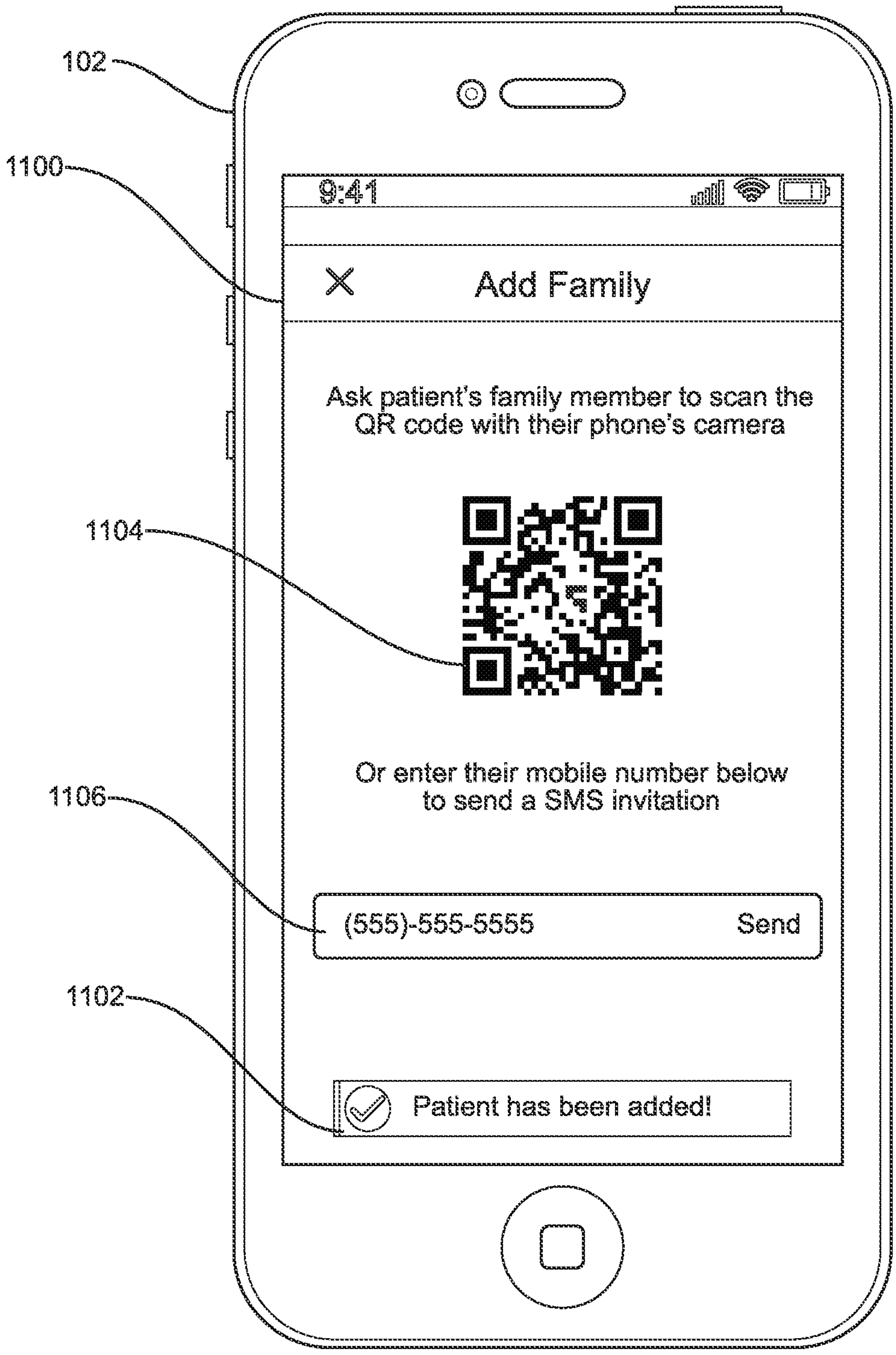
FIG. 11 illustrates an example of an add family screen generated on the mobile device of the caregiver by the family communications application of FIG. 1.

FIG. 11 illustrates an example of an add family screen 1100 that is generated on the mobile device 102 of the caregiver 12 by the family communications application 106. The add family screen 1100 is automatically generated upon the selection of the continue icon 908 in the add patient details screen 900, and upon verification that no errors are detected with respect to the patient details (i.e., patient medical record number, patient name, and patient date of birth are correct). The add family screen 1100 can include a confirmation icon 1102 that informs the caregiver 12 that the patient 14 has been successfully added.

The add family screen 1100 enables the caregiver 12 to invite the family member 16 to register with the family communications application 106, and thereby authorize the family member 16 to receive updates from the caregiver 12 on the progress and condition of the patient 14. Thus, the add family screen 1100 can be used to perform the step 1002 shown in FIG. 10.

The add family screen 1100 can display machine readable data 1104 that the family member 16 can scan with their mobile device 102 when the family member 16 is in the same location as the caregiver 12. For example, the machine readable data 1104 can be a QR code that the family member 16 can scan by using the camera of their mobile device. The machine readable data 1104 displayed on the mobile device 102 of the caregiver 12 can include metadata for linking the mobile device of the family member 16 to the patient 14.

The add family member screen 1000 can further include a mobile telephone number field 1106 in which the caregiver 12 can enter the mobile telephone number of the family member 16 to send a message to the mobile device operated by the family member 16. The message includes an invitation for the family member 16 to register and/or onboard with the family communications application 106, and thereby authorize the family member 16 to receive the patient updates from the caregiver 12. The mobile number field 1106 can be used when the family member 16 is located remotely with respect to the caregiver 12. The invitation links the mobile device of the family member 16 to the patient 14. In some examples, the message delivered to the mobile device operated by the family member 16 is a short message service (SMS) message, a multimedia messaging service (MMS), an iMessage, or other type of message.

Once the family member 16 receives the invitation on their mobile device 102 (either by scanning the machine readable data 1104 with their mobile device 102 or by receiving a message with the invitation sent via the mobile number field 1106), the family member is prompted to set up the family communications application 106 on their mobile device 102. The use of the family communications application 106 from the perspective of the family member 16 will be described in more detail below with reference to FIGS. 37-49.

The add family screen 1100 can include a check box that configures the family communications application 106 when installed on the mobile device of the family member 16 to allow or bock the family member 16 from adding secondary family members to receive updates from the family communications application 106. This configuration can be stored on the metadata or invitation linking the mobile device of the family member 16 to the patient 14. In some instances, the check box is selected by the patient 14, or an administrator in the clinical care environment 10 that is aware of the patient's home situation, or by the caregiver 12. Thus, a single primary family member, invited by the caregiver, is optionally (determined by the patient, administrator, or caregiver) allowed to invite secondary family members to receive updates on the patient. The secondary family members may not invite additional family members.

Figure 12:
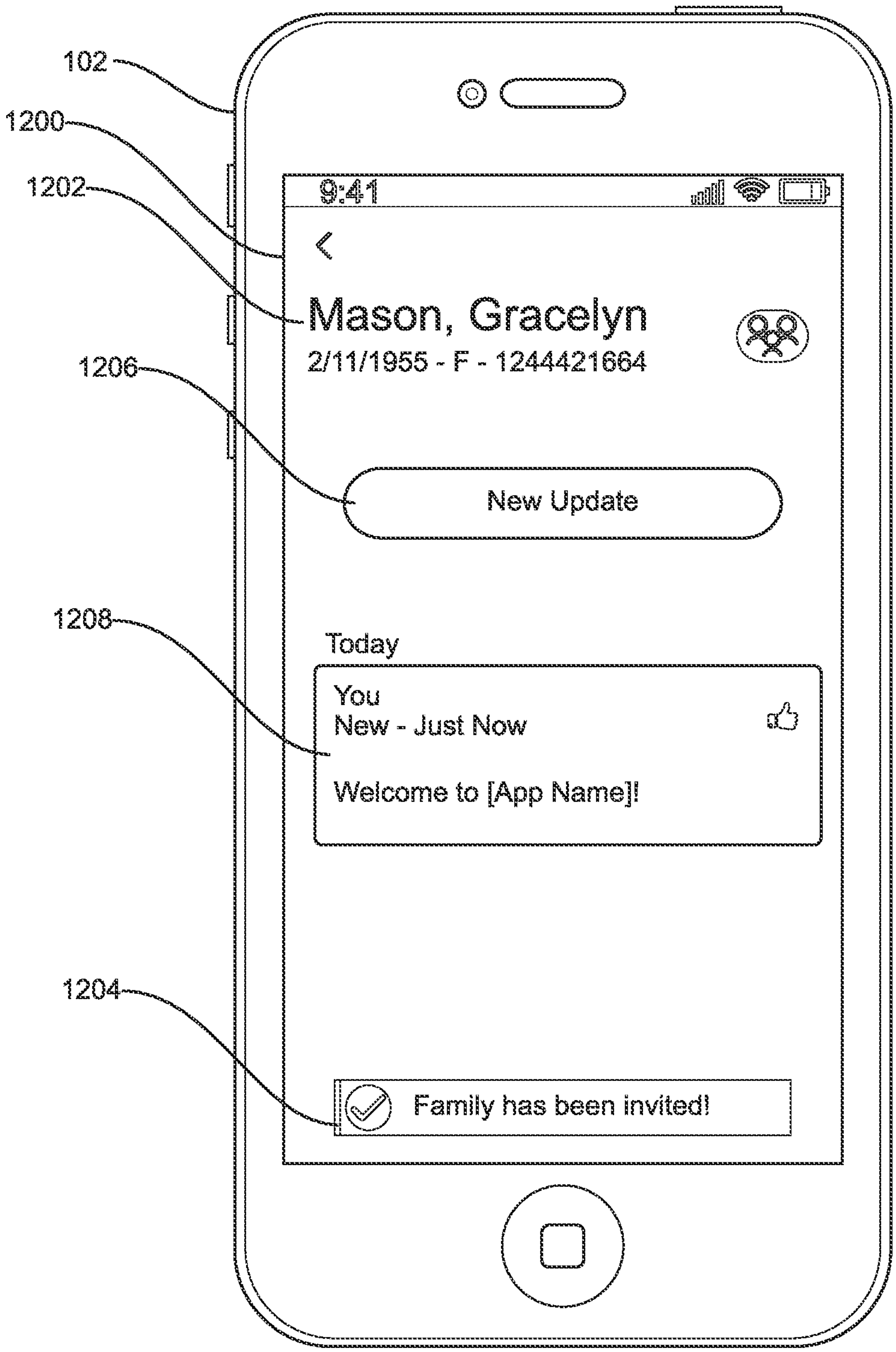
FIG. 12 illustrates an example of a confirmation screen generated on the mobile device of the caregiver by the family communications application of FIG. 1.

FIG. 12 shows an example of a confirmation screen 1200 which is displayed on the mobile device 102 of the caregiver 12 after the invitation has been sent to the family member, and which is part of the step 1004 of receiving confirmation that the family member invitation has been successfully sent. The confirmation screen 1200 displays information 1202 that identifies the patient 14 such as the patient's name, date of birth, sex, and medical record number, and displays a confirmation 1204 that the family member 16 of the patient 14 has been successfully invited. The confirmation screen 1200 can further include a new update icon 1206 for the caregiver 12 to send a new update to the family member 16. In some instances, an initial welcoming message 1208 is automatically generated and sent to the family member 16 upon the family member's successful registration with the family communications application 106.

Figure 13:
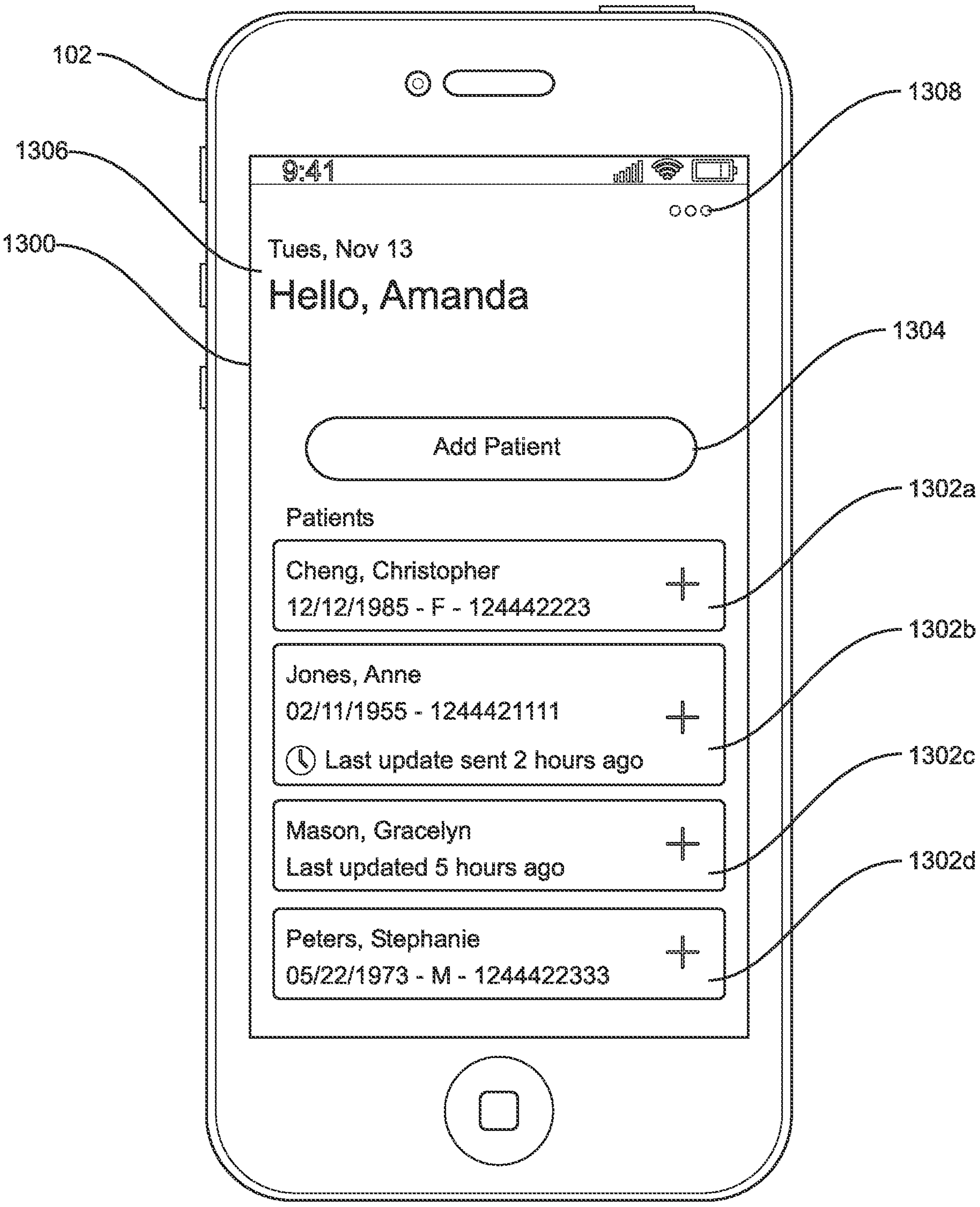
FIG. 13 illustrates an example of an enrolled patient screen generated on the mobile device of the caregiver by the family communications application of FIG. 1.

FIG. 13 illustrates an example of an enrolled patient screen 1300 that is generated on the mobile device 102 of the caregiver 12 by the family communications application 106. The enrolled patient screen 1300 displays a list of patients 1302*a*-1302*d* that have been successfully enrolled by the caregiver 12 in accordance with the operations described above. The caregiver 12 can select an add patient icon 1304 to enroll additional patients, or can select a patient 1302 to send an update to a family member, in accordance with operation 208 of the method 200. In some instances, the enrolled patient screen 1300 can include a welcoming message 1306 that identifies the caregiver 12 by their name (e.g., "Hello, Amanda") and may include the date.

Figure 14:
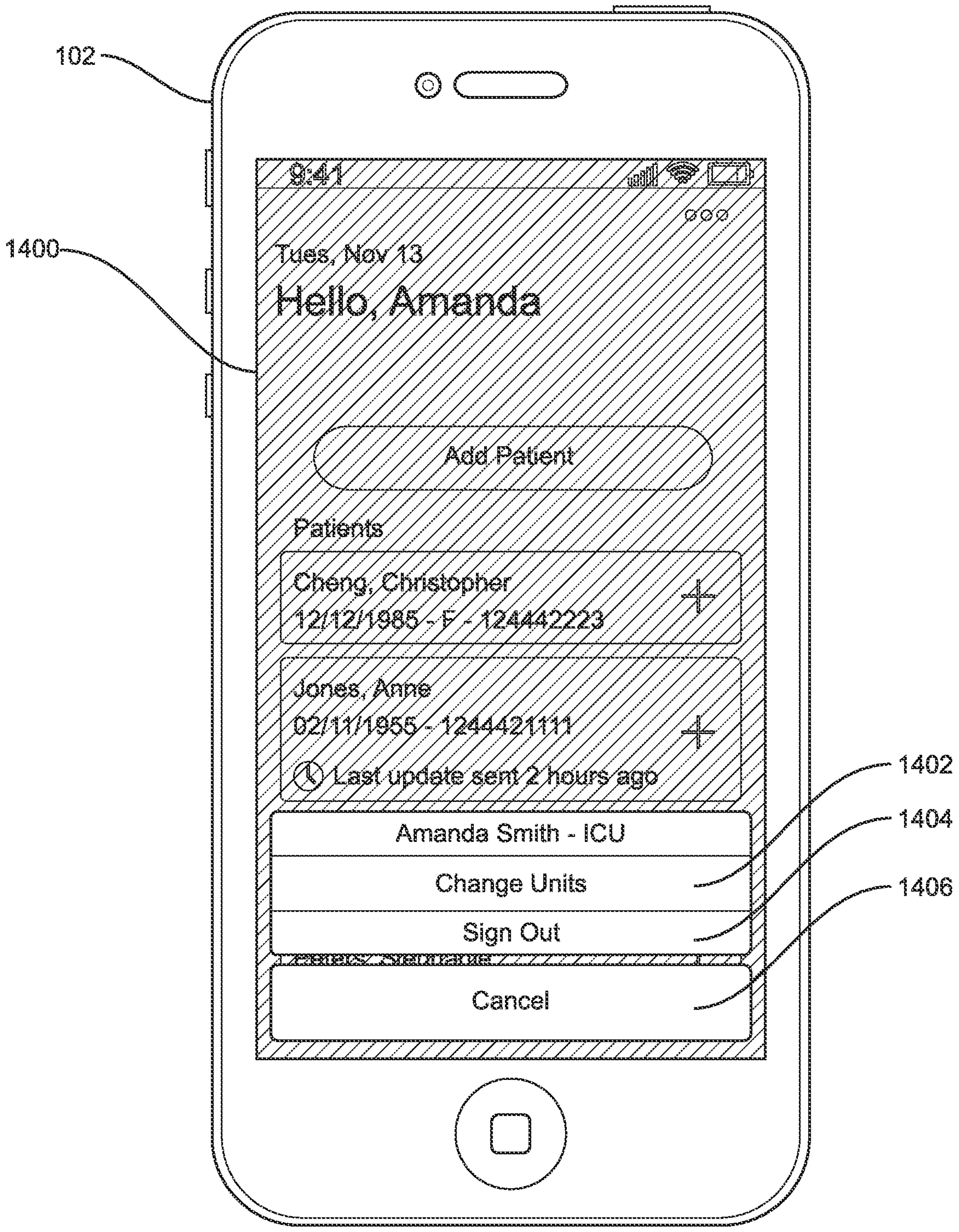
FIG. 14 illustrates an example of a log out screen generated on the mobile device of the caregiver by the family communications application of FIG. 1.

FIG. 14 illustrates an example of a log out screen 1400 that is generated on the mobile device 102 by the family communications application 106 when the caregiver 12 selects the log out icon 1308 on the enrolled patient screen 1300 shown in FIG. 13. In some examples, the log out screen 1400 can enable the caregiver 12 to select a change units option 1402 to change the type of unit selected from the unit selection screen 500 shown in FIG. 5. Upon receiving a selection of the change units option 1402, the family communications application 106 displays the unit selection screen 500 to allow the caregiver 12 to select a different unit. Upon selection of a different unit, the family communications application 106 can adapt the types of messages and frequency of messaging between the caregiver 12 and the family members 16.

The log out screen 1400 further displays a sign out option 1404 for the caregiver 12 to select. Upon selection of the sign out option 1404, the family communications application 106 displays the login screen 400 shown in FIG. 4. Also, the log out screen 1400 displays a cancel option 1406 for the caregiver 12 to return to the enrolled patient screen 1300 of FIG. 13.

Figure 15:
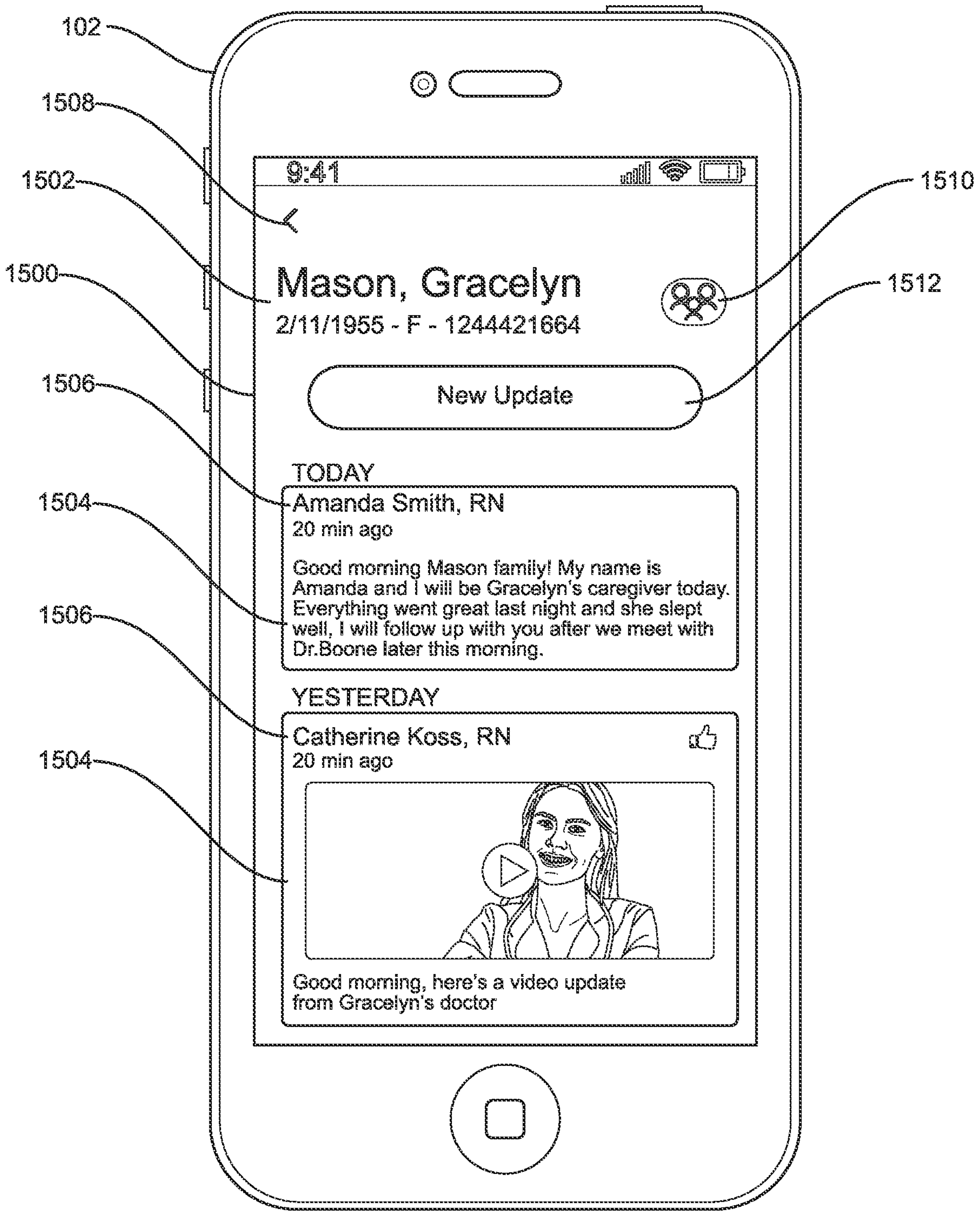
FIG. 15 illustrates an example of a family messaging screen generated on the mobile device of the caregiver by the family communications application of FIG. 1.

FIG. 15 illustrates an example of a family messaging screen 1500 that is generated on the mobile device 102 by the family communications application 106. In this example, the family messaging screen 1500 is generated in response to the caregiver 12 selecting patient 1302*c* (e.g., "Mason, Gracelyn") from the enrolled patient screen 1300 of FIG. 13. The family messaging screen 1500 displays information 1502 that identifies the patient 1302*c* such as the patient's name, date of birth, sex, and medical record number, and displays updates 1504 that were previously sent to the enrolled family member of the patient 1302*c*. The updates 1504 are listed in chronological order with the most recent update being displayed first. In some examples, the updates 1504 are categorized by the day they were sent by displaying identifiers such as "Today" or "Yesterday". Each update 1504 can also include information 1506 that identifies the date and time that the update was sent, and the name of the caregiver who sent the update.

The family messaging screen 1500 includes an icon 1508 for the caregiver 12 to select to return to the enrolled patient screen 1300 of FIG. 13. Also, the family messaging screen 1500 displays an icon 1510 that when selected by the caregiver 12 causes the family communications application 106 to display the name, contact information, and preferred language of the enrolled family members of the patient 1302*c*.

Figure 16:
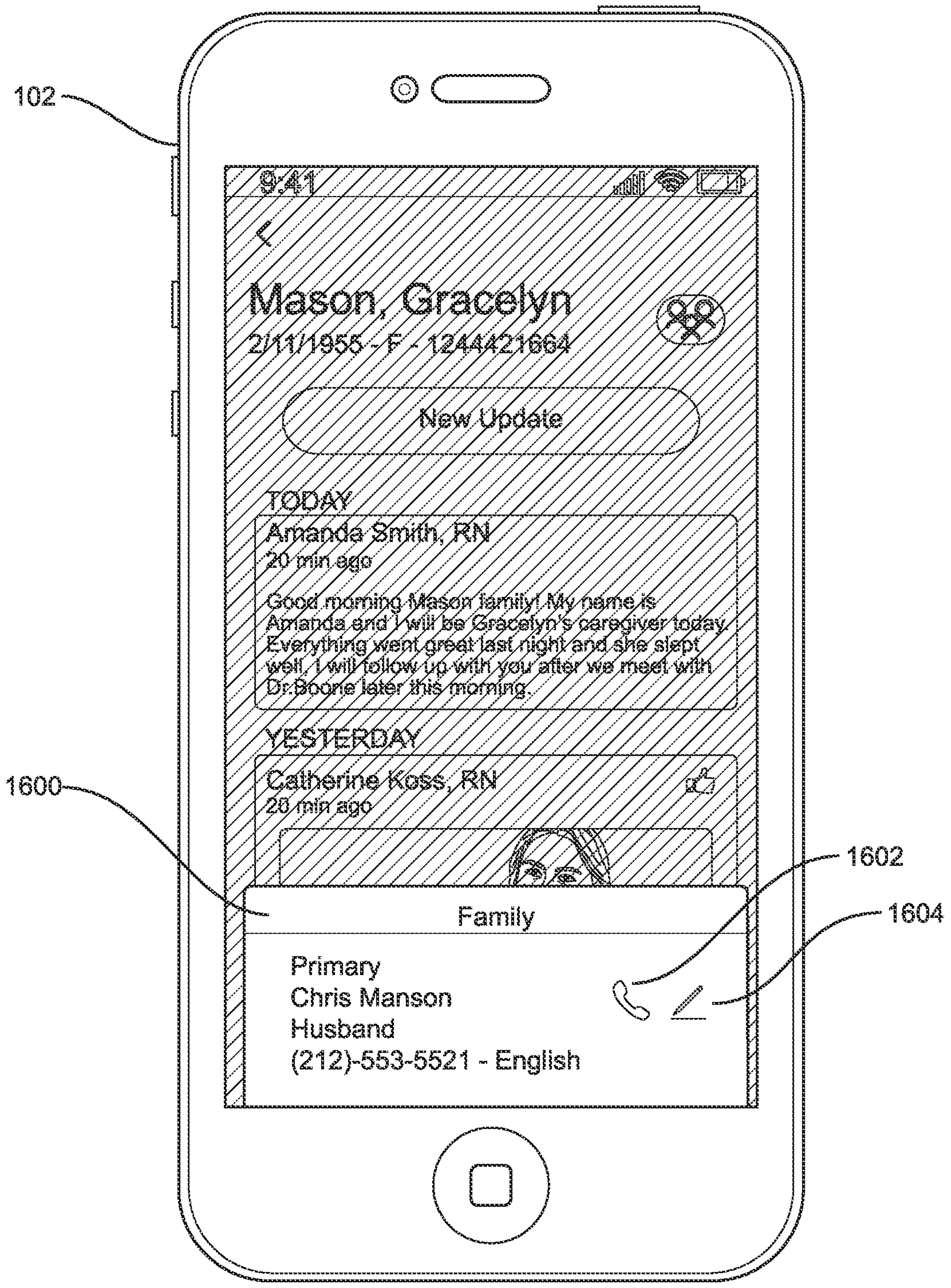
FIG. 16 illustrates an example of a family details screen generated on the mobile device of the caregiver by the family communications application of FIG. 1.

FIG. 16 illustrates an example of a family details screen 1600 generated on the mobile device 102 in response to the caregiver 12 selecting the icon 1510 on the family messaging screen 1500. The family details screen 1600 displays a primary family member of the patient 14 (e.g., the patient's husband) and may also display secondary family members (e.g., the patient's children, siblings, parents, etc.) that can be added by the primary family member. Only the primary family member is able to add or remove secondary family members from the family communications application 106. The ability for the primary family member to add secondary family members will be described in more detail below.

The family details screen 1600 displays an icon 1602 that allows the caregiver 12 to call the enrolled family members using the mobile device 102. Also, an icon 1604 allows the caregiver 12 to write a text message to the enrolled family members.

Referring back to FIG. 15, the family messaging screen 1500 includes a new update icon 1512 for the caregiver 12 to generate and send a new update to the enrolled family member of the patient 1302*c*. The family communications application 106 enables the caregiver 12 to generate and send a new update in accordance with the following description.

Figure 17:
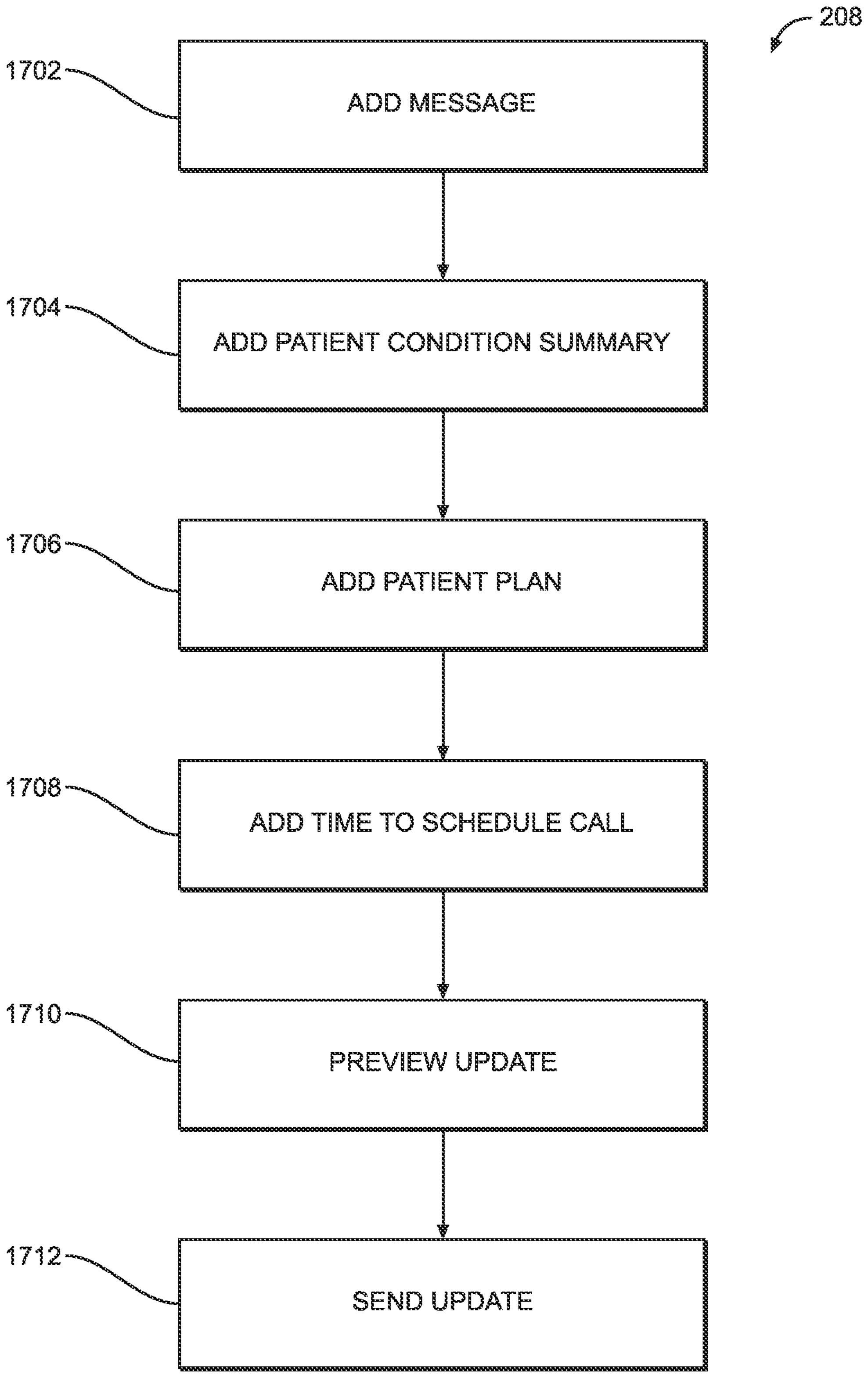
FIG. 17 illustrates an example of an operation of managing patient updates in the method of FIG. 2.

FIG. 17 illustrates the operation 208 of managing patient updates that is part of the method 200 of FIG. 2 of managing messages between caregivers and family members. In at least some examples, the operation 208 is performed to generate and send an update to a family member 16 of the patient 14. The operation 208 includes a step 1702 of adding a message, a step 1704 of adding a patient condition summary, a step 1706 of adding a patient plan, a step 1708 of adding a time to schedule a call with a family member of the patient, a step 1710 of displaying a preview of an update, and a step 1712 of sending the update to the family member. At least some of the steps 1702-1712 are optional such that some of these steps may be skipped. Each of the steps 1702-1712 will now be described in more detail with reference to FIGS. 18-36.

Figure 18:
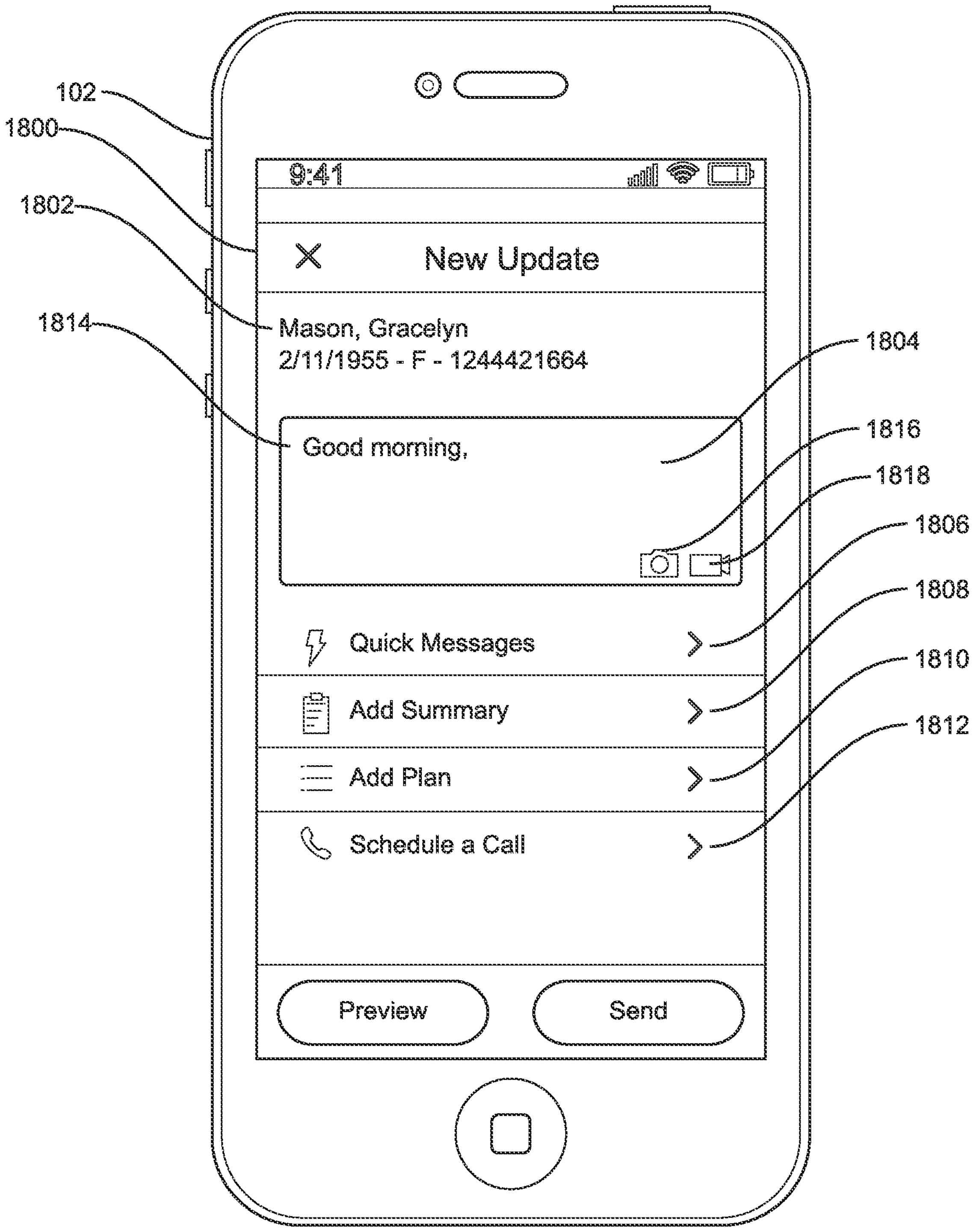
FIG. 18 illustrates an example of a generate new update screen displayed on the mobile device of the caregiver by the family communications application of FIG. 1.

FIG. 18 illustrates an example of a generate new update screen 1800 displayed on the mobile device 102 of the caregiver 12 by the family communications application 106. The generate new update screen 1800 is provided in response to the caregiver 12 selecting the new update icon 1512 on the family messaging screen 1500 of FIG. 15.

The generate new update screen 1800 displays information 1802 that identifies the patient 14 such as the patient's name, date of birth, sex, medical record number, and the like. The generate new update screen 1800 further displays a text field 1804 that can be filled with a message by the caregiver 12 selecting a message tab 1806. The generate new update screen 1800 further includes an add patient condition summary tab 1808, an add patient plan tab 1810, and a schedule call tab 1812. These features will be described in more detail below.

In some examples, the text field 1804 may automatically include a predefined introductory phrase 1814 such as "Good morning," or Good evening," which can be determined based on the location of the enrolled family member. Additionally, the text field 1804 can include a camera icon 1816 which allows the caregiver 12 to add a photograph to the update, and can include a video icon 1818 which allows the caregiver 12 to add a video to the update. The photograph and video can be of the patient 14, and can be taken by the caregiver 12 using the camera of the mobile device 102. Alternatively, a video of the patient's doctor providing an update on the patient's condition can be added to the update.

Figure 19:
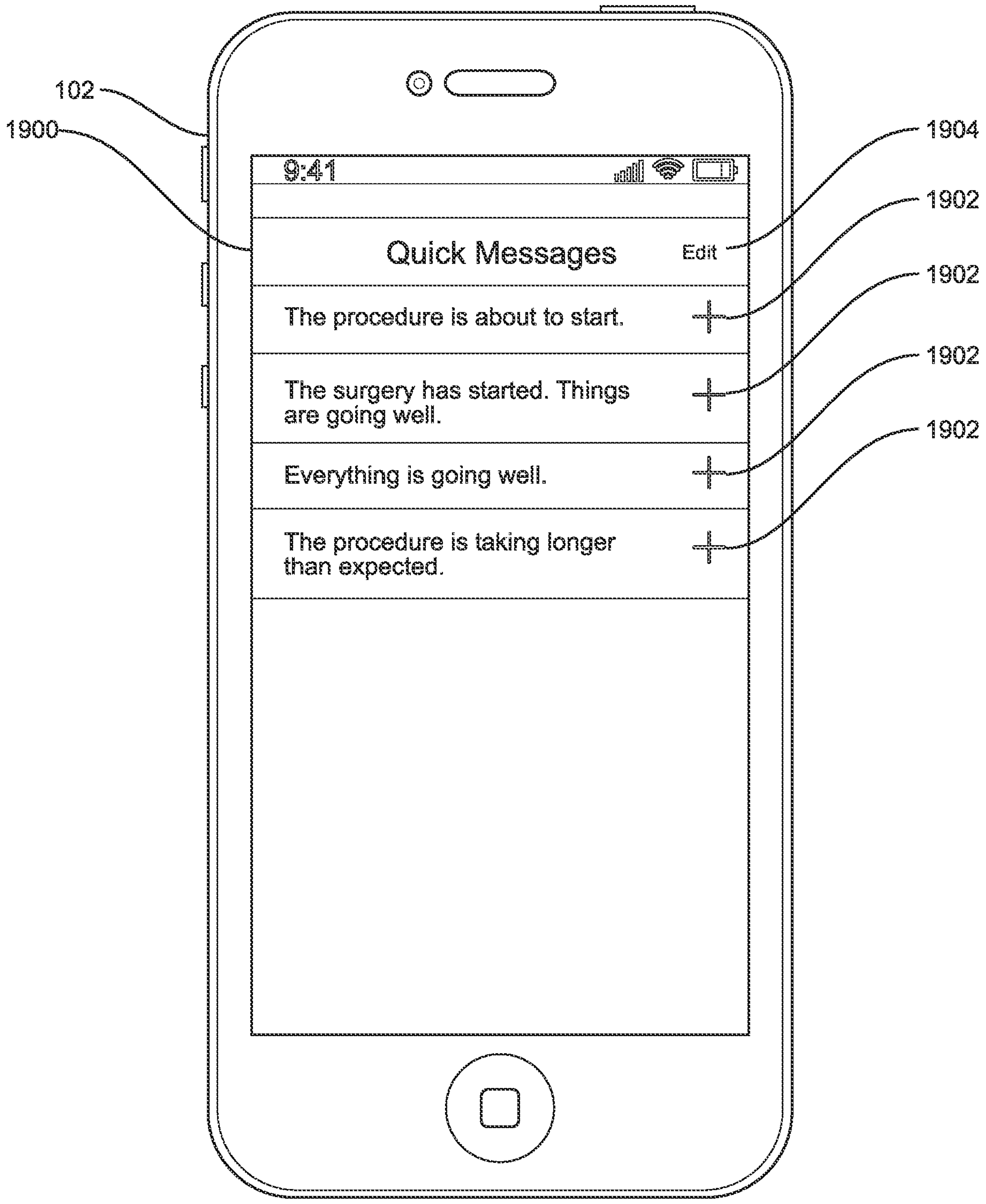
FIG. 19 illustrates an example of an add message screen generated on the mobile device of the caregiver by the family communications application of FIG. 1.

FIG. 19 illustrates an example of an add message screen 1900 generated on the mobile device 102 of the caregiver 12 by the family communications application 106. The add message screen 1900 is generated in response to the caregiver 12 selecting the message tab 1806 on the generate new update screen 1800. The add message screen 1900 can be used to perform the step 1702 of adding a message in operation 208 of managing patient updates.

As shown in FIG. 19, the add message screen 1900 includes a plurality of pre-generated messages 1902 that can be selected by the caregiver 12 for entry into the text field 1804 displayed in the generate new update screen 1800. The plurality of pre-generated messages 1902 can be based on the unit of the patient 14 that is identified from the patient enrollment in operation 204 and FIGS. 7-9, or can be based on the unit selected by the caregiver 12 in the unit selection screen 500 of FIG. 5. For example, the pre-generated messages 1902 for a med surg unit may include, without limitation, "The procedure is about to start", "The surgery has started. Things are going well.", "Everything is going well.", and "The procedure is taking longer than expected." The add message screen 1900 may display a variety of pre-generated messages based on the unit of the patient 14 such that these examples are not meant to be limiting.

In some examples, the caregiver 12 is prohibited from editing, deleting, or adding pre-generated messages that can be selected from the add message screen 1900. In such examples, the content and composition of the pre-generated messages are controlled by an authorized administrator to ensure that only approved pre-generated messages can be selected by the caregiver 12 for sending in an update to the family member 16 of the patient 14.

In other examples, such as the one shown in FIG. 19, the add message screen 1900 can include an edit icon 1904 that can be selected by the caregiver 12 to edit, delete, or add pre-generated messages 1902 for display and selection on the add message screen 1900. In such examples, the family communications application 106 allows flexibility for the caregiver 12 to edit the content and composition of the pre-generated messages based on their experience from working in clinical care environment 10, and from communicating with families.

Figure 20:
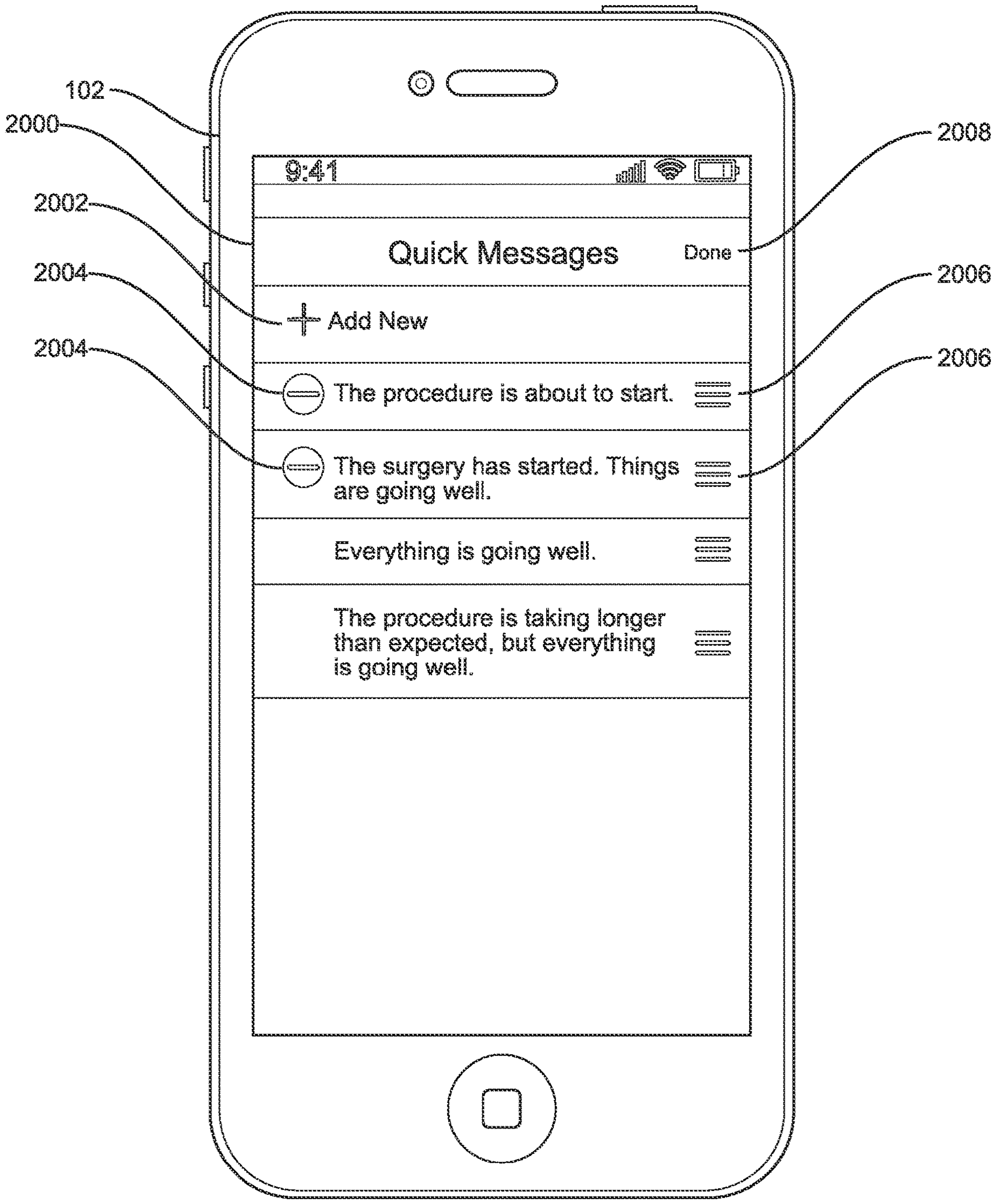
FIG. 20 illustrates an example of a modify pre-generated messages screen generated on the mobile device of the caregiver by the family communications application of FIG. 1.

FIG. 20 illustrates an example of a modify pre-generated messages screen 2000 that is generated on the mobile device 102 by the family communications application 106 in response to the caregiver 12 selecting the edit icon 1904 in the add message screen 1900. The modify pre-generated messages screen 2000 includes an add new icon 2002 for the caregiver 12 to add new pre-generated messages, and delete icons 2004 for the caregiver 12 to delete existing pre-generated messages. Additionally, the modify pre-generated messages screen 2000 includes edit icons 2006 that can be selected by the caregiver 12 to edit the pre-generated messages, and a done icon 2008 that can be selected to return to the add message screen 1900.

Figure 21:
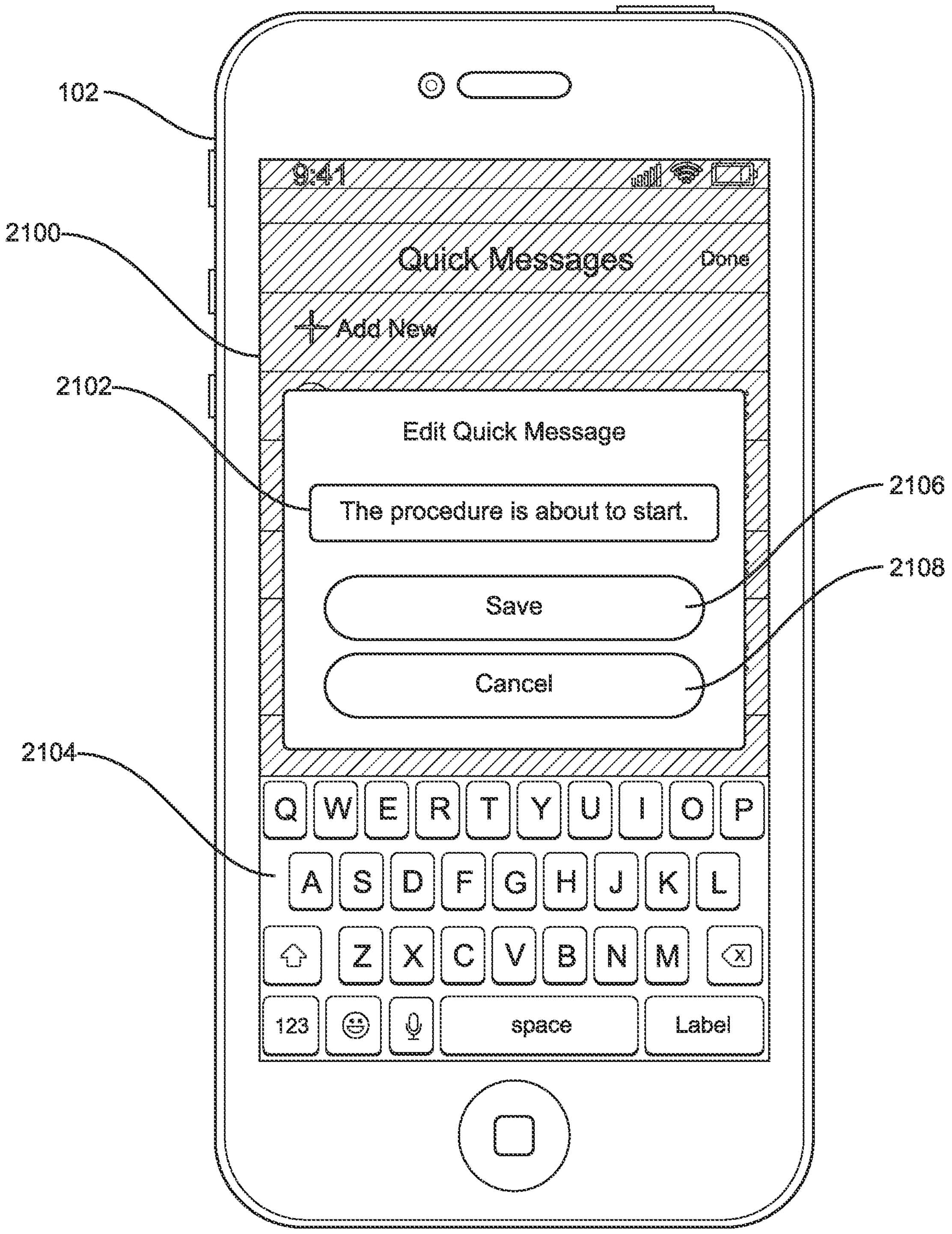
FIG. 21 illustrates an example of an edit pre-generated message screen generated on the mobile device of the caregiver by the family communications application of FIG. 1.

FIG. 21 illustrates an example of an edit pre-generated message screen 2100 generated on the mobile device 102 by the family communications application 106 in response to the caregiver 12 selecting an edit icon 2006 from the modify pre-generated messages screen 2000. The edit pre-generated message screen 2100 includes a keyboard 2104 for the caregiver 12 to edit the composition of the pre-generated message which is displayed in a text field 2102. The edit pre-generated message screen 2100 further includes a save icon 2106 for the caregiver 12 to save the edits to the pre-generated message, and a cancel icon 2108 for the caregiver 12 to return to the modify pre-generated messages screen 2000 shown in FIG. 20.

Figure 22:
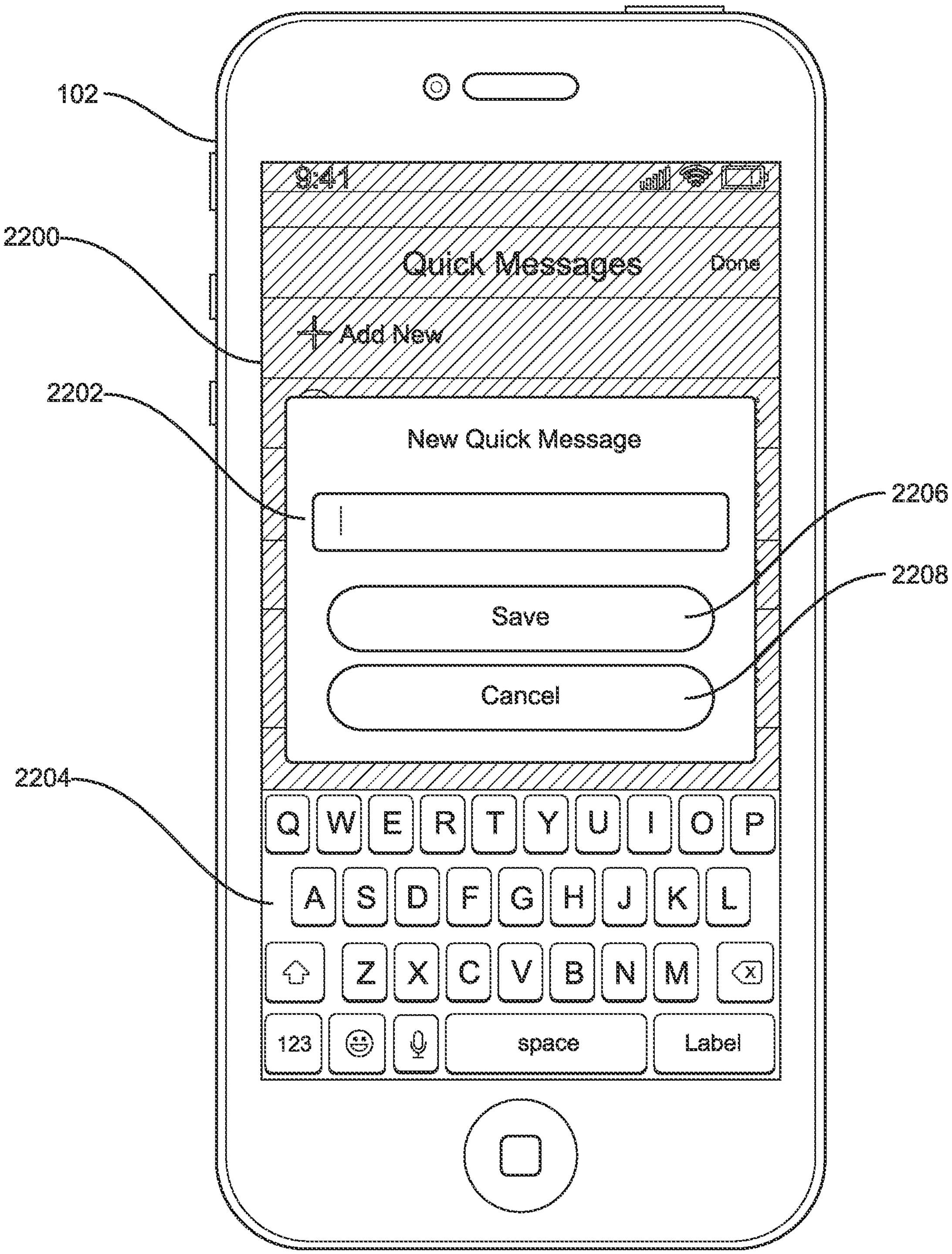
FIG. 22 illustrates an example of an add new pre-generated message screen generated on the mobile device of the caregiver by the family communications application of FIG. 1.

FIG. 22 illustrates an example of an add new pre-generated message screen 2200 generated on the mobile device 102 by the family communications application 106 in response to the caregiver 12 selecting the add new icon 2002 from the modify pre-generated messages screen 2000. The add new pre-generated message screen 2200 includes a keyboard 2204 for the caregiver 12 to write a new pre-generated message which is displayed in a text field 2202. The add new pre-generated message screen 2200 further includes a save icon 2206 for the caregiver 12 to save the new pre-generated message, and a cancel icon 2208 for the caregiver 12 to return to the modify pre-generated messages screen 2000 shown in FIG. 20.

Figure 23:
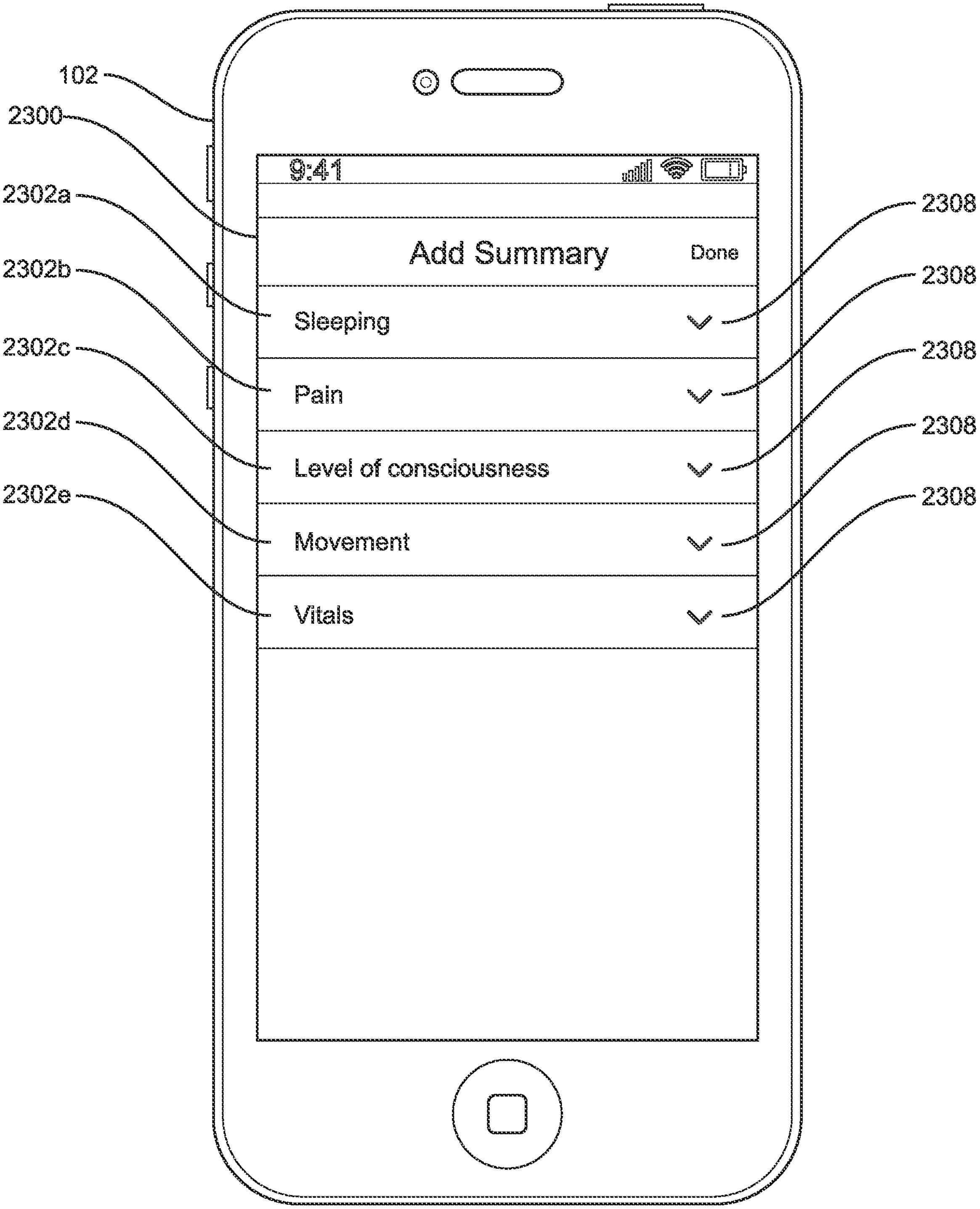
FIG. 23 illustrates an example of an add patient condition summary screen generated on the mobile device of the caregiver by the family communications application of FIG. 1.

FIG. 23 illustrates an example of an add patient condition summary screen 2300 generated on the mobile device 102 by the family communications application 106. The add patient condition summary screen 2300 is generated in response to the caregiver 12 selecting the add patient condition summary tab 1808 on the generate new update screen 1800. The add patient condition summary screen 2300 can be used to perform the step 1704 of adding a patient condition summary in the operation 208 of managing patient updates.

The add patient condition summary screen 2300 includes a list of predefined patient condition summaries 2302*a*-2302*e* that can be based on the unit of the patient 14 identified from the patient enrollment, or can be based on the unit selected by the caregiver 12 in the unit selection screen 500 of FIG. 5. The predefined patient condition summaries 2302*a*-2302*e* can be unit specific templates that are selectable by the caregiver 12 to add to the update.

Illustrative examples of predefined patient condition summaries can include, without limitation, sleeping, pain level, level of consciousness, movement, and vital signs, and the like. The caregiver 12 can select a predefined patient condition summary 2302*a*-2302*e* to include a summary of the patient's condition in the update. For example, the caregiver 12 can select an icon 2308 to expand a list of selectable predefined options for each of the predefined patient condition summaries 2302*a*-2302*e* on the add patient condition summary screen 2300.

Figure 24:
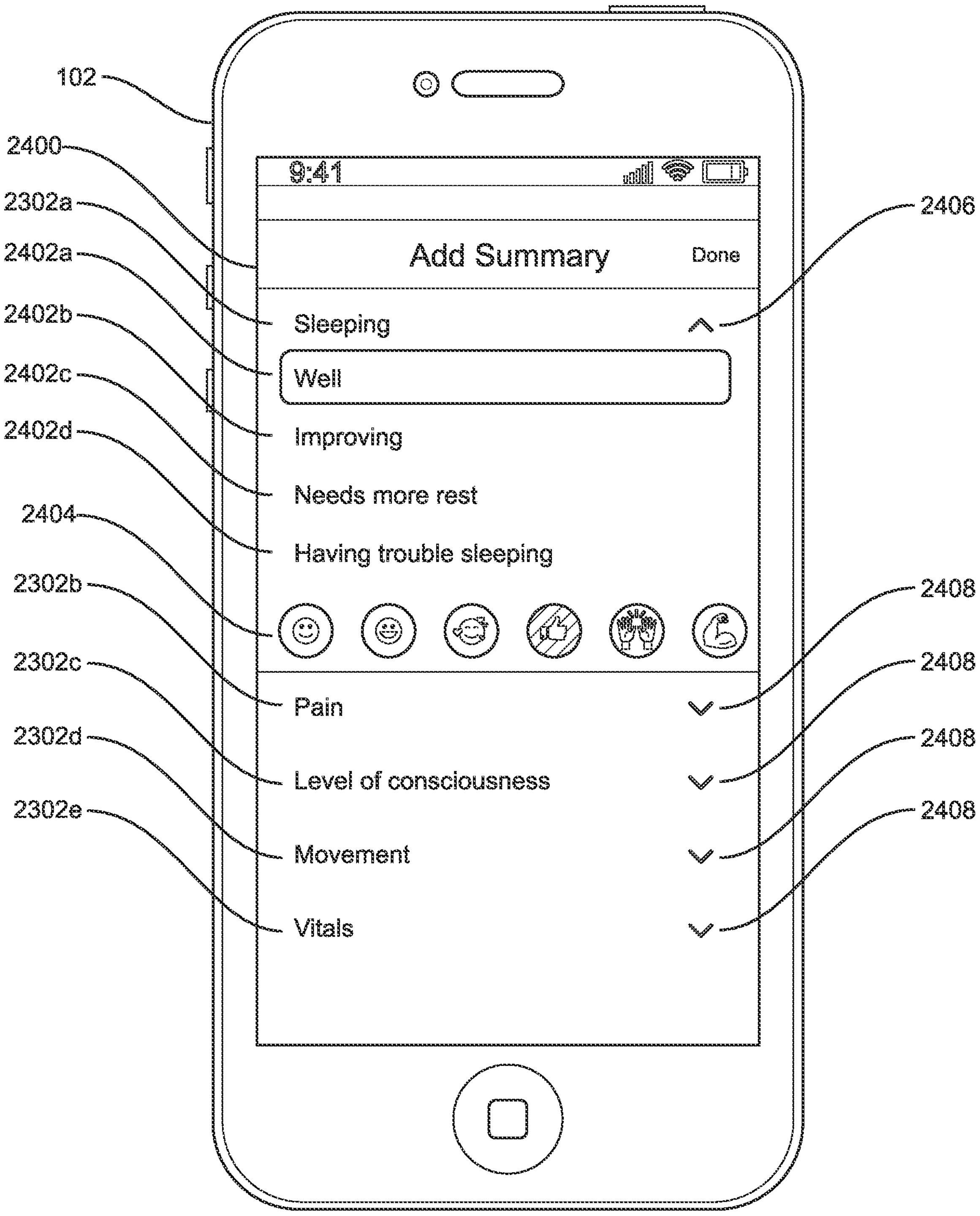
FIG. 24 illustrates an example of an add patient condition summary screen generated on the mobile device of the caregiver by the family communications application of FIG. 1.

FIG. 24 illustrates an example of an add patient condition summary screen 2400 generated on the mobile device 102 of the caregiver 12 by the family communications application 106 in response to the caregiver 12 selecting the icon 2308 for the predefined patient condition summary 2302*a*. In this example, the predefined patient condition summary 2302*a* is for "Sleeping". A plurality of predefined options 2402*a*-2402*d* are displayed below the predefined patient condition summary 2302*a* for the caregiver 12 to select. In the example shown, the predefined option 2402*a* "Well" is selected. Additional predefined options that can be selected may include "Improving", "Needs more rest", "Having trouble sleeping", and the like.

In some examples, a plurality of emojis 2404 can be displayed below the predefined patient condition summary 2302*a*. An emoji from the plurality of emojis 2404 can be selected by the caregiver 12 to add to the predefined options 2402*a*-2402*d* selected for the predefined patient condition summary 2302*a*. In the example shown in FIG. 24, a thumbs-up emoji is selected. The plurality of emojis 2404 allow the caregiver 12 to customize the update to make it more family friendly and sincere. The caregiver 12 can select an icon 2406 to save the selection of the predefined option 2402*a* and the thumbs-up emoji, and to collapse the predefined options 2402*a*-2402*d* and plurality of emojis 2404 for the predefined patient condition summary 2302*a*.

Below the plurality of emojis 2404, the predefined patient condition summaries 2302*b*-2302*e* are displayed. The caregiver 12 can select an icon 2408 to expand predefined options and emojis for each of the predefined patient condition summaries 2302*b*-2302*e*.

Figure 25:
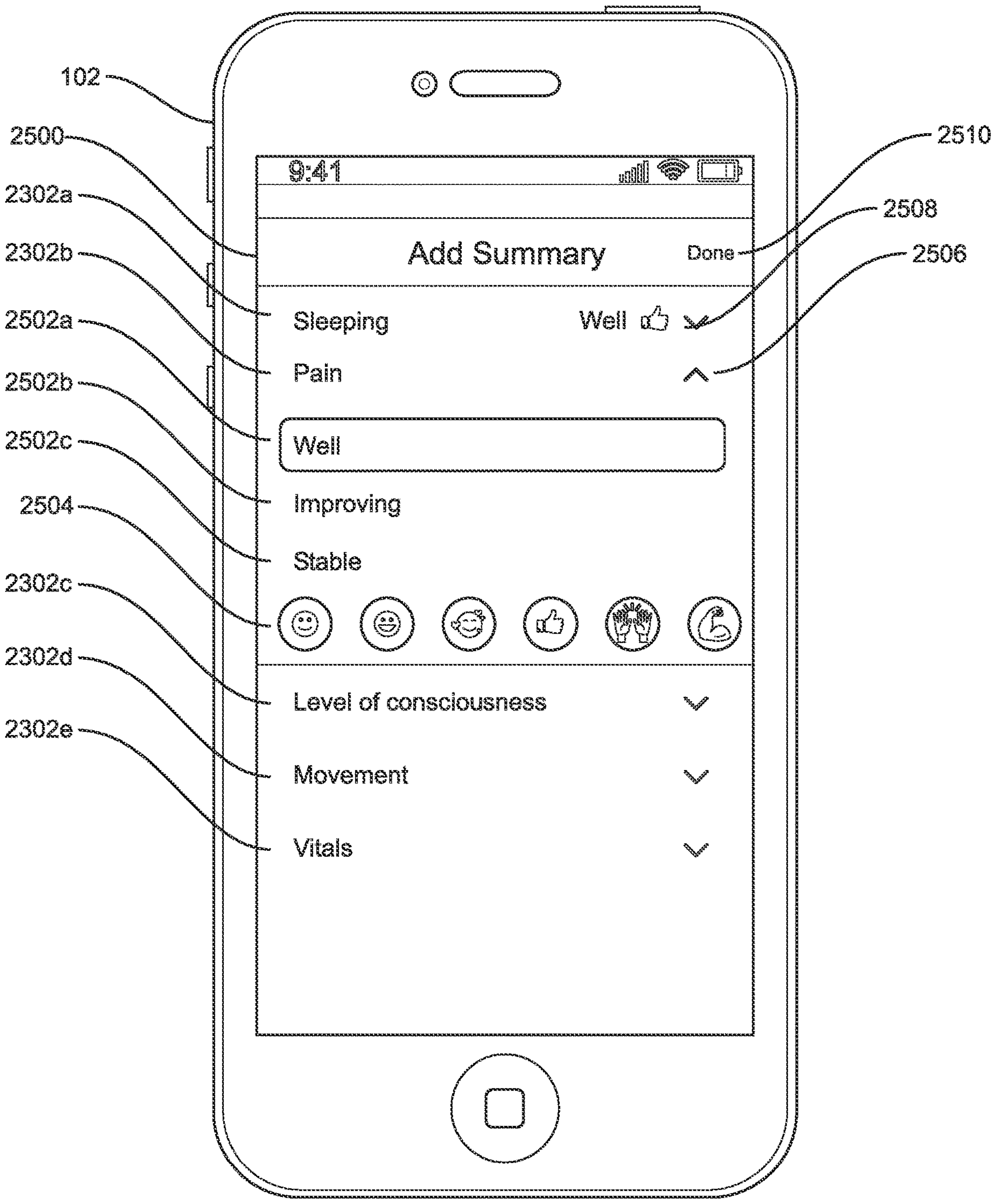
FIG. 25 illustrates an example of an add patient condition summary screen generated on the mobile device of the caregiver by the family communications application of FIG. 1.

FIG. 25 illustrates an example of another add patient condition summary screen 2500 generated on the mobile device 102 of the caregiver 12 by the family communications application 106 in response to the caregiver 12 selecting the icon 2408 to expand predefined options and emojis for the predefined patient condition summary 2302*b*. In this example, the predefined patient condition summary 2302*b* is for "Pain". A plurality of predefined options 2502*a*-2502*c* and a plurality of emojis 2504 are displayed below the predefined patient condition summary 2302*b* for the caregiver 12 to select for this predefined patient condition summary.

The caregiver 12 can select an icon 2506 to save a selection from the predefined options 2502*a*-2502*c* and the plurality of emojis 2504, and to collapse the predefined options 2502*a*-2502*c* and plurality of emojis 2504 for the predefined patient condition summary 2302*b*. In FIG. 25, "Well" and a thumbs-up emoji selection 2508 are displayed next to the predefined patient condition summary 2302*a*. This combination of predefined option and emoji were selected from the plurality of predefined options 2402*a*-2402*d* and the plurality of emojis 2404 shown in the add patient condition summary screen 2400 of FIG. 24. When the caregiver 12 is done with adding patient condition summaries from the patient condition summary screen 2500, the caregiver 12 can select the done icon 2510 to return to the generate new update screen 1800.

Figure 26:
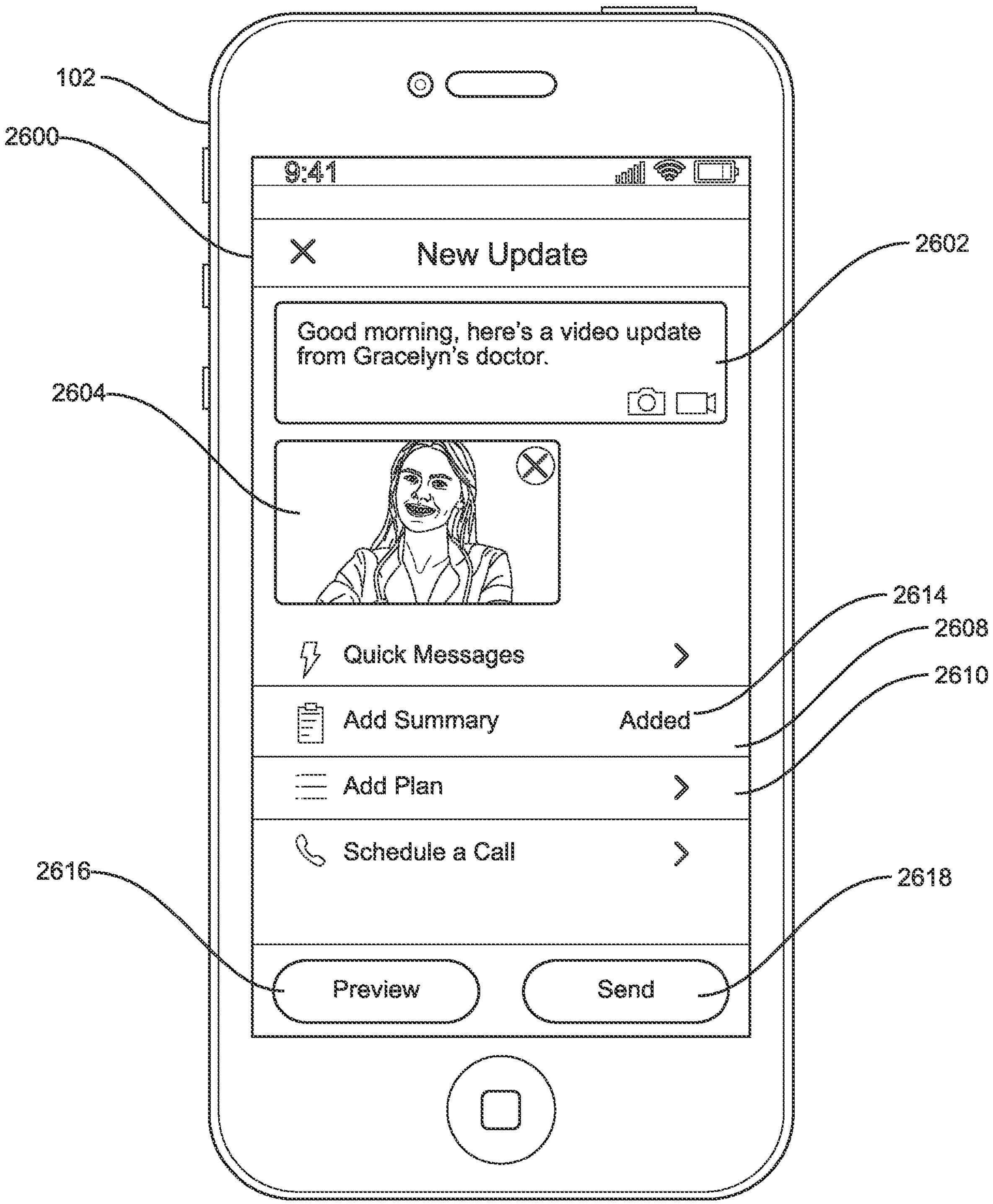
FIG. 26 illustrates an example of a generate new update screen displayed after a patient condition summary has been added to the update in FIG. 25.

FIG. 26 illustrates an example of a generate new update screen 2600 displayed after the patient condition summaries have been added to the update. As shown in FIG. 26, a text field 2602 includes a message such as "Good morning, here's a video update from Gracelyn's doctor" and a video 2604 of the patient's doctor has been added to the update. FIG. 26 further shows that an identifier 2614 has been added to the add patient condition summary tab 2608 to inform the caregiver 12 that the one or more patient condition summaries have been added to the update.

The generate new update screen 2600 includes a preview icon 2616 that can be selected by the caregiver to view the update, and a send icon 2618 that can be selected by the caregiver to send the update to the family member 16 as presently composed. Additionally, the generate new update screen 2600 includes an add patient plan tab 2610 to add additional details regarding the patient's plans to the update. This feature will be described next.

Figure 27:
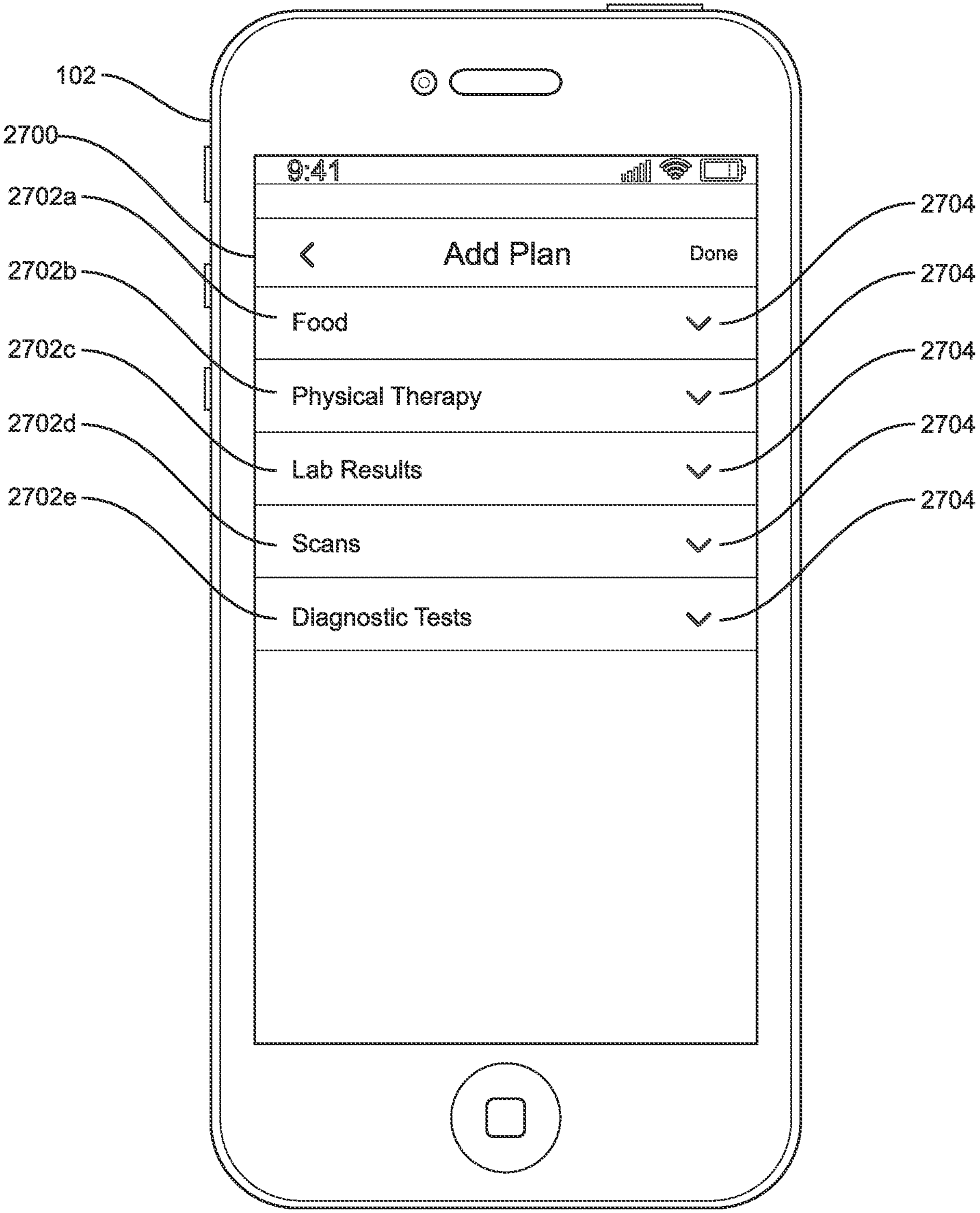
FIG. 27 illustrates an example of an add patient plan screen generated on the mobile device of the caregiver by the family communications application of FIG. 1.

FIG. 27 illustrates an example of an add patient plan screen 2700 generated on the mobile device 102 by the family communications application 106. The add patient plan screen 2700 is generated in response to the caregiver 12 selecting the add patient plan tab 2610 from the generate new update screen 2600 of FIG. 26. The add patient plan screen 2700 can be used to perform the step 1706 of adding a patient plan in the operation 208 of managing patient updates.

The add patient plan screen 2700 includes a plurality of predefined patient plans 2702*a*-2702*e* that can be based on the unit of the patient 14 identified from the patient enrollment, or can be based on the unit selected by the caregiver 12 in the unit selection screen 500 of FIG. 5. Accordingly, the predefined patient plans 2702*a*-2702*e* can be unit specific templates that are selectable by the caregiver 12 to add to the update. Examples of patient plans can include, without limitation, a food plan, a physical therapy plan, labs, scans, diagnostic tests, and the like. The caregiver 12 can select an icon 2704 to expand a list of predefined options for each of the plurality of predefined patient plans 2702*a*-2702*e*.

Figure 28:
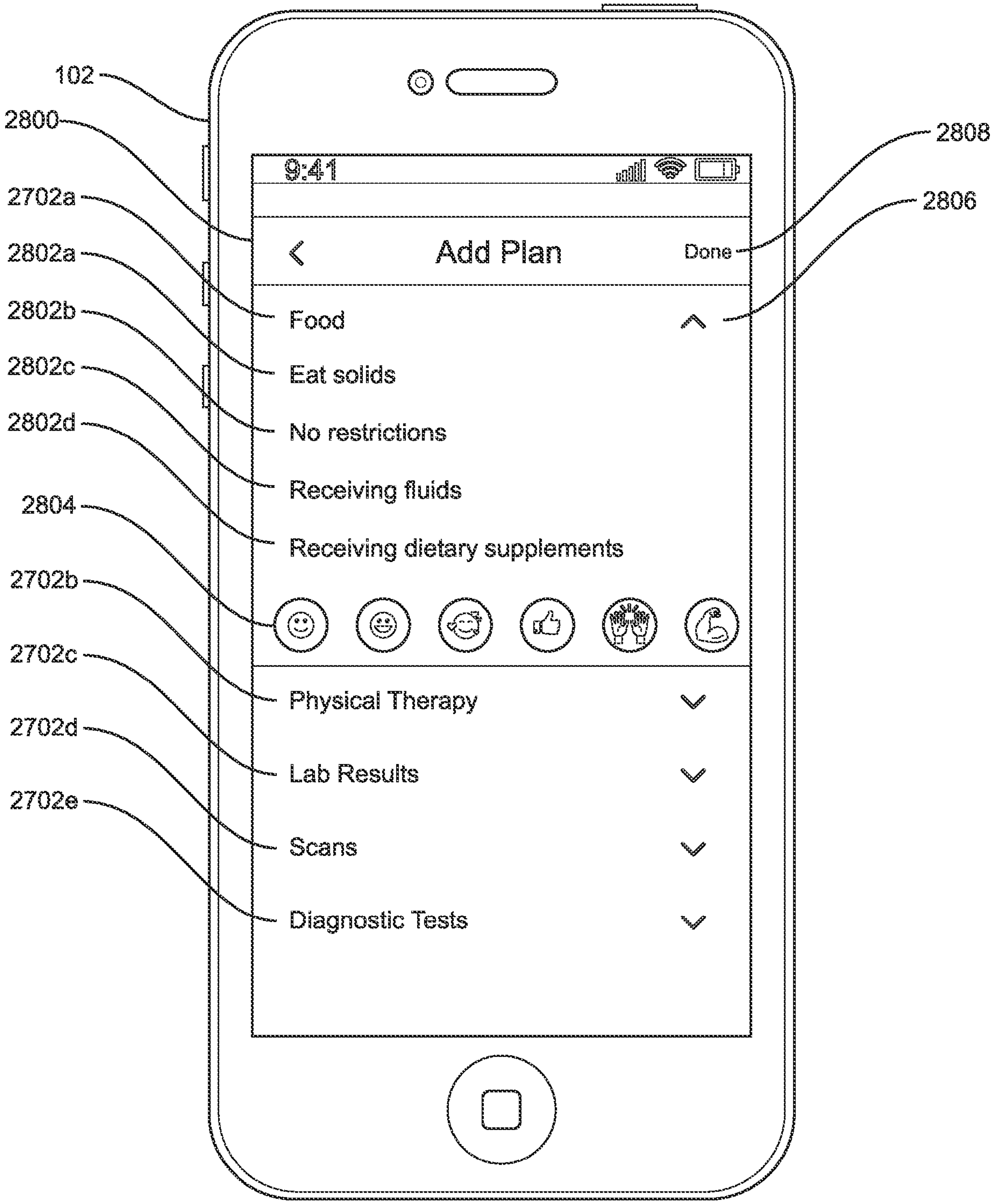
FIG. 28 illustrates an example of another add patient plan screen generated on the mobile device of the caregiver by the family communications application of FIG. 1.

FIG. 28 illustrates an example of an add patient plan screen 2800 generated on the mobile device 102 of the caregiver 12 by the family communications application 106 in response to the caregiver 12 selecting the icon 2704 to expand predefined options for the predefined patient plan 2702*a*. In this example, the predefined patient plan 2702*a* is for "Food". A plurality of predefined options 2802*a*-2802*d* and a plurality of emojis 2804 are displayed below the predefined patient plan 2702*a* for the caregiver 12 to select for adding to the update. In this example, the predefined options 2802*a*-2802*d* include "Eat solids", "No restrictions", "Receiving fluids", and "receiving dietary supplements". Additional predefined options may be provided.

As shown in FIG. 28, the caregiver 12 can select an icon 2806 to save a selection from the predefined options 2802*a*-2802*d* and the plurality of emojis 2804, and to collapse the predefined options and plurality of emojis for the predefined patient plan 2702*a*. When the caregiver 12 is done with adding the patient plans from the add patient plan screen 2800, the caregiver 12 can select the done icon 2808 to return to the generate new update screen 2600.

Figure 29:
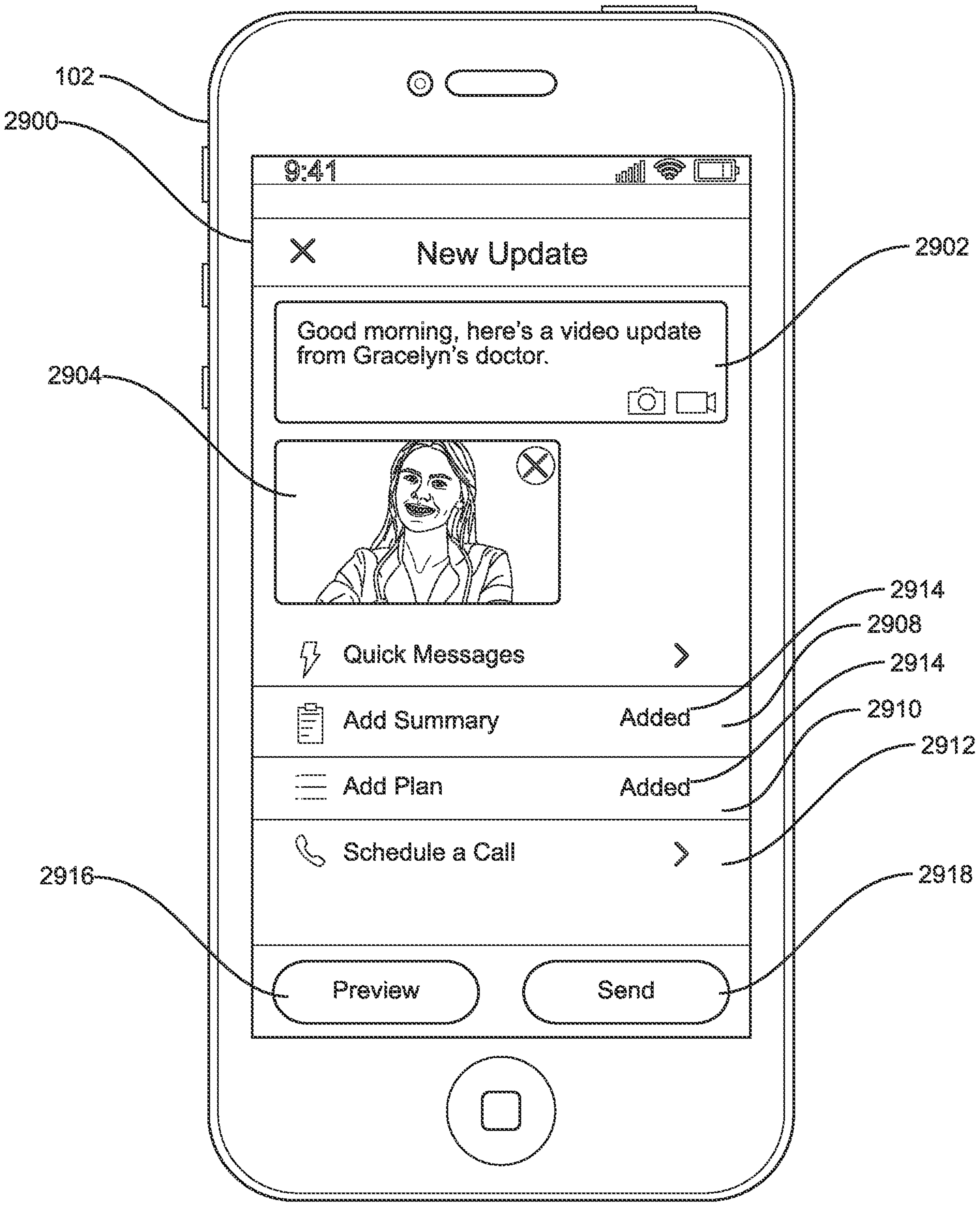
FIG. 29 illustrates an example of a generate new update screen generated after the patient condition summaries and patient plans have been added to the update from FIGS. 23-28.

FIG. 29 illustrates an example of a generate new update screen 2900 that is displayed on the mobile device 102 after the patient condition summaries and patient plans have been added to the update. A text field 2902 includes a message such as "Good morning, here's a video update from Gracelyn's doctor" and a video 2904 of the patient's doctor has been added to the update. FIG. 29 further shows that identifiers 2914 have been added to the add patient condition summary tab 2908 and to the add patient plan tab 2910 to inform the caregiver 12 that the one or more patient conditions and one or more patient plans have been added to the update. The generate new update screen 2900 further includes a preview icon 2916 that can be selected by the caregiver to view the update as presently composed, and a send icon 2918 that can be selected by the caregiver to send the update to the family member 16 as presently composed. Additionally, the generate new update screen 2900 includes a schedule call tab 2912 to add a time for calling the family member 16 to discuss the patient's condition. This feature will be described next.

Figure 30:
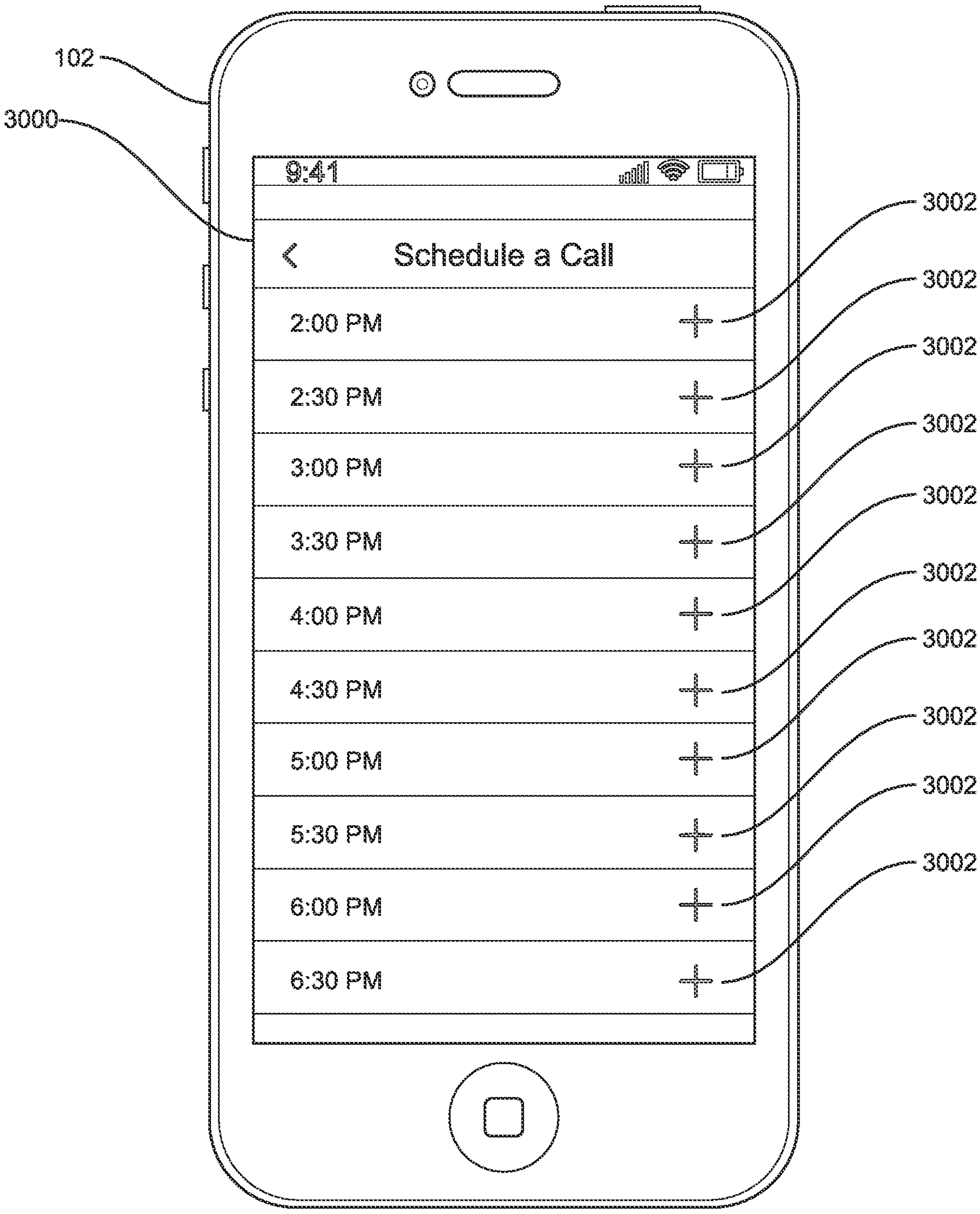
FIG. 30 illustrates an example of a schedule call screen generated on the mobile device of the caregiver by the family communications application of FIG. 1.

FIG. 30 illustrates an example of a schedule call screen 3000 generated on the mobile device 102 of the caregiver 12 by the family communications application 106. The schedule call screen 3000 is generated in response to the caregiver 12 selecting the schedule call tab 2912 from the generate new update screen 2900 of FIG. 29. The schedule call screen 3000 can be used to perform the step 1708 of adding a time to schedule a call with the family member 16 of the patient 14 in the operation 208 of managing patient updates. As shown in FIG. 30, the schedule call screen 3000 includes a plurality of times 3002 from which the caregiver 12 can select to include in the update to let the family member 16 know when they can expect a call from the caregiver 12 or from the doctor of the patient 14 to discuss the patient's condition.

Figure 31:
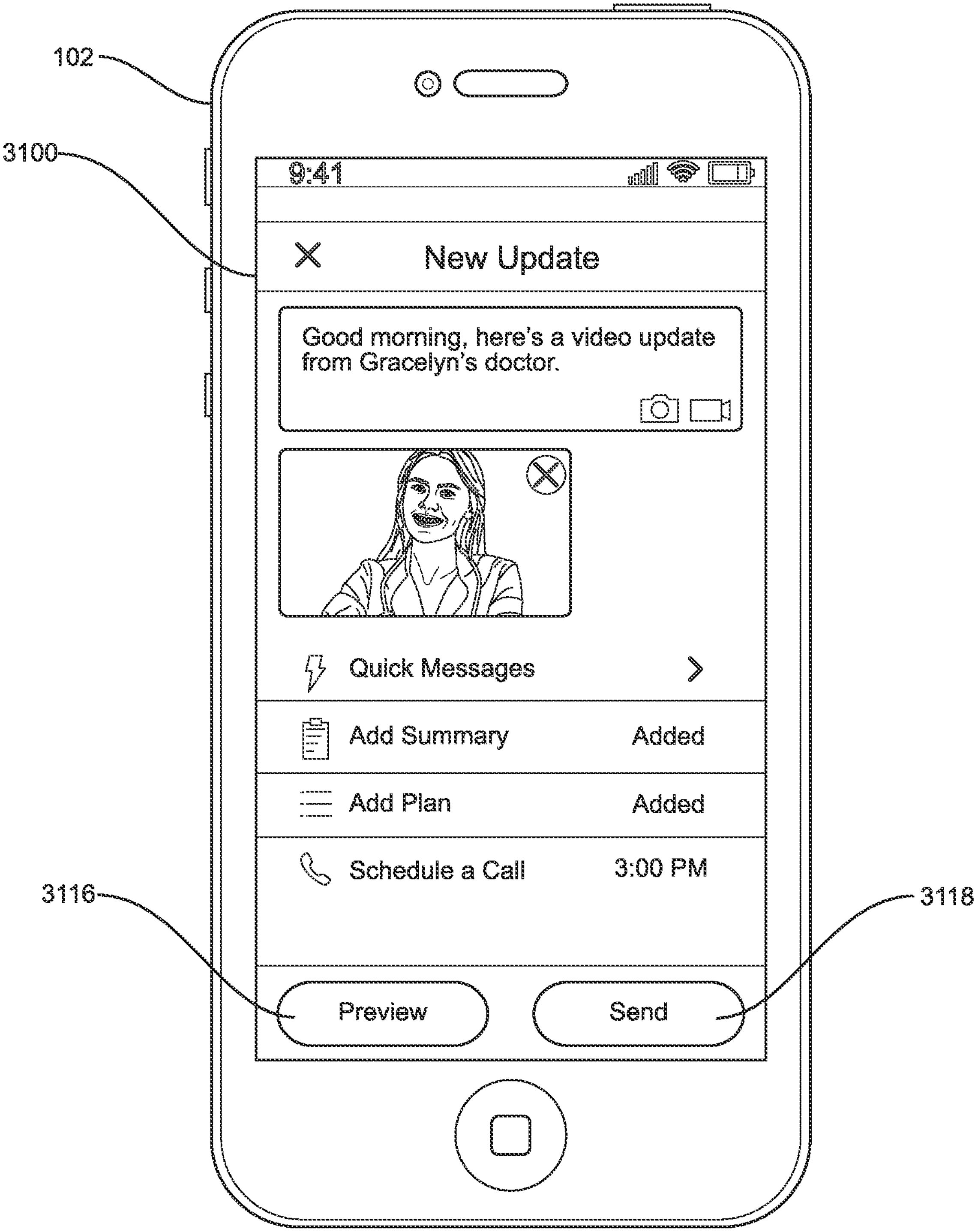
FIG. 31 illustrates an example of a generate new update screen generated after the message, patient condition summary, patient plan, and scheduled call have been added to the update from FIGS. 23-30.

FIG. 31 illustrates an example of a generate new update screen 3100 displayed after the patient condition summaries, patient plans, and scheduled call time have been added to the update. In the example shown in FIG. 31, a 3:00 pm time has been selected for calling the family member 16. The generate new update screen 3100 includes a preview icon 3116 that can be selected by the caregiver to view a preview of the update, and a send icon 3118 that can be selected by the caregiver to send the update to the family member 16.

Figure 32:
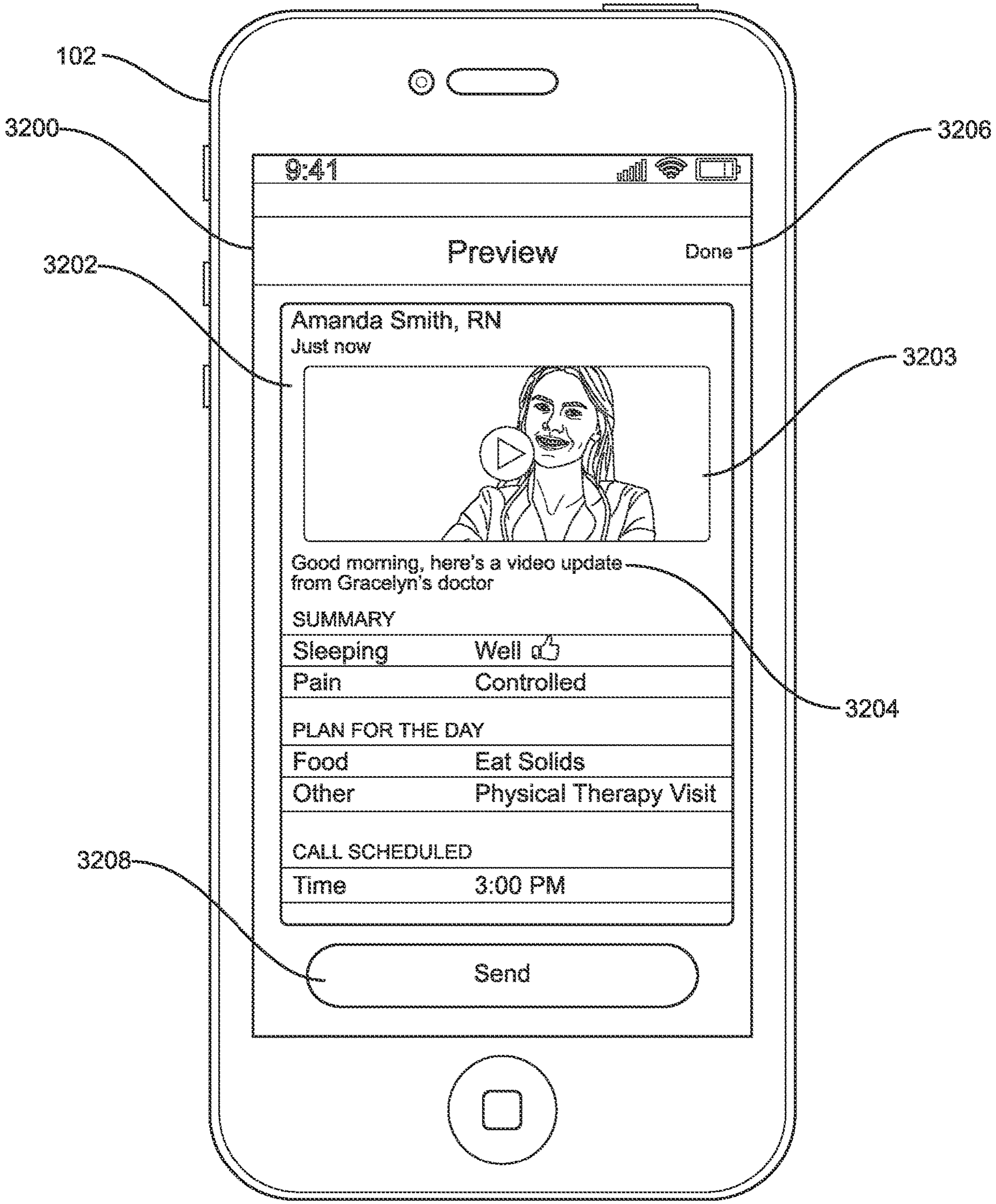
FIG. 32 illustrates an example of an update preview screen generated on the mobile device of the caregiver by the family communications application of FIG. 1.

FIG. 32 illustrates an example of an update preview screen 3200 generated on the mobile device 102 by the family communications application 106 in response to the caregiver 12 selecting the preview icon 3116 from the generate new update screen 3100. In the example shown in FIG. 32, the update preview screen 3200 includes an update 3202 that is generated in accordance with the steps 1702-1708 of FIG. 17, and the screens shown in FIGS. 18-31.

The update 3202 includes a video 3203 from the patient's doctor, and a message 3204 stating "Good morning, here's a video update from Gracelyn's doctor." The update 3202 identifies that the patient 14 is sleeping well and their pain is controlled, and their plans for the day are to eat solids and have a physical therapy visit. The update 3202 further includes a 3:00 pm time for the family member 16 to call the caregiver 12 to discuss the condition of the patient 14. If the caregiver 12 is not satisfied with the update 3202, the caregiver 12 can select the edit icon 3206 to return to the generate new update screen 3100 to edit the update 3202. When the caregiver 12 is satisfied with the update 3202, the caregiver can select the send icon 3208 to send the update 3202 to the family member 16. The update 3202 received by the mobile device 102 of the family member 16 will be described in more detail below with reference to FIGS. 48 and 49.

In some examples, the update 3202 is generated and sent in accordance with steps 1702-1712 of FIG. 17, and using the screens shown in FIGS. 18-32, during rounding. For example, the caregiver 12 can enter a room of the patient 14 to perform rounding (such as to take vital signs, administer medications, and the like) and can generate the update 3202 while in the room with the patient 14 to update the family member 16 on the status of the patient 14.

In some further examples, steps 1702-1712 are integrated into the rounding. For example, the list of predefined patient condition summaries 2302*a*-2302*e* (see FIG. 23) and the predefined patient plans 2702*a*-2702*e* (see FIG. 27) can be templates that are filled as part of the rounding performed by the caregiver 12 such that the caregiver 12 does not need to separately add the patient condition summary (i.e., step 1704) or the add patient plan (i.e., step 1706) but rather this information is pulled from the patient's electronic medical record (EMR) while it is being updated by the caregiver 12 during rounding. Thus, at least some parts of the update 3202 are automated, thereby reducing the workload on the caregiver 12 to generate the update 3202. In some examples, the information that is pulled from the patient's EMR is converted or translated into a format and phraseology that is family friendly and that can be more easily understood.

In some further examples, the family communications application 106 allows the caregiver 12 to call or videocall the family member 16 while the caregiver 12 is rounding inside the patient's room. Thus, the family communications application 106 can be used to implement family centered rounding to include the family in the patient rounding. This can be especially helpful for family members 16 who are remotely located far away from the patient 14.

In some further examples, the family communications application 106 can be integrated with patient-centric chat rooms such as those that are described in U.S. Provisional Patent Application No. 63/109,464, titled Managing Caregiver Messages, filed on Nov. 4, 2020, the entirety of which is hereby incorporated by reference. For example, the patient-centric chat rooms can be configured with a link to send an update to the family of the patient using the family communications application 106, and/or can be configured with a link to call a family member of the patient by acquiring the family member's contact information from the family communications application 106. Additionally, the patient-centric chat rooms can be configured to provide two-way communications between caregivers and patient families by integrating information acquired from the family communications application 106. In some further examples, patients and patient families can communicate with the caregivers post-discharge via communications platforms that integrate with the family communications application 106.

In some examples, a patient communications platform that is intended for communications between a patient and one or more caregivers can be integrated with the family communications application 106 such that a patient who uses the patient communications platform to communicate with the one or more caregivers can also communicate with their family. In some instances, the integration with the family communications application 106 allows the patient to use the patient communications platform to call, videocall, or message their family members who are enrolled in the family communications application 106.

Figure 33:
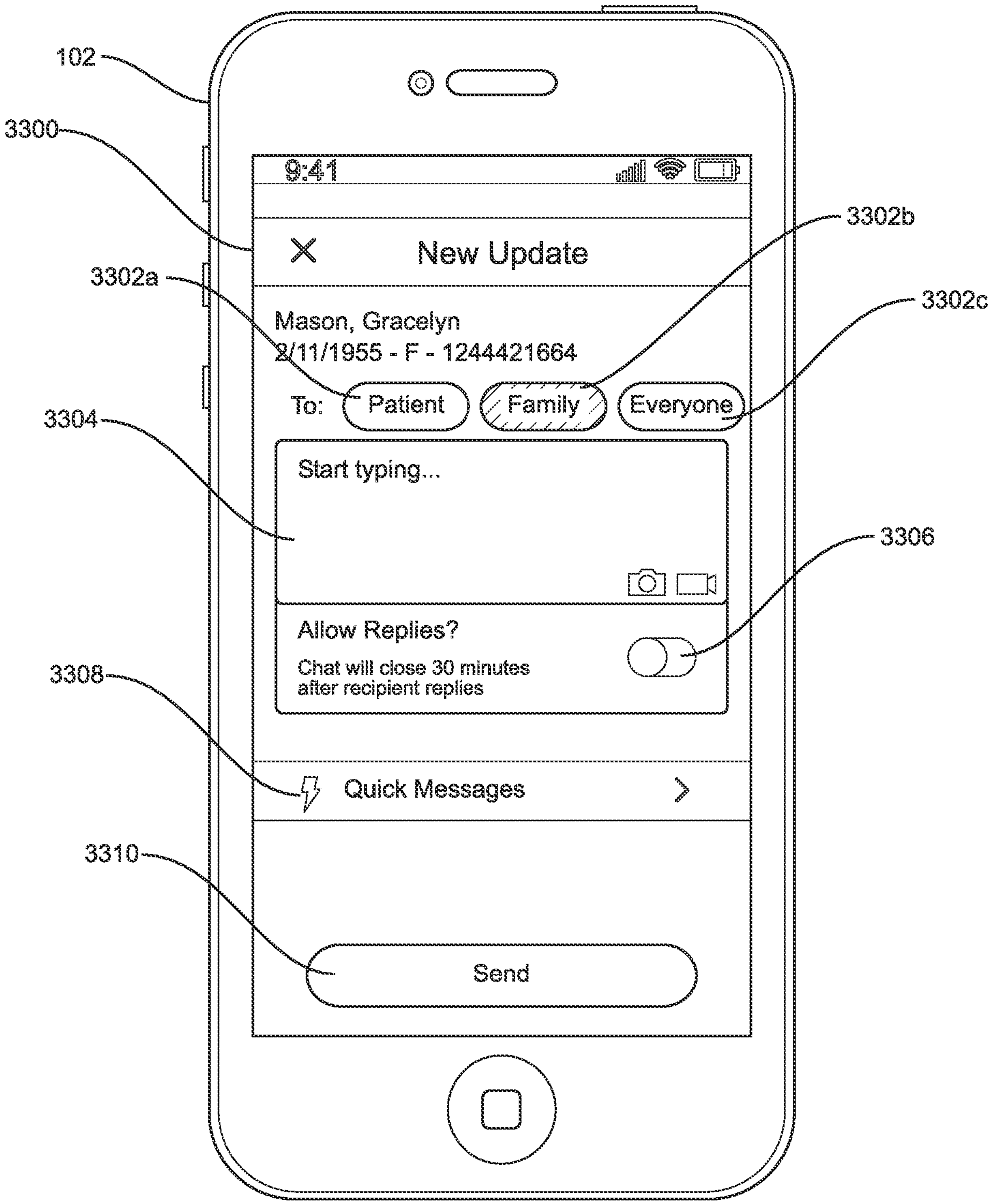
FIG. 33 illustrates another example of a generate new update screen generated on the mobile device of the caregiver by the family communications application of FIG. 1.

FIG. 33 illustrates another example of a generate new update screen 3300. In this example, the update screen 3300 includes options 3302*a*-3302*c* for the caregiver 12 to select persons to receive the update generated by the caregiver 12. For example, the caregiver 12 can select an option 3302*a* to send the update to the patient, an option 3302*b* to send the update to the family of the patient, or an option 3302*c* to send the update to everyone (e.g., both the patient and their family). In this example, the patient 14 is a user of the family communications application 106 such that the patient 14 can also receive the updates from the caregiver 12.

Figure 34:
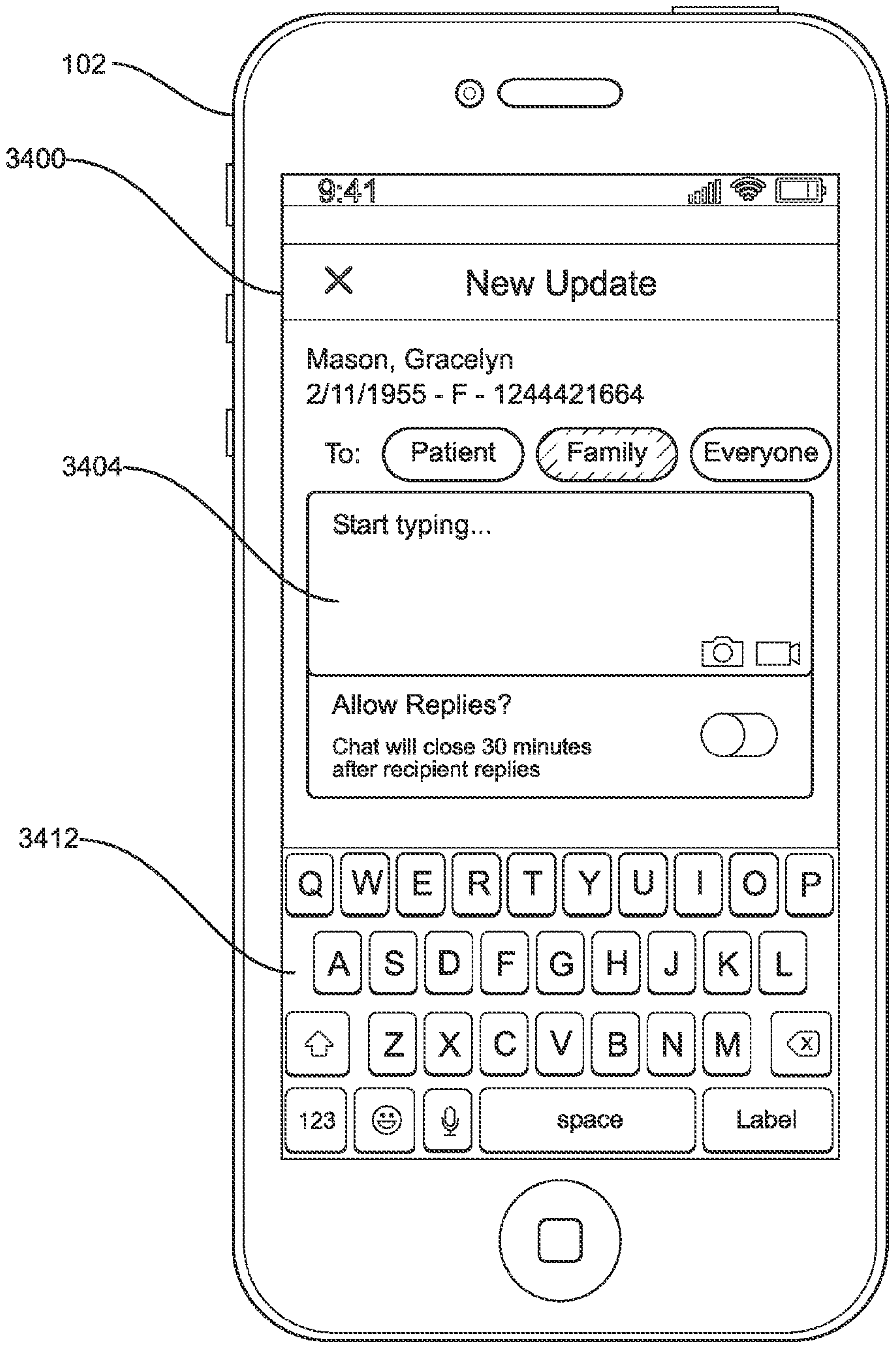
FIG. 34 illustrates another example of a generate new update screen generated on the mobile device of the caregiver by the family communications application of FIG. 1, the generate new update screen includes a keyboard for a caregiver to type a customized message.

The generate new update screen 3300 includes a text box 3304 where the caregiver 12 can type a customized message for a new update to be sent to the persons selected from options 3302*a*-3302*c*. FIG. 34 illustrates another example of a generate new update screen 3400 that includes a keyboard 3412 that the caregiver 12 can use to type the customized message into the text box 3404. Referring back to FIG. 33, the caregiver 12 can alternatively select an icon 3308 to add a pre-generated message to the new update (see examples shown in FIG. 19).

The generate new update screen 3300 further includes an icon 3306 that can be toggled between allowing replies to the update or blocking replies to the update. In FIG. 33, the icon 3306 is toggled to the left to block replies to the update.

Figure 35:
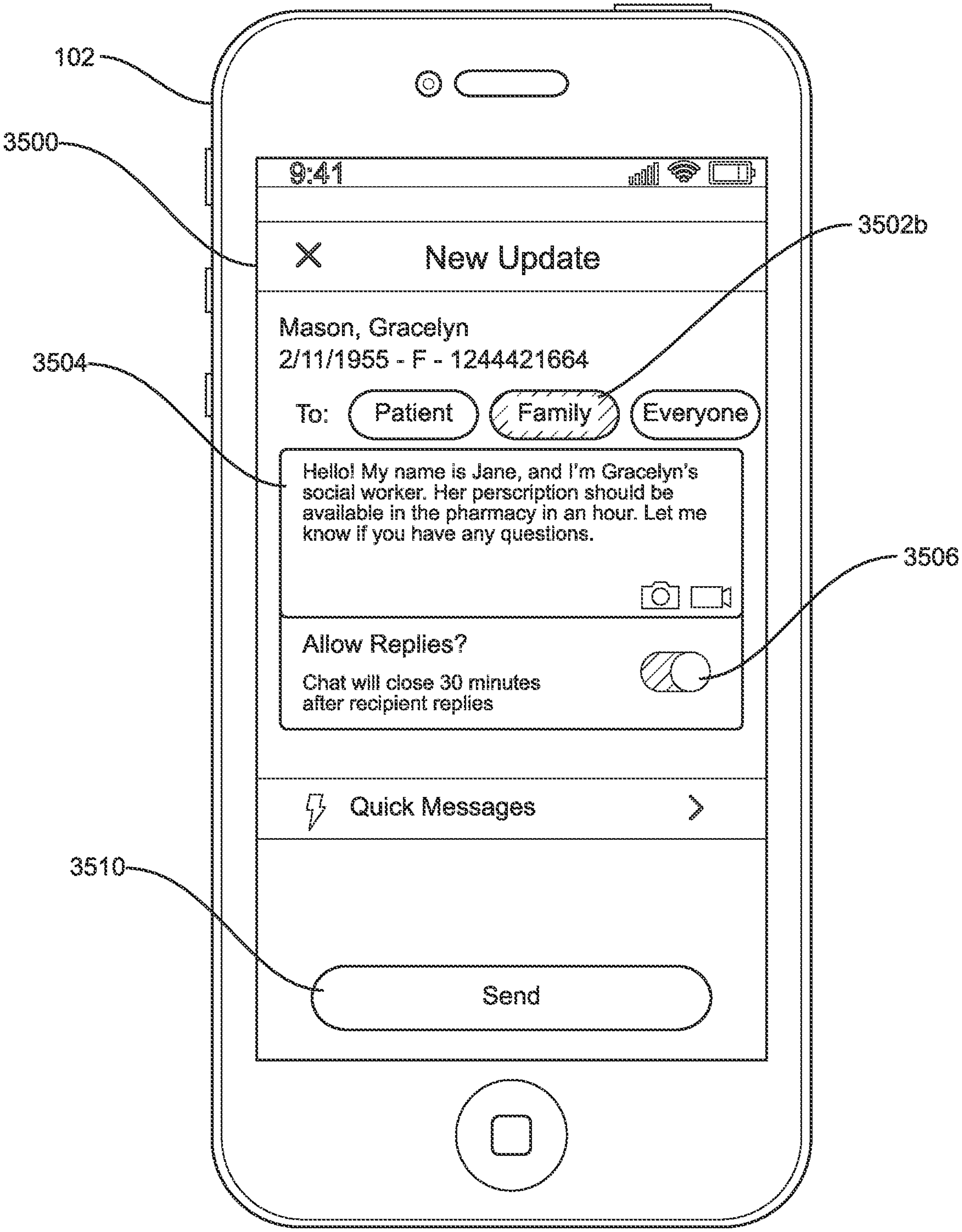
FIG. 35 illustrates another example of a generate new update screen generated on the mobile device of the caregiver by the family communications application of FIG. 1, the generate new update screen includes an icon toggled to allow replies to an update.

FIG. 35 illustrates another example of a generate new update screen 3500 in which an icon 3506 is toggled to the right to allow replies to the update. In this example, the family communications application 106 enables two-way communications between the caregiver 12, the patient 14, and the family members 16. As further shown in FIG. 35, the option 3502*b* to send the update to the family of the patient is selected, and the text box 3504 is populated with a customized message "Hello! My name is Jane, and I'm Gracelyn's social worker. Her prescription should be available in the pharmacy in an hour. Let me know if you have any questions." When the update is completed on the generate new update screen 3500, the caregiver 12 can select the send icon 3510 to send the update to the family of the patient 14.

Figure 36:
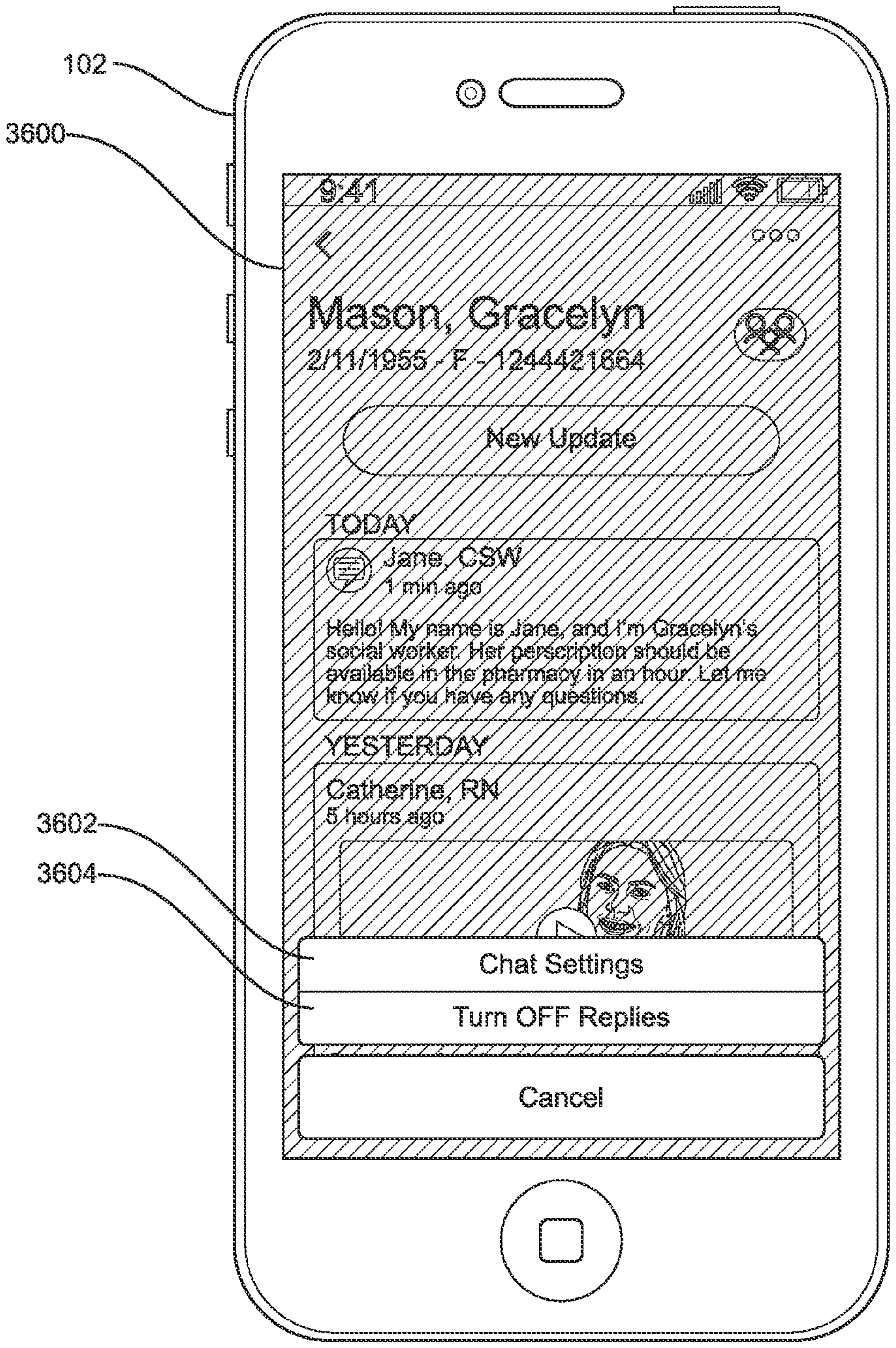
FIG. 36 illustrates another example of a user interface generated on the mobile device of the caregiver by the family communications application of FIG. 1, the user interface includes a chat settings pop-up.

FIG. 36 illustrates another example of a user interface 3600 generated on the mobile device 102 of the caregiver 12. The user interface 3600 includes a chat settings 3602 pop-up that includes an icon 3604 that can be selected by the caregiver 12 to turn off the ability for the patient 14 and the family members 16 to reply to the updates sent from the caregiver 12.

Figure 37:
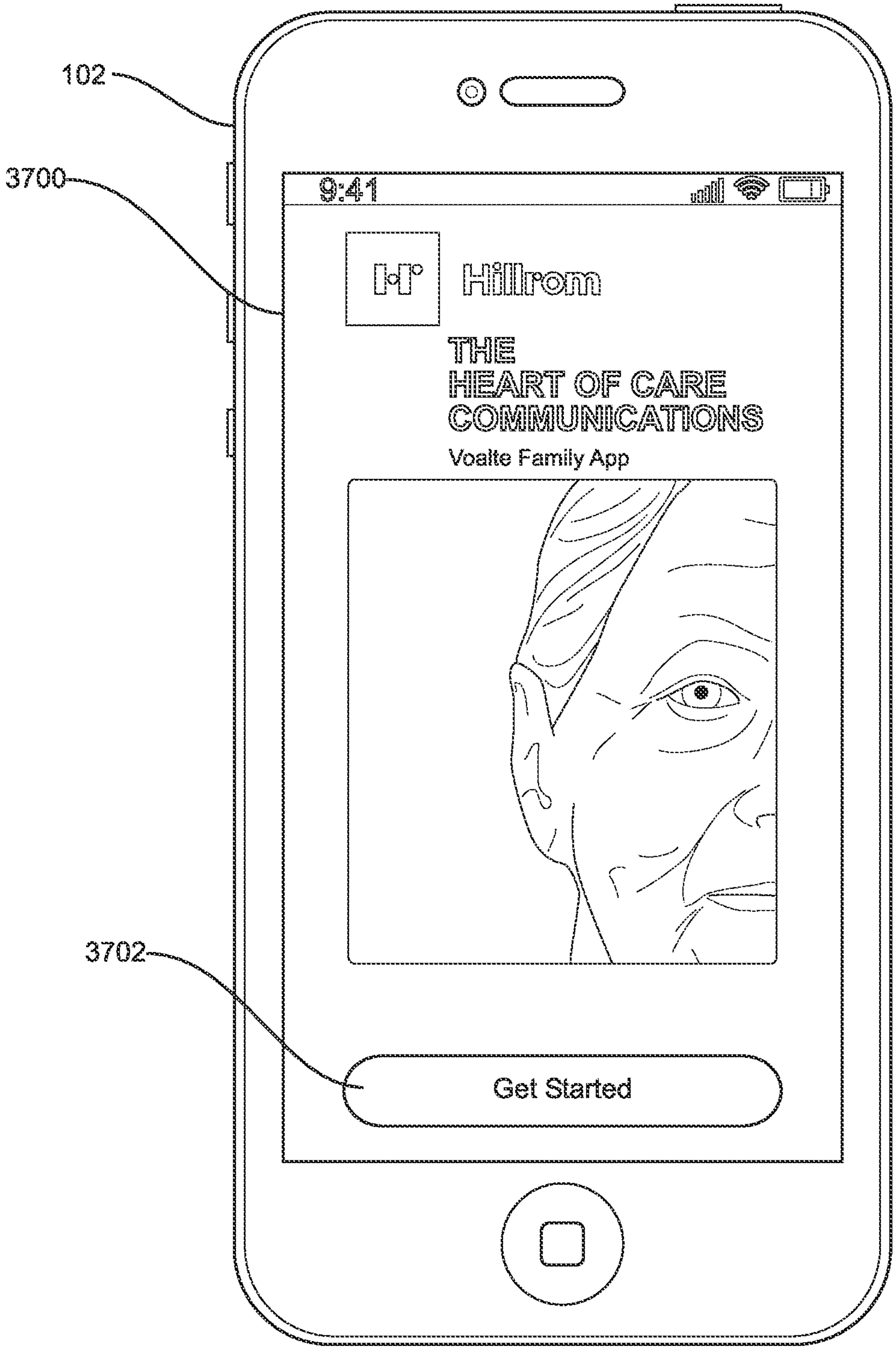
FIG. 37 illustrates an example of an onboarding screen generated on a mobile device of a family member after installation of the family communications application of FIG. 1.

FIG. 37 illustrates an example of an onboarding screen 3700 generated on a mobile device 102 of the family member 16 after the family communications application 106 is installed on the mobile device 102 of the family member 16. The family communications application 106 can be installed on the mobile device 102 of the family member 16 via download such as from a digital distribution platform such as an app store (e.g., the App Store or the Google Play Store depending on whether the mobile device 102 is an iOS or Android device).

The onboarding screen 3700 is generated following receipt of an invitation on the mobile device 102 (either by scanning the machine readable data 1104 or by receiving a message invitation sent via the mobile number field 1106 shown in FIG. 11). In some examples, the invitation includes metadata associated with the patient 14 such that the family communications application 106 when downloaded on the mobile device 102 of the family member 16 is automatically linked to the patient 14. This can eliminate the need for the family member 16 to identify the patient 14, which can make setting up the family communications application 106 easier and reduce human errors from linking the family member 16 to the wrong patient.

The onboarding screen 3700 is displayed on the mobile device 102 when the family member 16 opens the family communications application 106 for the first time. The onboarding screen 3700 includes an icon 3702 that the family member 16 can select to initiate an onboarding process for setting up the family communications application 106 on the mobile device 102. In some examples, the family communications application 106 requires the family member to set up authentication such as a 4-digit pin or biometric ID (e.g., fingerprint) in order for the family member 16 to use the family communications application 106.

Figure 38:
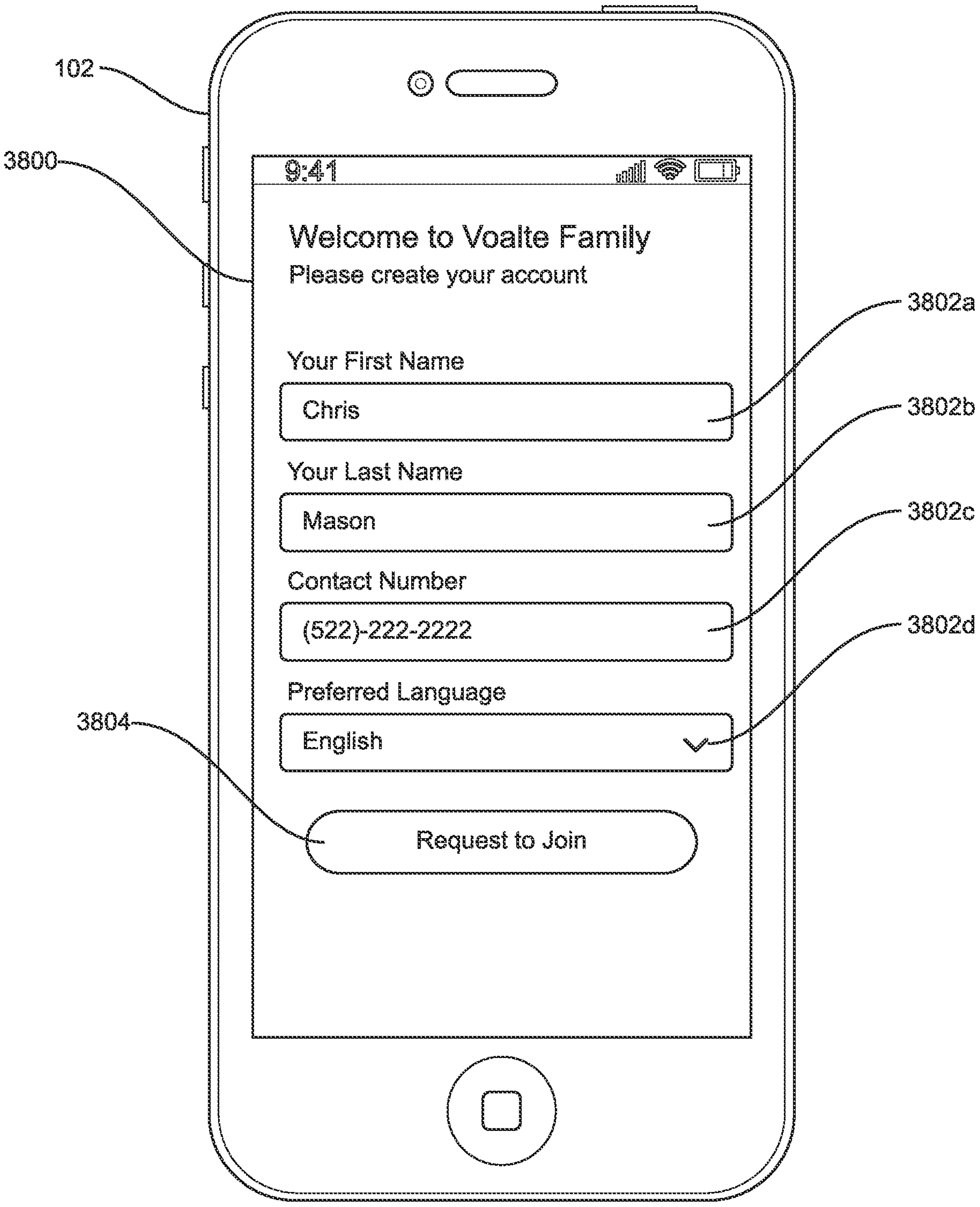
FIG. 38 illustrates an example of a registration screen generated on the mobile device of the family member by the family communications application in response to the family member selecting an icon on the onboarding screen of FIG. 37.

FIG. 38 illustrates an example of a registration screen 3800 generated on the mobile device 102 of the family member 16 by the family communications application 106 in response to the family member 16 selecting the icon 3702 from the onboarding screen 3700. As shown in FIG. 38, the registration screen 3800 prompts the family member 16 to create an account by providing information in a plurality of fields 3802*a*-3802*d* such as, without limitation, the family member's first name, last name, telephone contact number, and preferred language. When the family member 16 has entered all of the requested information into the plurality of fields 3802*a*-3802*d*, the family member 16 can select a request to join icon 3804 to enter the information and request authorization to use the family communications application 106.

The field 3802*d* allows the family member 16 to select their preferred language. For example, the family member 16 can select their preferred language as English, Arabic, Chinese, Creole, French, Hindi, Japanese, Portuguese, Russian, Spanish, or another language. The family communications application 106 is configured to automatically translate the updates sent from the mobile device 102 of the caregiver 12 into the preferred language of the family member 16 selected in field 3802*d* when the preferred language of the family member 16 differs from the preferred language of the caregiver 12. For example, the caregiver 12 can generate an update by using the various screens shown in FIGS. 18-36 in a first language (e.g., English), and the family member 16 can receive the update on their mobile device 102 in a second language (e.g., Spanish) without requiring any input from the caregiver 12 or the family member 16 aside from the family member 16 selecting their preferred language on the registration screen 3800.

In some examples, predefined translations for common languages in the area of the clinical care environment 10 (e.g., hospital) can be generated and entered by the clinical care environment 10 into the family communications application 106 for translating the updates. In instances where the clinical care environment 10 has not provided a custom language translation for the predefined messages, patient condition summaries, or patient plans in the preferred language of a family member, a third-party translation service can be used to automatically translate the update into the family member's preferred language.

Figure 39:
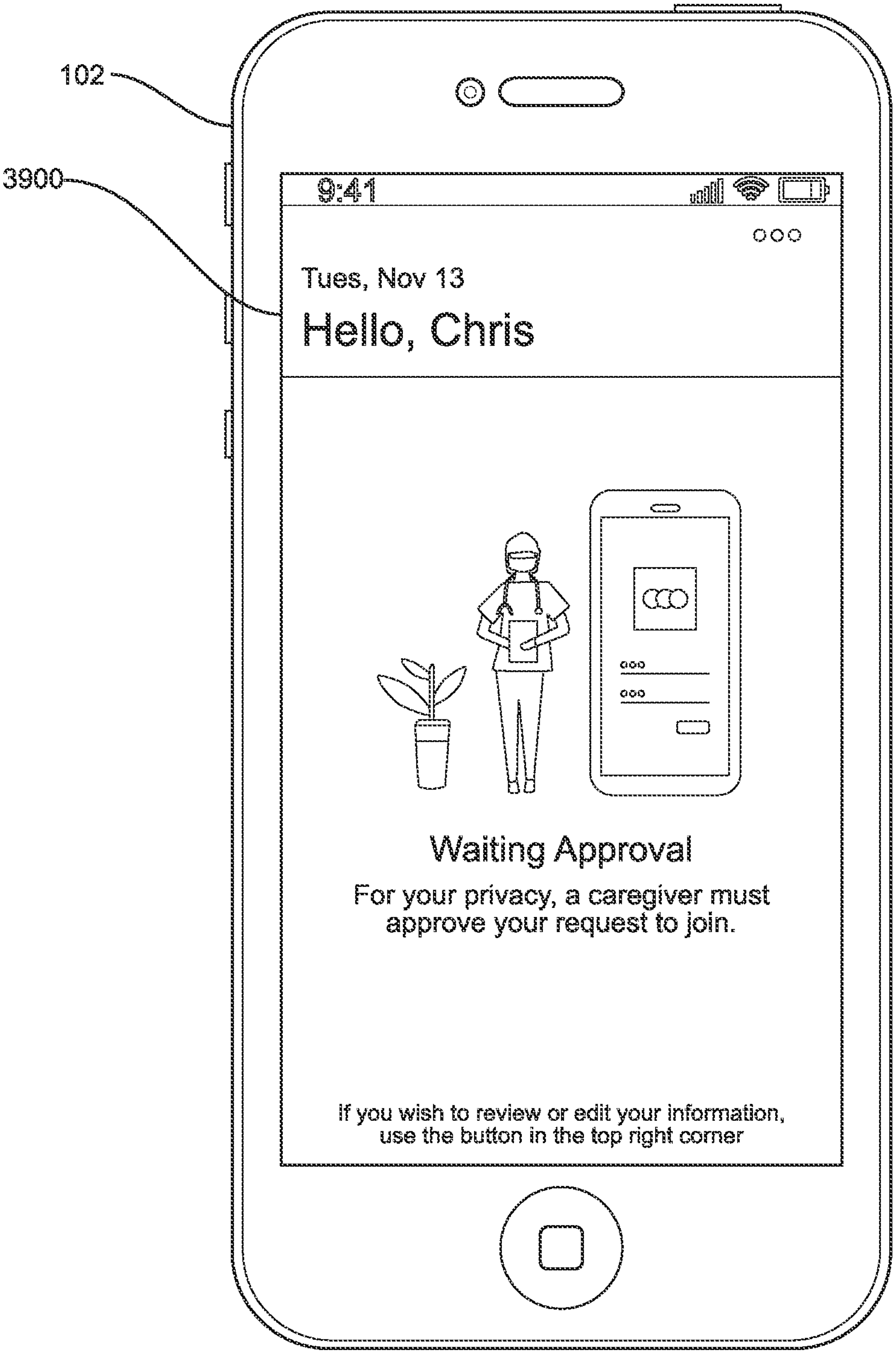
FIG. 39 illustrates an example of a screen displayed on the mobile device of the family member by the family communications application of FIG. 1, the screen displayed while approval of the family member is pending.

The family communications application 106 verifies the information entered by the family member 16 on the registration screen 3800 before the family member is authorized to use the family communications application 106. This can prevent unauthorized users from communicating with the caregiver 12, and thereby prevent unauthorized access to protected health information. FIG. 39 illustrates an example of a screen 3900 displayed on the mobile device 102 of the family member 16 while the approval of the family member is pending.

Figure 40:
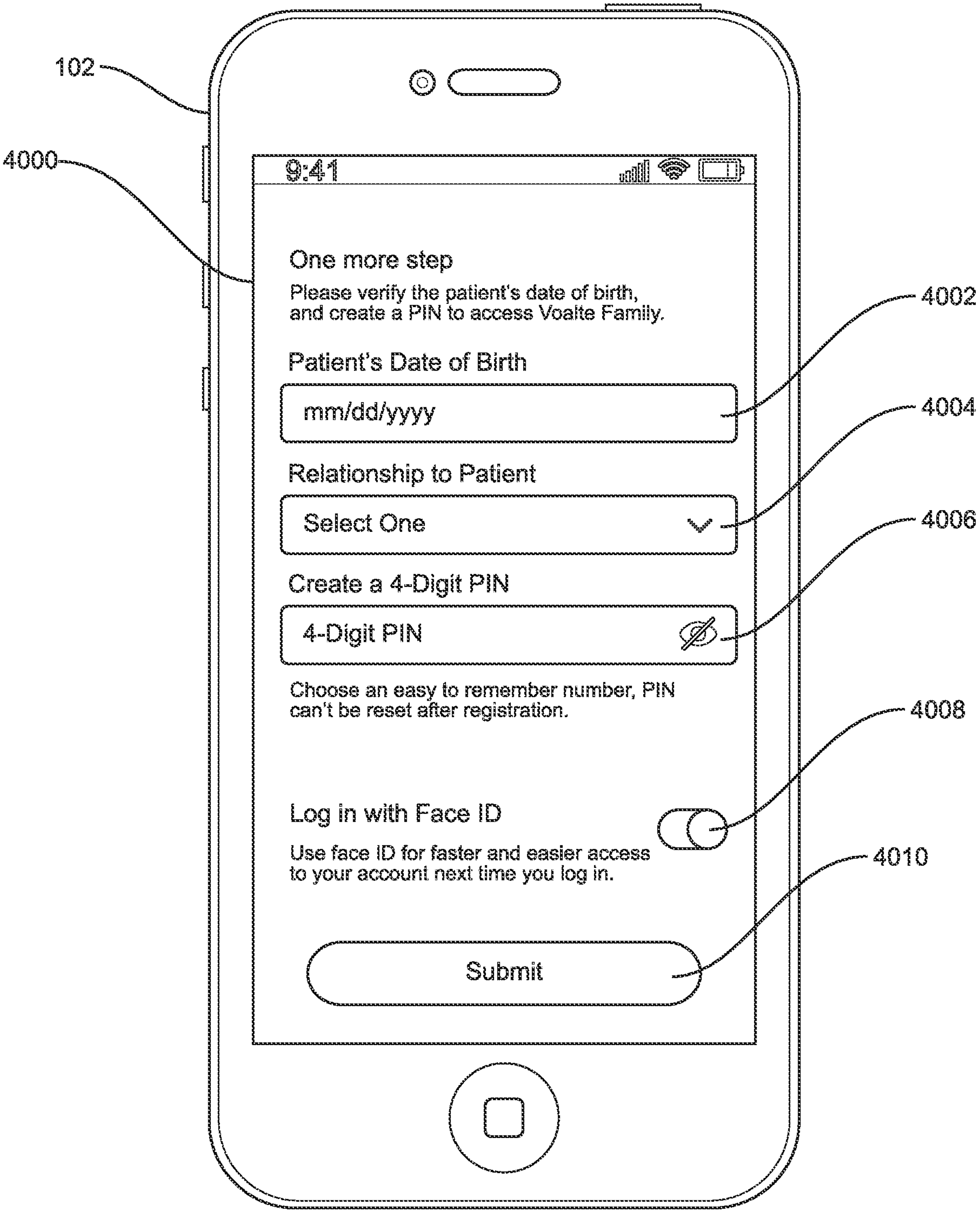
FIG. 40 illustrates an example of a verification screen displayed on the mobile device of the family member by the family communications application of FIG. 1, the screen displayed after the family member is approved.

FIG. 40 illustrates an example of a verification screen 4000 displayed on the mobile device 102 of the family member 16 by the family communications application 106 when the family member 16 is approved. The verification screen 4000 requests additional information to verify the identity of the patient 14 to ensure that the family member 16 is linked to the correct patient. For example, the verification screen 4000 includes a field 4002 for the family member 16 to enter the patient's date of birth. By requesting entry of the patient's date of birth, this additional verification step can further prevent unauthorized users from communicating with the caregiver 12, and thereby prevent unauthorized access to protected health information.

The verification screen 4000 further includes a field 4004 for the family member 16 to select their relationship to the patient 14 (e.g., spouse, brother, daughter, etc.), and a field 4006 to create a user PIN. The verification screen 4000 can include an option 4008 for the family member 16 to log into the family communications application 106 using facial recognition.

Once the requested information on the verification screen 4000 is entered by the family member 16, the family member 16 can select the submit icon 4010 to submit the requested information. The user PIN (i.e., field 4006) and facial recognition (i.e., option 4008) can further prevent unauthorized access to protected health information.

Figure 41:
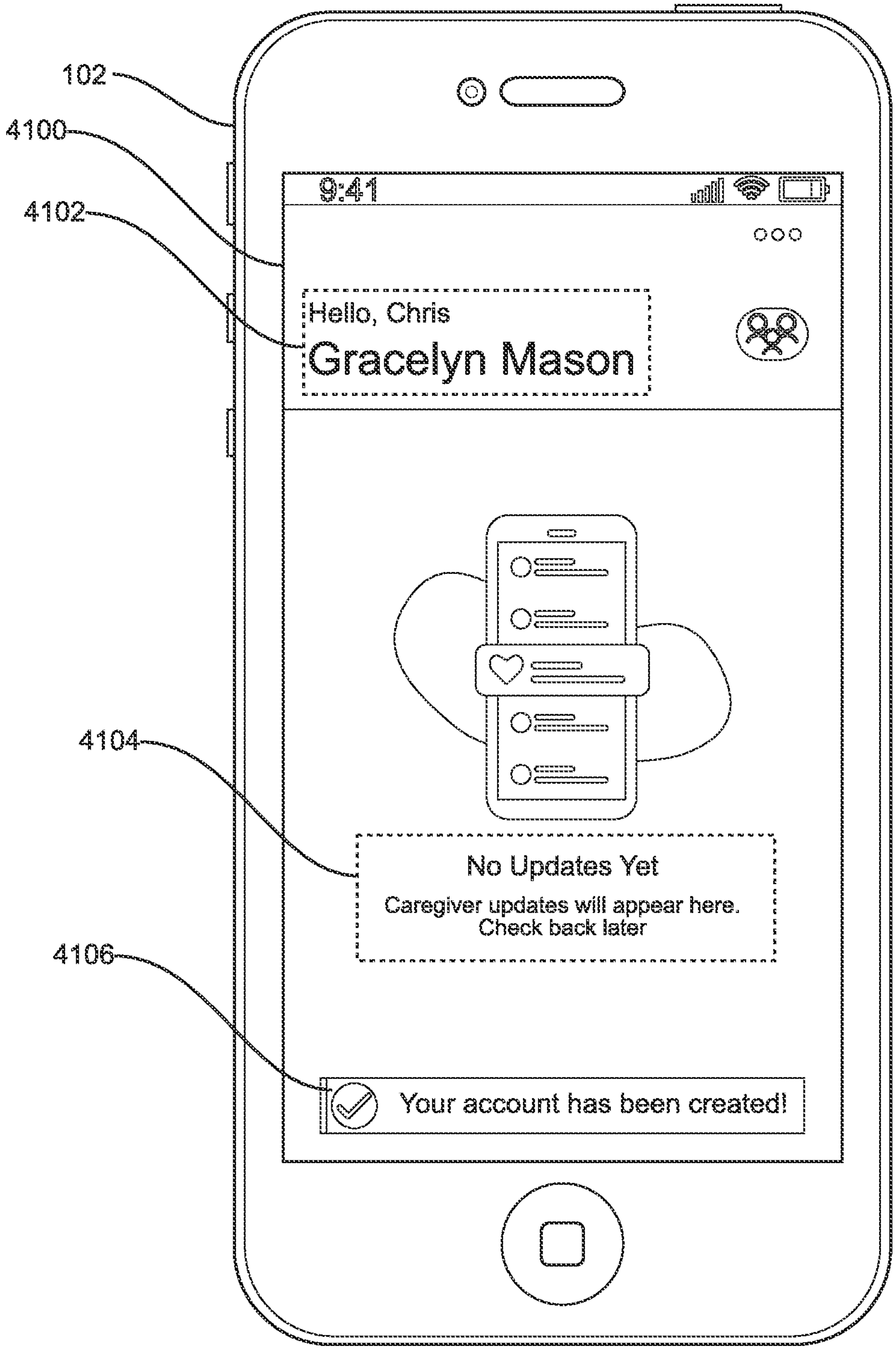
FIG. 41 illustrates an example of a home screen displayed on the mobile device of the family member by the family communications application of FIG. 1, the home screen displayed after completion of the onboarding process by the family member.

FIG. 41 illustrates an example of a home screen 4100 displayed on the mobile device 102 of the family member 16 after completion of the onboarding process. The home screen 4100 can include a message 4102 such as "Hello, [first name of family member]" and identify the patient 14 by their name (e.g., Gracelyn Mason). In this example, no updates have been received from the caregiver 12 such that the home screen 4100 displays a message 4104 such as "NO UPDATES YET Caregiver updates will appear here. Check back later." When the onboarding process is completed for the first time and the family member 16 is approved as an authorized user of the family communications application 106, the home screen 4100 can illustrate a message 4106 such as "Your account has been created!" that includes a checkmark sign.

Figure 42:
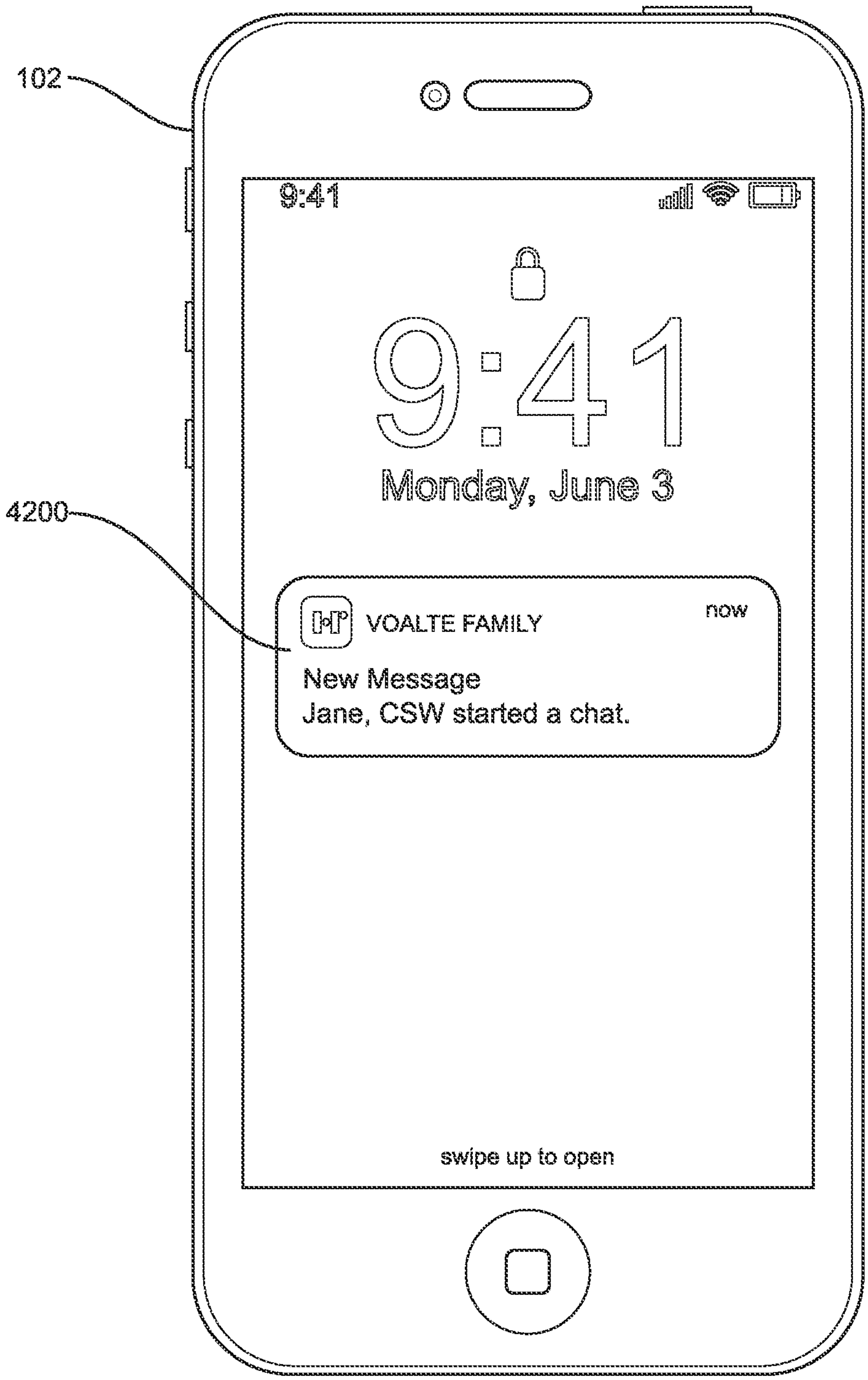
FIG. 42 illustrates an example of a notification that can be displayed on the mobile device of the family member by the family communications application of FIG. 1.

FIG. 42 illustrates an example of a notification 4200 that can be displayed on the mobile device 102 of the family member 16 by the family communications application 106. The notification 4200 can be displayed when a new update is received from the caregiver 12.

Figure 43:
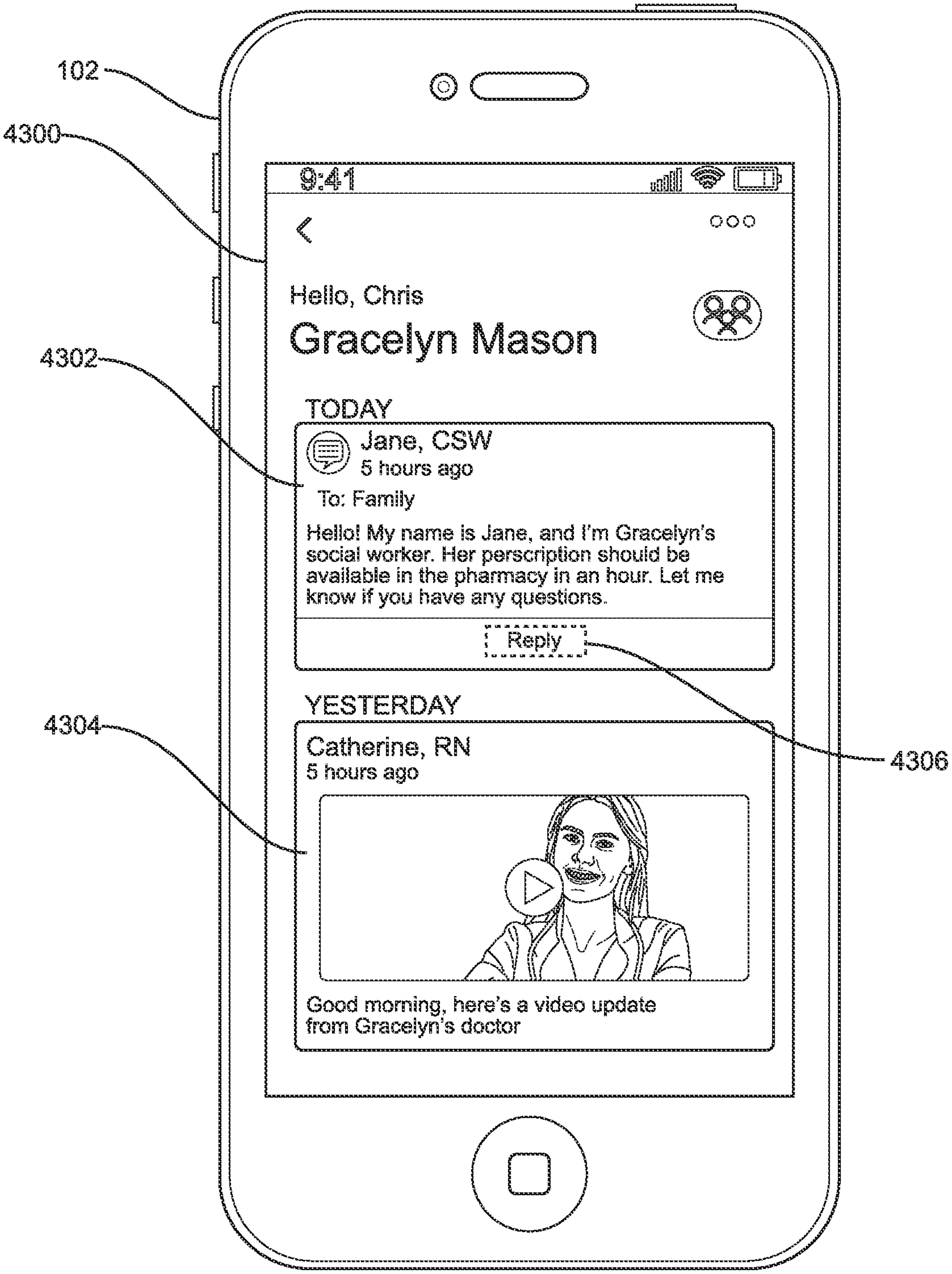
FIG. 43 illustrates an example of a home screen displayed on the mobile device of the family member by the family communications application of FIG. 1, the home screen displayed following a selection or opening of the notification shown in FIG. 42.

FIG. 43 illustrates an example of a home screen 4300 that can be displayed by the family communications application 106 when opened by the family member 16 such as following receipt of the notification 4200 shown in FIG. 42. In the example shown in FIG. 43, the home screen 4300 includes one or more updates received from caregivers responsible for providing care to the patient 14. The updates can be listed in chronological order.

The home screen 4300 includes an update 4302 received from a social worker assigned to the patient 14, and an update 4304 received from the doctor assigned to the patient 14. In this example, the update 4302 identifies the caregiver 12 (e.g., "Jane, CSW"), when the update was received (e.g., "5 hours ago"), the recipient(s) of the update (e.g., "To: Family"), and a message (e.g., "Hello! My name is Jane, and I'm Gracelyn's social worker. Her prescription should be available in the pharmacy in an hour. Let me know if you have any questions."). In this example, the update 4302 further includes a reply icon 4306 that allows the family member 16 to reply to the update 4302. Thus, in this example, the family communications application 106 enables two-way communications between the caregiver 12 and the family members 16.

Figure 44:
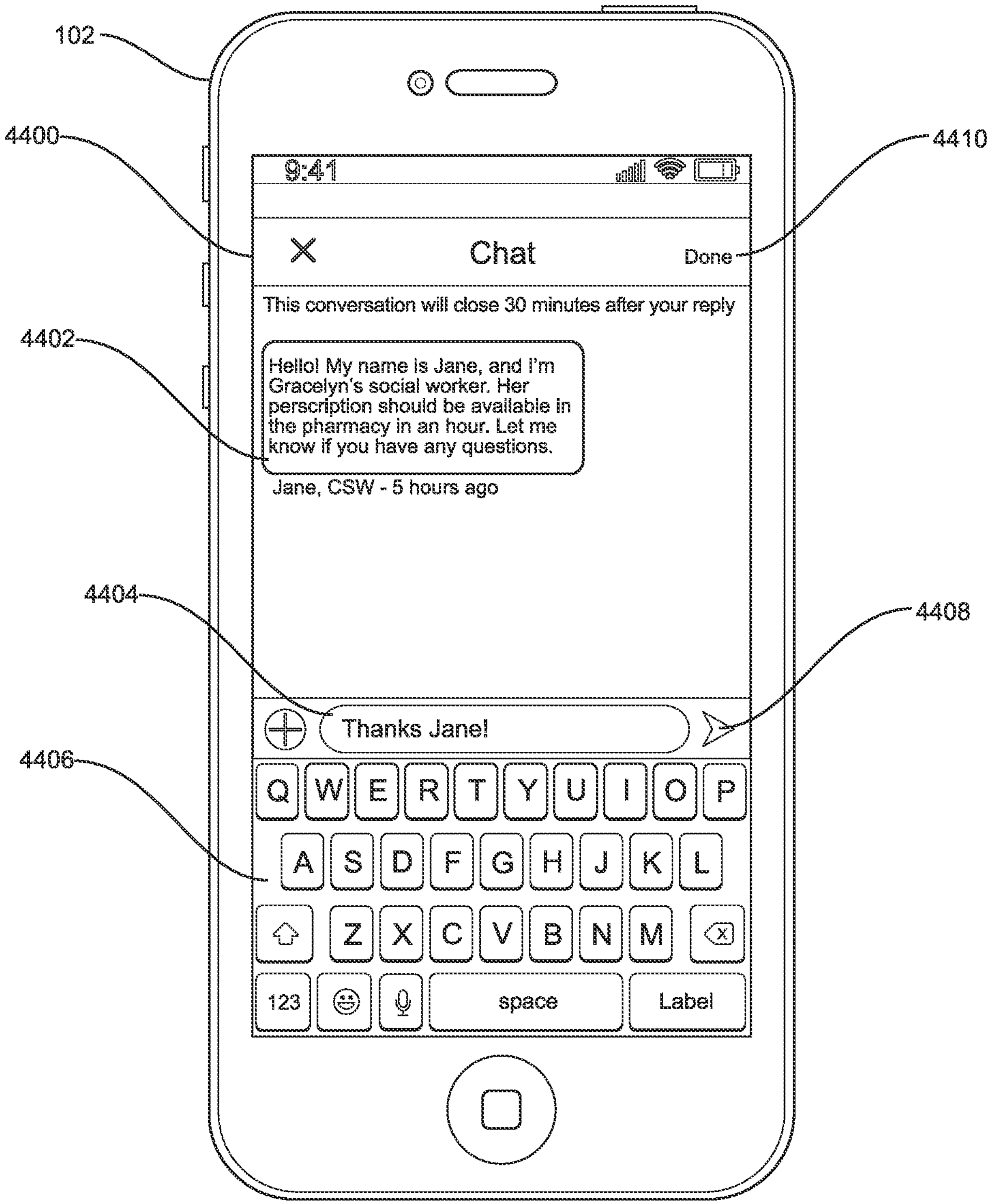
FIG. 44 displays a chat screen displayed by the family communications application of FIG. 1 in response to the family member selecting a reply icon on the home screen of FIG. 43.

FIG. 44 displays a chat screen 4400 displayed by the family communications application 106 in response to the family member 16 selecting the reply icon 4306. The chat screen 4400 includes an update 4402, a text box 4404 for the family member 16 to type a message using a keyboard 4406. Upon completion of the message, the family member 16 can select a send icon 4408 to send the message in reply to the update 4402.

In some examples, the two-way conversation in reply to an update is limited for certain duration of time. For example, the two-way conversation can automatically close 30 minutes after a reply is sent from the family member 16. In some examples, the two-way communications provided by the family communications application 106 are only enabled in reply to an update received from a caregiver 12 such that a family member 16 cannot use the family communications application 106 to initiate a conversation with the caregiver 12.

Figure 45:
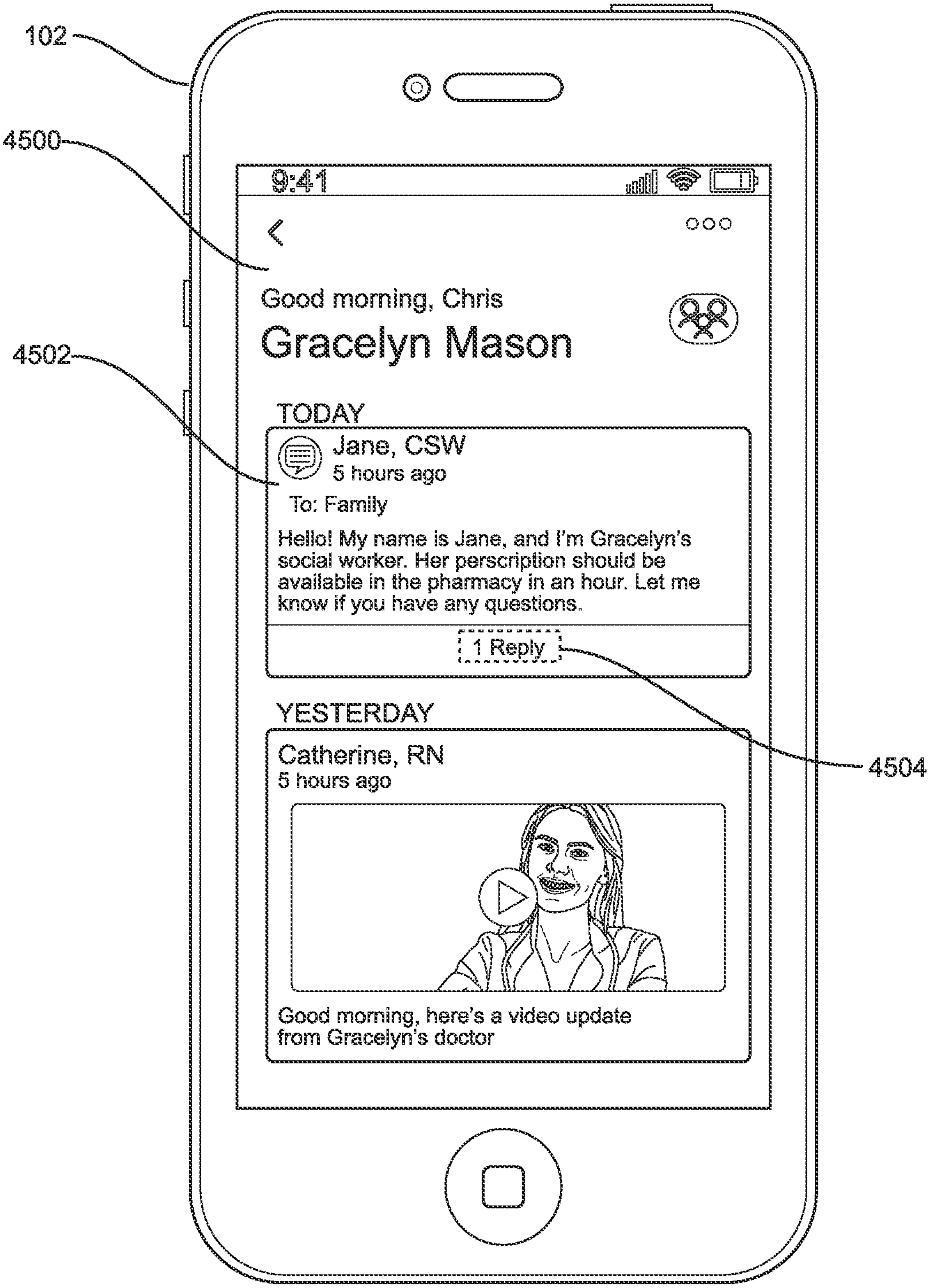
FIG. 45 illustrates an example of a home screen displayed by the family communications application of FIG. 1 after a reply is sent from the chat screen of FIG. 44.

After the reply is sent by selection of the send icon 4408, the family member 16 can thereafter select a done icon 4410 to close the chat screen 4400. FIG. 45 illustrates an example of a home screen 4500 displayed by the family communications application 106 after a reply is sent to an update 4502. As shown in FIG. 45, the update 4502 now includes an indicator 4504 of a number of replies (e.g., 1 reply, 2 replies, 3 replies, etc.) received for the update 4502.

Figure 46:
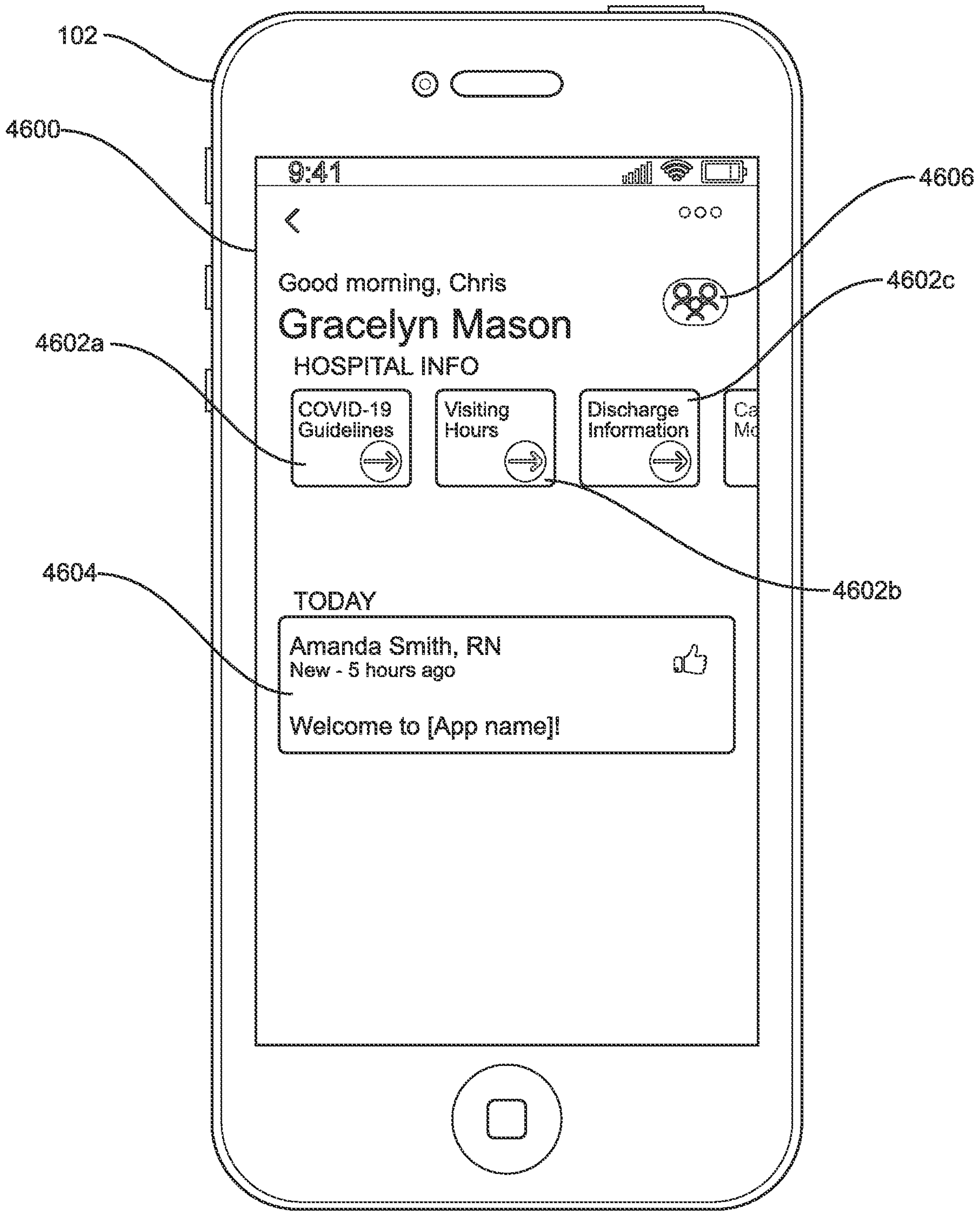
FIG. 46 illustrates another example of a home screen generated on the mobile device of the family member by the family communications application of FIG. 1.

FIG. 46 illustrates another example of a home screen 4600 that is generated on the mobile device 102 of the family member 16 by the family communications application 106. In some instances, the home screen 4600 is generated after verification of the information entered by the family member 16 on the verification screen 4000.

The home screen 4600 may include a greeting for the family member 16 such as "Good morning, Chris" and also identify the patient 14 by their name (e.g., "Gracelyn Mason"). The home screen 4600 provides a plurality of links 4602A-4602C to clinical care environment information such as visitor guidelines, visiting hours, discharge information, and the like. The links 4602A-4602C can be based on the unit in the clinical care environment 10 where the patient 14 is admitted. The home screen 4600 can also include an initial message 4604 that is automatically generated and sent to the family member 16 after the family member's successful enrollment and onboarding with the family communications application 106.

In some examples, the family communications application 106 provides a family icon 4606 for the family member 16 to select to add additional family members to receive updates through the family communications application 106. For example, the family member 16 can be designated a primary family member, and the family member 16 can add secondary family members to receive the updates. In certain examples, adding secondary family members follows a similar procedure as the operation 206 described above.

In response to the family member 16 selecting the family icon 4606, an add family member screen can be generated by the family communications application 106 on the mobile device 102 of the family member 16 that is substantially similar to the add family screen 1100 shown in FIG. 11. The add family member screen allows the family member 16 to invite the secondary family members. For example, the add family member screen can display machine readable data such as a QR code that the secondary family members can scan with their mobile devices. Alternatively, the primary family member can use the add family member screen to send message invitations that are delivered to the mobile devices of the secondary family members.

Once the secondary family members receive an invitation on their mobile devices (either by scanning the machine readable data or by receiving a message invitation), the secondary family members are prompted to download and set up the family communications application 106 on their mobile devices. Thereafter, the secondary family members can receive on their mobile devices the same updates received by the primary family member.

In certain examples, the primary family member controls authorization of the secondary family members to receive the updates from the caregivers 12. For example, the primary family member can allow or block certain secondary family members from receiving the updates, whereas the secondary family members cannot add additional family members or block other family members from receiving the updates from the caregivers 12.

Figure 47:
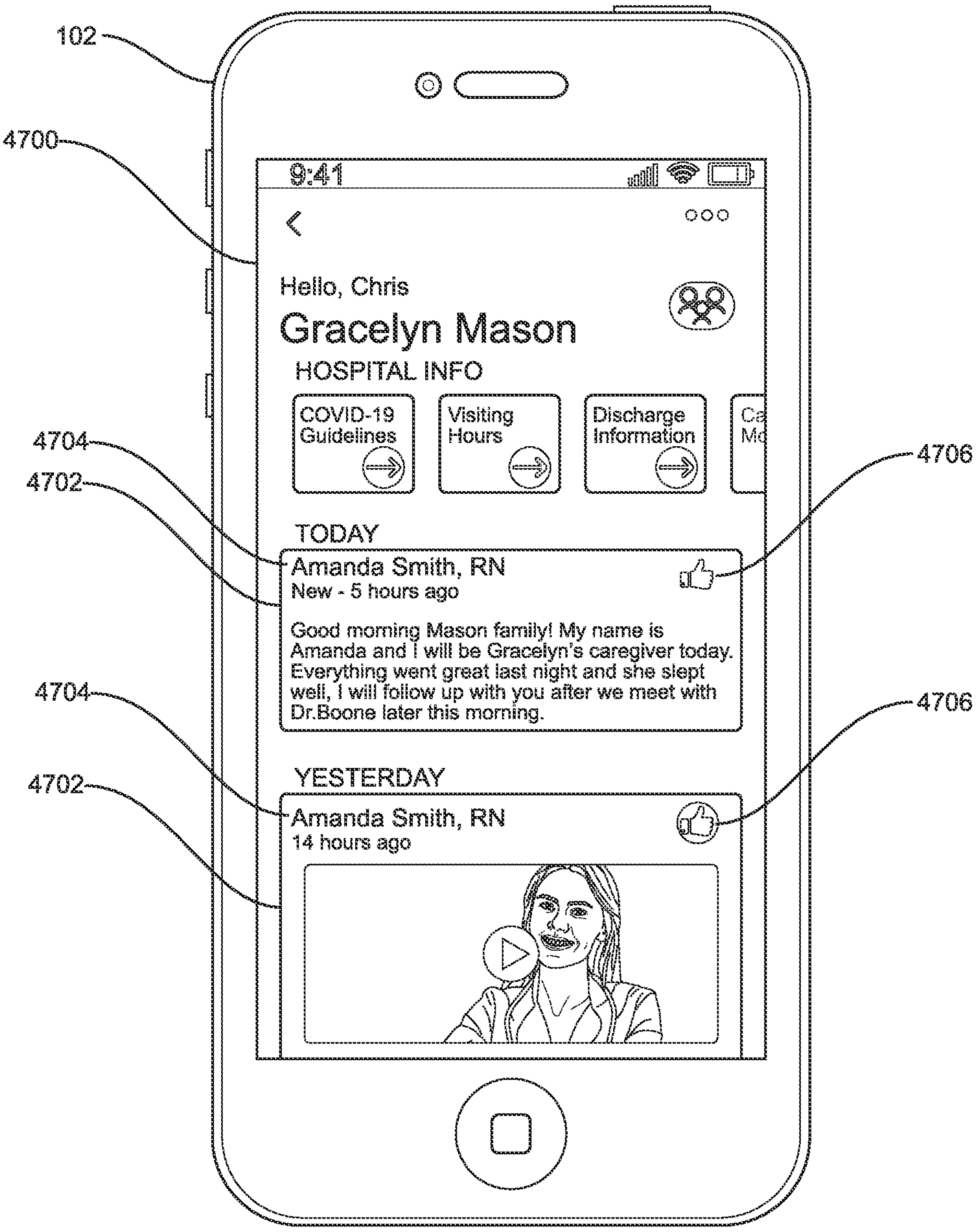
FIG. 47 illustrates an example of an updates screen generated on the mobile device of the family member by the family communications application of FIG. 1.

FIG. 47 illustrates an example of an updates screen 4700 that is generated on the mobile device 102 of the family member 16 by the family communications application 106. In this example, the updates screen 4700 displays updates 4702 on the patient 14 in chronological order with the most recent update 4702 being displayed first. The updates 4702 can be categorized by the day they were sent such as by displaying identifiers such as "Today" or "Yesterday". Each update 4702 can include information 4704 that identifies the date and time that the update was sent, and the name of the caregiver who sent the update.

Each update 4702 can also include an emoji icon 4706 that the family member 16 can select as a way to respond back to the caregiver 12 who sent the update. In the example shown in FIG. 47, the emoji icon 4706 is a thumbs-up symbol. While the family communications application 106 allows the caregiver 12 to send the updates 4702 to the family member 16, in some examples the family communications application 106 limits communication from the family member 16 to the caregiver 12 (e.g., such as when the family member 16 is blocked from replying to an update). Thus, selection of the emoji icon 4706 allows the family member 16 to communicate with the caregiver 12 when blocked from replying to the update. This can reduce the number of reply messages that the caregiver 12 receives from the family member 16 such that the caregiver 12 has more available time to provide care to the patient 14 which can result in an increase in patient satisfaction scores, while also allowing the caregiver 12 to send the updates 4702 to the family member 16 to keep the family member informed on the status and condition of the patient 14, and thereby improve the family member's satisfaction as well.

In some instances, another limited communication that can be sent from the family member 16 to the caregiver 12 allows the family member 16 to propose a different time to schedule a call with the caregiver 12 or doctor of the patient 14 from the time included in the update that was selected by the caregiver 12 using the schedule call screen 3000 of FIG. 30.

Figure 48:
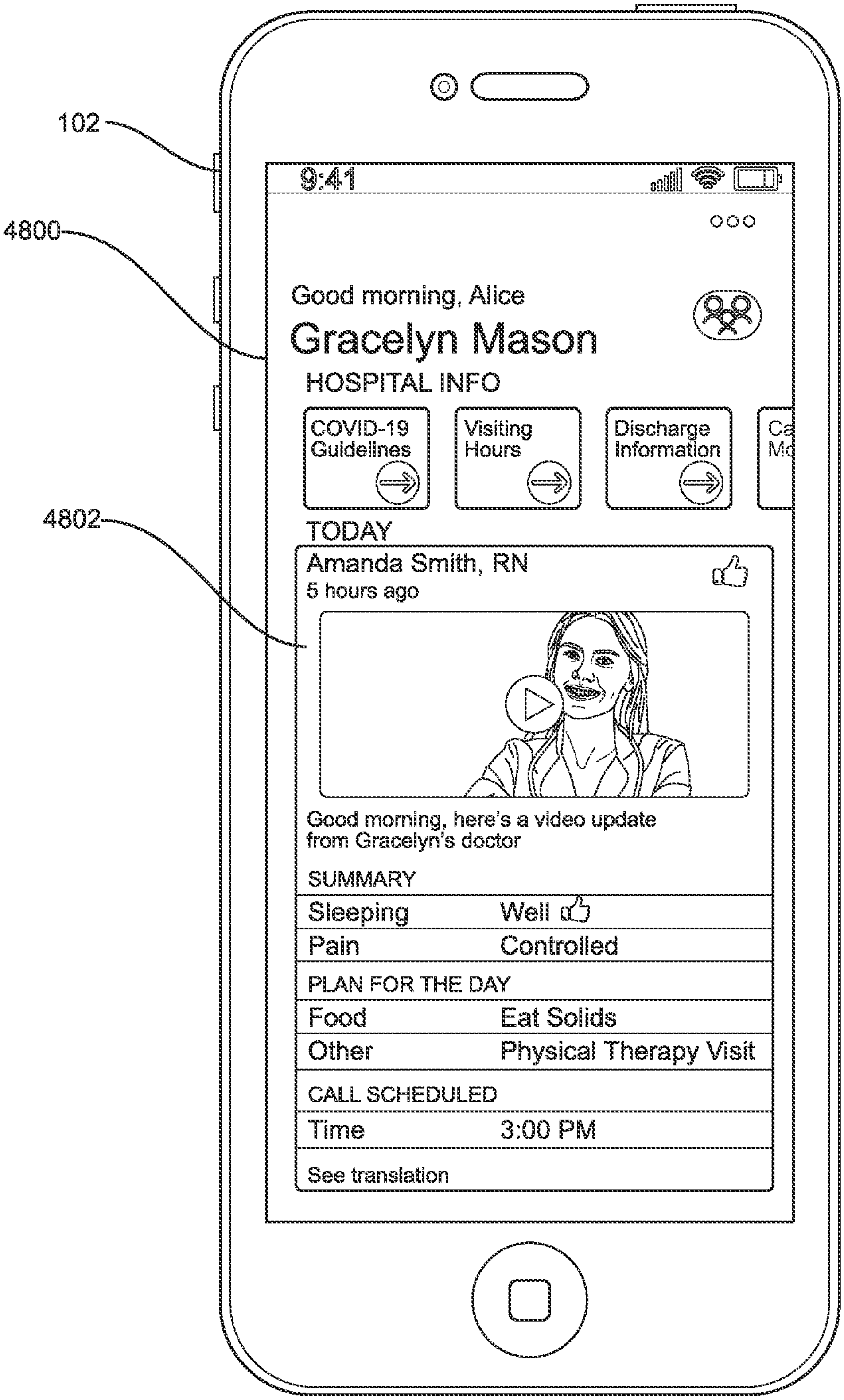
FIG. 48 illustrates another example of an updates screen on the mobile device of the family member that includes an update that corresponds to the update sent from the update preview screen on the mobile device of the caregiver shown in FIG. 32.

FIG. 48 illustrates an example of an updates screen 4800 on the mobile device 102 of the family member 16 that includes an update 4802 that corresponds to the update 3202 sent from the update preview screen 3200 on the mobile device 102 of the caregiver 12 shown in FIG. 32. As shown in FIG. 48, the update 4802 substantially matches the update 3202 generated and sent in accordance with the steps 1702-1712 of FIG. 17, and the screens shown in FIGS. 18-36.

Figure 49:
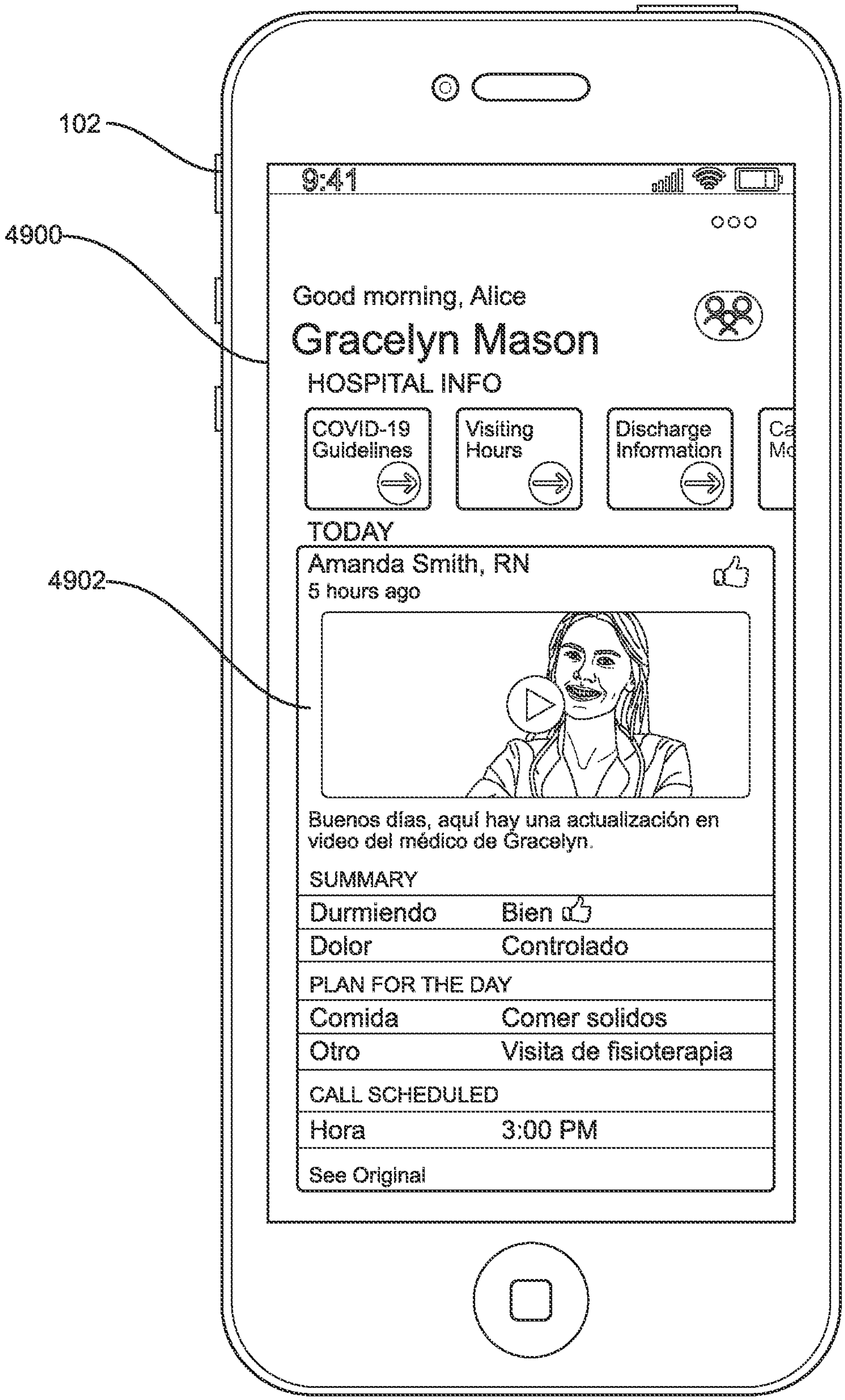
FIG. 49 illustrates another example of an updates screen on the mobile device of the family member that includes an update that corresponds to the update sent from the update preview screen on the mobile device of the caregiver shown in FIG. 32, in this example the update is translated into Spanish based on a preferred language selection.

FIG. 49 illustrates an example of an updates screen 4900 on the mobile device 102 of the family member 16 that includes an update 4902 that corresponds to the update 3202 sent from the update preview screen 3200 on the mobile device 102 of the caregiver 12 shown in FIG. 32. In this example, the update 4902 is translated into Spanish based on a selection of Spanish as the preferred language of the family member 16 (see field 3802*d* in FIG. 38).

In view of the foregoing, the graphical user interfaces and screens that are shown in the figures and described above provide a technical effect by improving efficiencies related to the operation of the mobile device 102 as a means to communicate and receive an update of the patient 14. These efficiencies can extend to how data is displayed and interactions with the data on the mobile device 102. Moreover, these graphical user interfaces and screens integrate the communication of the update of the patient 14 to the family members 16 into a practical application that is more effective and efficient than previous methods.

Figure 50:
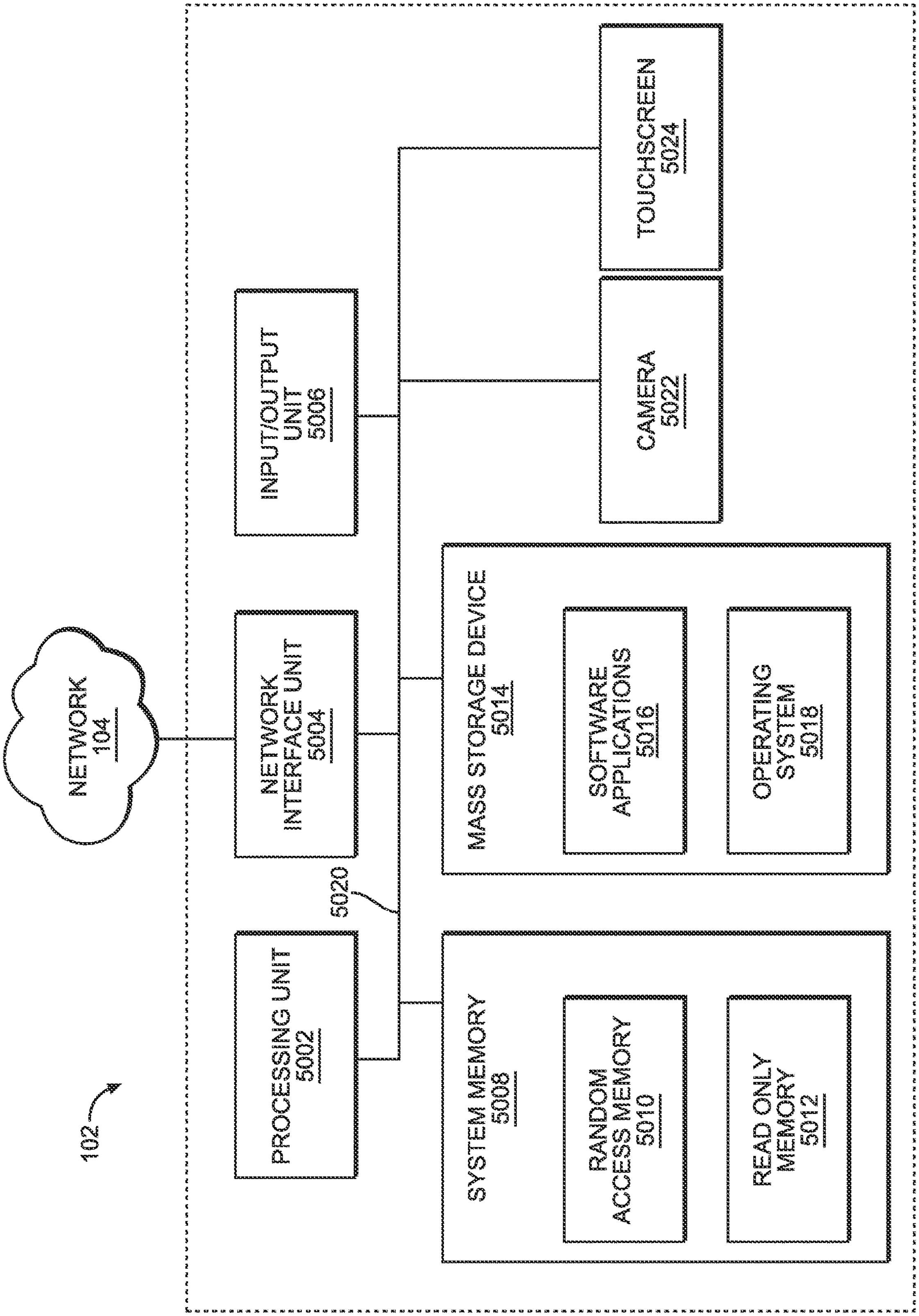
FIG. 50 schematically illustrates a mobile devices which can be used by a caregiver or a family member to implement aspects of the present disclosure using features of the family communications application of FIG. 1.

FIG. 50 schematically illustrates one of the mobile devices 102 which can be used by a caregiver 12 or family member 16 to implement aspects of the present disclosure using features of the family communications application 106, as discussed above. The mobile device 102 includes a processing unit 5002, a system memory 5008, and a system bus 5020 that couples the system memory 5008 to the processing unit 5002. The processing unit 5002 is an example of a processing device such as a central processing unit (CPU). The system memory 5008 includes a random-access memory ("RAM") 5010 and a read-only memory ("ROM") 5012. A basic input/output logic containing the basic routines that help to transfer information between elements within the mobile device 102, such as during startup, is stored in the ROM 5012.

The mobile device 102 can also include a mass storage device 5014 that is able to store software instructions and data. The mass storage device 5014 is connected to the processing unit 5002 through a mass storage controller (not shown) connected to the system bus 5020. The mass storage device 5014 and its associated computer-readable data storage media provide non-volatile, non-transitory storage for the mobile device 102.

Although the description of computer-readable data storage media contained herein refers to a mass storage device, it should be appreciated by those skilled in the art that computer-readable data storage media can be any available non-transitory, physical device or article of manufacture from which the device can read data and/or instructions. In certain embodiments, the computer-readable storage media comprises entirely non-transitory media. The mass storage device 5014 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, or any other medium which can be used to store information, and which can be accessed by the device.

The mobile device 102 operates in a networked environment using logical connections to devices through the communications network 104. The mobile device 102 connects to the communications network 104 through a network interface unit 5004 connected to the system bus 5020. The network interface unit 5004 may also be utilized to connect to other types of communications networks and devices, including through Bluetooth and Wi-Fi.

The mobile device 102 can also include an input/output controller 5006 for receiving and processing inputs and outputs from a number of peripheral devices. Examples of peripheral devices may include, without limitation, a camera 5022 and a touchscreen 5024.

The mass storage device 5014 and the RAM 5010 can store software instructions and data. The software instructions can include an operating system 5018 suitable for controlling the operation of the mobile device 102. The mass storage device 5014 and/or the RAM 5010 also store software instructions 5016, that when executed by the processing unit 5002, cause the device to provide the functionality of the mobile device 102 discussed herein.

The various embodiments described above are provided by way of illustration only and should not be construed to be limiting in any way. Various modifications can be made to the embodiments described above without departing from the true spirit and scope of the disclosure.

What is claimed is:

1. A device for managing healthcare communications, the device comprising:

a network interface unit that connects the device to a communications network;

a camera;

at least one processor; and a memory storing instructions which, when executed by the at least one processor, cause the at least one processor to:

display machine-readable data that is scannable by a second device, the machine-readable data including metadata for linking the second device to a patient, and the metadata storing a configuration to allow or block the second device from adding additional devices to receive updates;

display a screen including predefined options for selecting a pre-generated message, wherein the predefined options are based on a unit where a patient is admitted in a clinical care environment, and wherein the unit where the patient is admitted is determined from a second set of machine-readable data detected by the camera scanning the second set of machine-readable data, and the second set of machine-readable data identifying the patient;

configure the predefined options based on the unit to provide a unit-specific template for the pre-generated message;

generate, using the unit-specific template, an update of the patient based on a selection of the pre-generated message, wherein the update includes the metadata associated with the patient;

send the update to the second device operated by a family member of the patient, the second device connected to the communications network, wherein the second device is added as an additional device to receive the update, and wherein the metadata included in the update links the second device to the patient, and wherein the link causes information to be retrieved from an electronic medical record over the communications network to automate future updates, and wherein the information retrieved from the electronic medical record is converted for display on the second device; and block the second device from adding the additional devices to receive the update based on the metadata linking the second device to the patient.

2. The device of claim 1, wherein the screen is configurable to add a photograph or a video of the patient to the update.

3. The device of claim 1, wherein the screen is configurable to add a time to the update for scheduling a call with the family member.

4. The device of claim 1, wherein the memory stores further instructions which, when executed by the at least one processor, cause the at least one processor to:

display a preview of the update before the update is sent to the second device.

5. The device of claim 1, wherein the memory stores further instructions which, when executed by the at least one processor, cause the at least one processor to:

retrieve links to information on the clinical care environment based on the unit; and display the links on the second device, wherein the links include visitor guidelines, visiting hours, and discharge information specific to the unit.

6. The device of claim 1, wherein the memory stores further instructions which, when executed by the at least one processor, cause the at least one processor to:

receive a preferred language from the family member; and automatically translate the update into the preferred language using predefined translations generated and entered by the clinical care environment.

7. The device of claim 1, wherein the memory stores further instructions which, when executed by the at least one processor, cause the at least one processor to:

verify identity of the patient by requesting entry of additional patient information through the second device before allowing access to updates; and prevent unauthorized access to protected health information by validating the additional patient information.

8. The device of claim 1, wherein the memory stores further instructions which, when executed by the at least one processor, cause the at least one processor to:

enable the family member to propose an alternative time for a scheduled call with the caregiver through the second device; and limit communication from the family member to the caregiver to emoji responses and call time proposals to reduce interruptions to the caregiver.

9. A method of managing healthcare communications, the method comprising:

displaying machine-readable data that is scannable by a second device, the machine-readable data including metadata for linking the second device to a patient, and the metadata storing a configuration to allow or block the second device from adding additional devices to receive updates;

displaying a screen including predefined options for selecting a pre-generated message, wherein the predefined options are based on a unit where a patient is admitted in a clinical care environment, and wherein the unit where the patient is admitted is determined from a second set of machine-readable data detected by a camera scanning the second set of machine-readable data, and the a second set of machine-readable data identifying the patient;

configuring the predefined options based on the unit to provide a unit-specific template for the pre-generated message;

generating, using the unit-specific template, an update of the patient based on a selection of the pre-generated message, wherein the update includes the metadata associated with the patient;

sending the update over a communications network to the second device operated by a family member of the patient, the second device connected to the communications network, wherein the second device is added as an additional device to receive the update, and wherein the metadata included in the update links the second device to the patient, and wherein the link causes information to be retrieved from an electronic medical record over the communications network to automate future updates, and wherein the information retrieved from the electronic medical record is converted for display on the second device; and blocking the second device from adding the additional devices to receive the update based on the metadata linking the second device to the patient.

10. The method of claim 9, further comprising:

retrieving links to information on the clinical care environment based on the unit; and displaying the links on the second device, wherein the links include visitor guidelines, visiting hours, and discharge information specific to the unit.

11. The method of claim 9, further comprising:

receiving a preferred language from the family member; and automatically translating the update into the preferred language using predefined translations generated and entered by the clinical care environment.

12. The method of claim 9, further comprising:

verifying identity of the patient by requesting entry of additional patient information through the second device before allowing access to updates; and preventing unauthorized access to protected health information by validating the additional patient information.

13. The method of claim 9, further comprising:

enabling the family member to propose an alternative time for a scheduled call with the caregiver through the second device; and limiting communication from the family member to the caregiver to emoji responses and call time proposals to reduce interruptions to the caregiver.

* * * * *